United States Patent [19]
Urawa et al.

[11] Patent Number: 5,559,236
[45] Date of Patent: Sep. 24, 1996

[54] INTERMEDIATES FOR SUBSTITUTED BIPHENYLMETHYLMIDAZOPYRIDINE ANGIOTENSIN II ANTAGONISTS

[75] Inventors: Yoshio Urawa; Ken Furukawa; Toshikazu Shimizu; Yoji Yamagishi, all of Ibaraki; Tomio Tsurugi, Chiba; Tomio Ichino, Ibaraki, all of Japan

[73] Assignees: Eisai Co., Ltd., Tokyo; Eisai Chemical Co., Ltd., Ibaraki, both of Japan

[21] Appl. No.: 471,465

[22] Filed: Jun. 6, 1995

Related U.S. Application Data

[62] Division of Ser. No. 256,869, filed as PCT/JP93/01776, Dec. 7, 1993.

[30] Foreign Application Priority Data

| Dec. 7, 1992 | [JP] | Japan | 4-351139 |
| Dec. 16, 1992 | [JP] | Japan | 4-353865 |
| Jun. 17, 1993 | [JP] | Japan | 5-169805 |
| Jun. 17, 1993 | [JP] | Japan | 5-169823 |
| Jun. 17, 1993 | [JP] | Japan | 5-169824 |
| Jun. 17, 1993 | [JP] | Japan | 5-169825 |

[51] Int. Cl.⁶ .............. C07D 413/10; C07D 213/75
[52] U.S. Cl. .............. 546/14; 546/271.4; 546/282.1; 546/308; 546/284.4
[58] Field of Search .............. 546/14, 268, 275, 546/308

[56] References Cited

U.S. PATENT DOCUMENTS

| 5,102,880 | 4/1992 | Chakravarty et al. | 514/212 |
| 5,157,026 | 10/1992 | Chakravarty et al. | 514/81 |
| 5,250,548 | 10/1993 | Winn et al. | 514/340 |
| 5,332,744 | 7/1994 | Chakravarty et al. | 514/261 |

FOREIGN PATENT DOCUMENTS

| 0253310 | 1/1988 | European Pat. Off. |
| 0399731 | 11/1990 | European Pat. Off. |
| 0426021 | 5/1991 | European Pat. Off. |
| 0480204 | 4/1992 | European Pat. Off. |
| 0553682 | 8/1993 | European Pat. Off. |
| 63-23868 | 2/1988 | Japan |
| 35480 | 1/1991 | Japan |
| 395181 | 4/1991 | Japan |
| 3188076 | 8/1991 | Japan |
| 3236377 | 10/1991 | Japan |
| 4328986 | 11/1992 | Japan |

OTHER PUBLICATIONS

Organic Syntheses, Collective vol. 2, rev. of Annual Vol. X–XIX, pp. 134–137 (1936).
A. I. Meyers, et al., J. Org. Chem., vol. 39, No. 18, 1974, pp. 2778–2783.
Nicholas A. Cortese, et al., J. Org. Chem., vol. 42, No. 22, 1977, pp. 3491–3495.
Mervyn Israel, et al., Pyridopyrazines and Imidazopyridines, vol. 24, Oct. 1959, pp. 1455–1460.
Harold Graboyes, et al., Syntheses of Imidazopyridines and Pyridotriazoles, vol. 79, Dec. 20, 1957, pp. 6421–6427.
A. I. Meyers, et al., J. Org. Chem., vol. 43, No. 7, 1978, pp. 1372–1379.
Atwal, K. et al., J. Med. Chem. 1992, 35, (pp. 4751–4763).

*Primary Examiner*—Bernard Dentz
*Attorney, Agent, or Firm*—Birch, Stewart, Kolasch & Birch, LLP

[57] ABSTRACT

The present invention provides an industrially advantageous process for preparing a 2-alkyl-3-(biphenyl-4-yl)methyl-3H-imidazo[4,5-b]pyridine derivative represented by the following formula (II) which is a precursor of an antagonist against an angiotensin II receptor useful as an antihypertensive drug, a biphenyl derivative which is a precursor of the substituent of the pyridine derivative, a process for the preparation thereof, and an intermediate useful for the preparation of the biphenyl derivative:

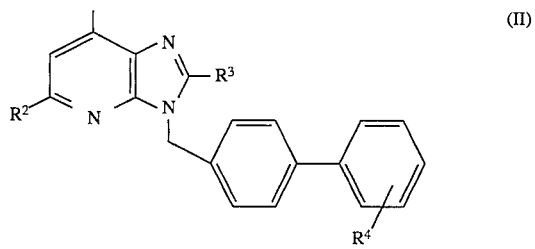

(II)

The 2-alkyl-3-(biphenyl-4-yl)methyl-3H-imidazo-[4,5-b] pyridine derivative can be prepared in a high yield according to the present invention from a 2-amino-5-halogeno-3-nitropyridine derivative through amidation, N-alkylation and reductive cyclization. The halogen atom introduced at the 5-position as a protective group against nitration can be eliminated simultaneously in the step which is conducted thereafter. Thus, this process is industrially advantageous. Further, the biphenyl derivative of the present invention is excellent in reactivity and purity of the product, thus being an intermediate suitable for the industrial production.

7 Claims, No Drawings

INTERMEDIATES FOR SUBSTITUTED BIPHENYLMETHYLMIDAZOPYRIDINE ANGIOTENSIN II ANTAGONISTS

This application is a divisional of copending application Ser. No. 08/256,869, filed on Aug. 5, 1994, the entire contents of which are hereby incorporated by reference. This application is a 371 of PCT/JP93/01776 filed Dec. 7, 1993.

DETAILED DESCRIPTION OF THE INVENTION

1. Field of Industrial Application

The present invention relates to a process for the preparation of a 2-alkyl-3-(biphenyl-4-yl)methyl- 3H-imidazo[4,5-b]pyridine derivative (II) which is disclosed in, e.g., Japanese Patent Publication-A Nos. 3-95181 (and European Patent Publication-A No. 420237 corresponding thereof) and 3-236377 and is a precursor of an antagonist against angiotensin II receptor useful as an antihypertensive drug and a remedy for hemal lesions, and an intermediate useful for the preparation thereof.

The present invention relates to a process for the preparation of a 2-alkyl-3-(2'-cyanobiphenyl-4-yl)methyl-3H-imidazo[4,5-b]pyridine derivative (II) which is disclosed in, e.g., Japanese Patent Publication-A Nos. 3-5480, 3-95181, 3-188076 (and European Patent Publication-A No. 426021 corresponding thereof) and 3-236377 (and European Patent Publication-A No. 420237 corresponding thereof), and Japanese Parent Application No. 4-328986 and is a precursor of an antagonist against angiotensin II receptor useful as an antihypertensive drug and a remedy for hemal lesions, and an intermediate useful for the preparation thereof.

The present invention relates to a biphenyloxazoline derivative (I) useful as an intermediate for the preparation of a medicine, a process for the preparation thereof, and an intermediate useful for the preparation thereof. More particularly, the present invention relates to a biphenyloxazoline derivative (I) that is a precursor for the substituent of the antagonist against angiotensin II receptor which is disclosed in, e.g., Japanese Patent Publication-A Nos. 3-95181 and 3-236377 (and European Patent Publication-A No. 420237 corresponding thereof) and Japanese Patent Application No. 4-328986 and is useful as an antihypertensive drug and a remedy for hemal lesions, a process for the preparation thereof, and an intermediate useful for the preparation thereof.

The present invention relates to a sulfonyloxy-biphenylcarboxylic ester derivative (I) useful as an intermediate for the preparation of a medicine, a process for the preparation thereof, and an intermediate useful for the preparation thereof. More particularly, the present invention relates to a sulfonyloxy-biphenylcarboxylic ester derivative (I) that is a precursor for the substituent of the antagonist against angiotensin II receptor which is disclosed in, e.g., Japanese Patent Publication-A Nos. 8-95181 and 8-286877 (and European Patent Publication-A No. 420287 corresponding thereof) and Japanese Patent Application No. 4-828986 and is useful as an antihypertensive drug and a remedy for hemal lesions, a process for the preparation thereof, and an intermediate useful for the preparation thereof.

The present invention relates to a process for the preparation of a halomethyl-biphenylcarboxylic ester derivative (II) useful as an intermediate for the preparation of a medicine. More particularly, the present invention relates to a process for the preparation of a halomethyl-biphenylcarboxylic ester derivative (II) that is a precursor for the substituent of the antagonist against angiotensin II receptor which is disclosed in, e.g., Japanese Patent Publication-A Nos. 8-95181 and 8-236377 (and European Patent Publication-A No. 420237 corresponding thereof) and Japanese Patent Application No. 4-828986 and is useful as an antihypertensive drug and a remedy for hemal lesions.

2. Prior Art

As described in the Japanese Patent Publication-A No. 3-236377, a 2-alkyl-3-(biphenyl-4-yl)methyl-3H-imidazo[4,5-b]pyridine derivative (II) has hitherto been prepared mainly by a process which comprises nitrating a 2-aminopyridine derivative into a 2-amino- 3-nitropyridine derivative, reducing it to form a 2,3-diaminopyridine derivative, conducting the N-acylation and cyclization thereof simultaneously to form a 3H-imidazo[4,5-b]pyridine ring and finally conducting the N-alkylation thereof. This preparation process of the prior art can be represented by the following reaction formula (reaction scheme-1):

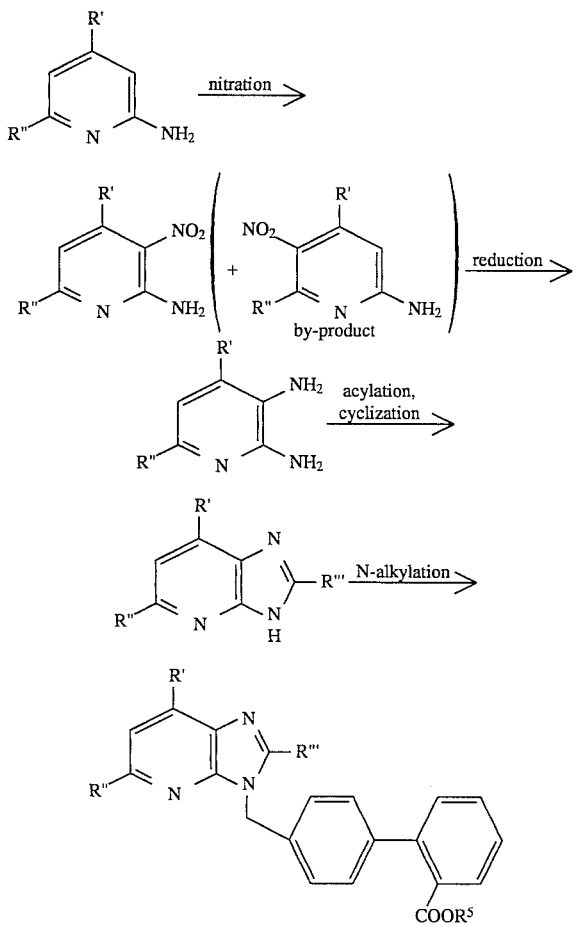

3
-continued
Reaction Scheme-1

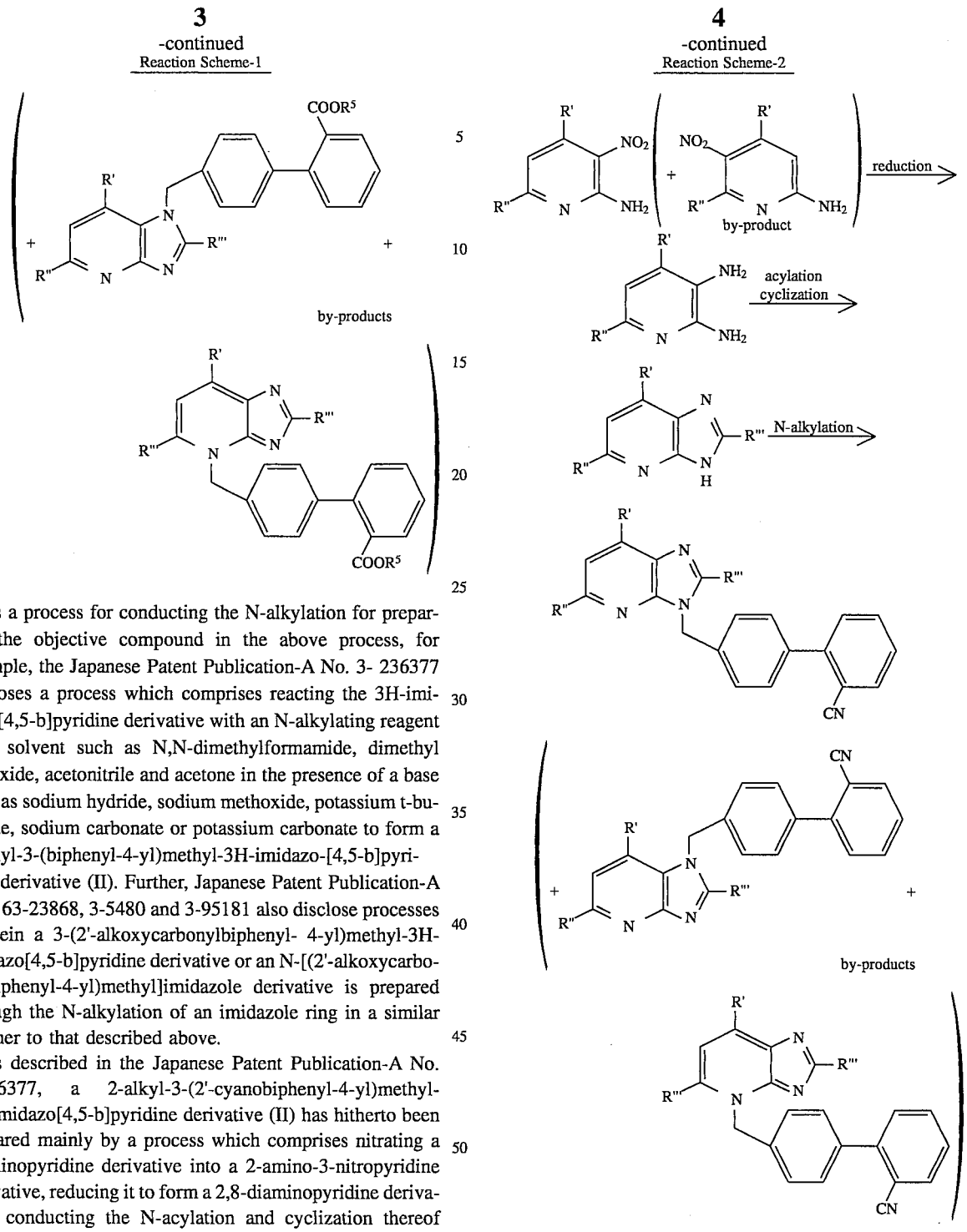

by-products

As a process for conducting the N-alkylation for preparing the objective compound in the above process, for example, the Japanese Patent Publication-A No. 3- 236377 discloses a process which comprises reacting the 3H-imidazo[4,5-b]pyridine derivative with an N-alkylating reagent in a solvent such as N,N-dimethylformamide, dimethyl sulfoxide, acetonitrile and acetone in the presence of a base such as sodium hydride, sodium methoxide, potassium t-butoxide, sodium carbonate or potassium carbonate to form a 2-alkyl-3-(biphenyl-4-yl)methyl-3H-imidazo-[4,5-b]pyridine derivative (II). Further, Japanese Patent Publication-A Nos. 63-23868, 3-5480 and 3-95181 also disclose processes wherein a 3-(2'-alkoxycarbonylbiphenyl- 4-yl)methyl-3H-imidazo[4,5-b]pyridine derivative or an N-[(2'-alkoxycarbonylbiphenyl-4-yl)methyl]imidazole derivative is prepared through the N-alkylation of an imidazole ring in a similar manner to that described above.

As described in the Japanese Patent Publication-A No. 3-236377, a 2-alkyl-3-(2'-cyanobiphenyl-4-yl)methyl-3H-imidazo[4,5-b]pyridine derivative (II) has hitherto been prepared mainly by a process which comprises nitrating a 2-aminopyridine derivative into a 2-amino-3-nitropyridine derivative, reducing it to form a 2,8-diaminopyridine derivative, conducting the N-acylation and cyclization thereof simultaneously to form a 8H-imidazo[405-b]pyridine ring and finally conducting the N-alkylation thereof. This preparation process of the prior art can be represented by the following reaction formula (reaction scheme-2):

Reaction Scheme-2

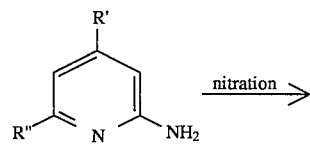

4
-continued
Reaction Scheme-2 is a process for conducting the N-alkylation for preparing the objective compound in the above process, for example. The Japanese Patent Publication-A No. 3- 236377 discloses a process which comprises reacting the 3H-imidazo[4,5-b] pyridine derivative with an N-alkylating reagent in a solvent such as N,N-dimethylformamide, dimethyl sulfoxide, acetonitrile and acetone in the presence of a base such as sodium hydride, sodium methoxide, potassium t-butoxide, sodium carbonate or potassium carbonate to form a 2-alkyl-8-(2'-cyanobiphenyl-4-yl)methyl-3H-imidazo[4,5-b]pyridine derivative (II). Further, Japanese Patent Publication-A Nos. 3-5480, 3-95181 and 3-188076 also disclose processes wherein a 8-(2'-cyanobiphenyl-4-yl)methyl-3H-imidazo[4, 5-b]-pyridine derivative is prepared through the N-alkylation of an imidazole ring in a similar manner to that described above.

As described in, e.g., Japanese Patent Publication-A No. 3-236377, it has been a practice in the prior art to form the side chain of biphenyl of a 2-alkyl-3-(2'-alkoxycarbonylbiphenyl4-yl)methyl-3H-imidazo[4,5-b]pyridine derivative which is an antagonist against angiotensin II receptor by a method wherein the N-alkylation is conducted with a 4'-bromomethyl-2-biphenylcarboxylic ester.

Such a 4'-bromomethyl-2-biphenylcarboxylic ester is prepared by a process which comprises preparing 4'-methyl-2-biphenyloxazoline in a manner described in Journal of Organic Chemistry (J. Org. Chem.), 43(7), 1372 to 1379, 1978, then hydrolyzing it into 4'-methyl-2-biphenylcarboxylic acid, then esterifying it into a 4'-methyl-2-biphenylcarboxylic ester, and, further, brominating it in a manner disclosed in the Japanese Patent Publication-A No. 63-23868. This preparation process is represented hereinafter (reaction scheme-3):

the objective 3-alkyl-3H-imidazo[4,5-b]pyridine derivative, but also a 1-alkyl-1H-imidazo[4,5-b]-pyridine derivative and a 4-alkyl-4H-imidazo[4,5-b]-pyridine derivative as by-products because the imidazo[4,5-b]pyridine ring loses the hydrogen atom owing to the abstraction by a base to result in a transition state wherein electron is delocalized. The yield of the objective compound is as low as about 20 to 40%, also in this reaction (see the above reaction schemes 1 and 2).

As described above, the process for the preparation of imidazopyridines according to the prior art involves two states problematic in yield remarkably before obtaining the objective compound, so that the process is uneconomical and takes much labor in separation and purification, being not always satisfactory as an industrial process. Under these circumstances, it has been expected to develop an industrially advantageous process by which an objective imidazopyridine derivative can be prepared from a starting 2-aminopyridine derivative in a high yield.

Reaction Scheme-3

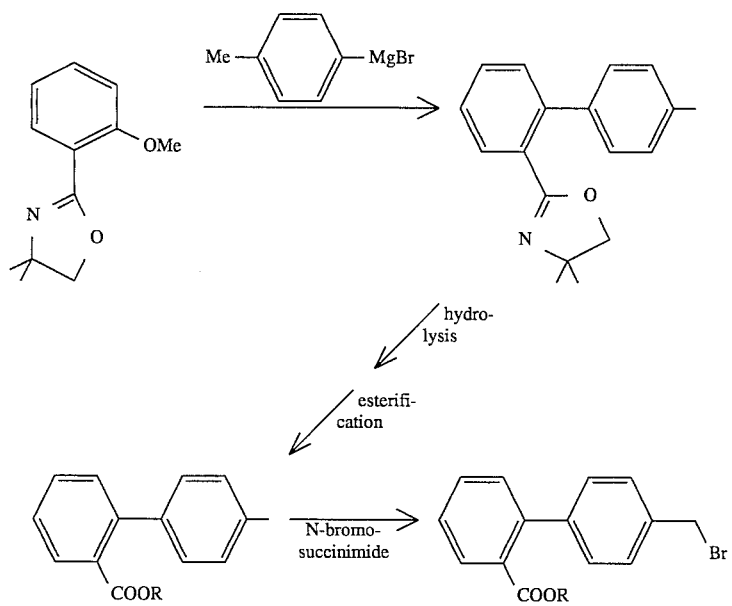

PROBLEM TO BE SOLVED BY THE INVENTION

The process for the preparation of an imidazo[4,5-b] pyridine derivative according to the prior are begins with the step of nitrating a 2-aminopyridine derivative into a 2-amino-3-nitropyridine derivative. However, the nitration step is disadvantageous. That is, a 2-aminopyridine derivative exhibits an ortho, para directivity in nitration, so that the nitration gives not only an objective 2-amino-3-nitropyridine derivative which is a product of the substitution ortho to the amino group, but also a 2-amino-5-nitropyridine derivative which is a product of the substitution para to it as a by-product. Further, the proportion of the undesired 5-nitro derivative is as overwhelmingly high as about 80 to 90%, while that of the objective derivative is as low as about 10 to 20% (see the above reaction schemes 1 and 2).

The above process of the prior art involves the step of conducting the N-alkylation of the NH group of the imidazole ring after forming imidazo[4,5-b]-pyridine ring. The N-alkylation step is also problematic in that the isomerization of the imidazopyridine ring is caused to give not only Further, as described in, for example, the Japanese Patent Publication-A No. 3-236377, it has been a practice in the prior art to form the biphenyl moiety of a 2-alkyl-3-(2'-alkoxycarbonylbiphenyl- 4-yl)methyl-3H-imidazo[4,5-b] pyridine derivative by the N-alkylation with a 2-(4'-bromomethylphenyl)benzoic acid ester. However, the preparation of the 2-(4'-bromomethylphenyl)benzoic acid ester according to the process disclosed in the Japanese Patent Publication-A No. 63-23868has the disadvantage that it is not suitable for an industrial production thereof because the N-bromosuccinimide, which is used for the bromination is expensive and the bromination is a free-radical reaction and therefore is too rapid to be controlled.

Furthermore, a 2-(4-bromomethylphenyl)benzoic acid ester has a high activity to react easily, but it could not be stored stably because of the high activity, so that it had to be prepared immediately before the use and was extremely poor in workability. Furthermore, owing to the high activity, the ester has a disadvantage of being liable to cause decomposition or a side reaction in the reaction, so that the obtained N-alkylation product had a low purity and was contaminated with many by-products to result in difficult purification. Under these circumstances, it has also been expected to find a novel imidazopyridine derivative which is prepared by using, as an N-alkylating agent, an active biphenyl derivative (IV) which is excellent in reactivity and operability and gives a high-purity product.

Further, with the purpose of solving the above problem, the Japanese Patent Publication-A No. 3-95181 discloses a process which comprises conducting the N-acylation and cyclization of starting 5-bromo-4-methyl- 2,3-diaminopyridine simultaneously to form 6-bromo-2-butyl-7-methyl-3H-imidazo[4,5-b]pyridine and treating it with n-butyllithium and methanol successively to form 2-butyl-7-methyl-3H-imidazo[4,5-b]pyridine. Although this process could give the objective compound in a high yield, the process was insufficient as an industrial one because it uses n-butyllithium which is very dangerous owing to its high ignitability and is expensive, necessitates the preparation of an anhydrous solvent prior to the reaction and requires specialized production facilities for maintaining the anhydrous state.

Furthermore, the Japanese Patent Publication-A No. 3-188076 discloses a process for preparing 2-butyl-3-(2'-cyanobiphenyl-4-yl)methyl-6-bromo- 7-methyl-3H-imidazo[4,5-b]pyridine by reacting a 2-[N-(2'-cyanobiphenyl-4-yl)methyl-N-valeryl]amino-5-bromo- 4-methyl-3-nitropyridine with iron in acetic acid. However, this patent document is silent on the means of dehalogenation. Accordingly, it was impossible to prepare the 3-alkyl-3H-imidazo[4,5-b]pyridine derivative which is a precursor of an antagonist against angiotensin II receptor and which corresponds to a compound prepared by replacing the 6-position bromine atom of the above imidazopyridine by a hydrogen atom.

Under these circumstances, it has been expected to develop an industrially advantageous process preparing a 2-alkyl-3-(2'-cyanobiphenyl-4-yl)methyl- 3H-imidazo[4,5-b]pyridine derivative (II) from a 2-amino-5-halogeno-4-methyl-3-nitropyridine derivative (I) with safety in a high yield.

The 4'-bromomethyl-2-biphenylcarboxylic ester which has hitherto been used has a high activity react easily, but it could not be stored because was poor in stability due to its high activity. Therefore, it had been prepared immediately before the use and was extremely poor in workability. Further, due to the high activity, the ester also has a disadvantage of being liable to cause decomposition a side reaction in the reaction, so that the obtained N-alkylation product had a low purity and the by-products were varied to result in difficult purification. Furthermore, all of the processes disclosed in the prior art failed in the preparation of a 4'-chloromethyl-2-biphenylcarboxylic ester exhibiting a desirable reactivity in the N-alkylation.

Further, N-bromosuccinimide has been used for the bromination in the preparation of the 4'-bromomethyl- 2-biphenylcarboxylic ester according to the process disclosed in the Japanese Patent Publication-A No. 63- 23868. However, there has been a disadvantage that it is unsuitable for the industrial production thereof because this reagent is expensive and the bromination is a free-radical reaction and therefore is too rapid to be controlled.

Further, the 4'-bromomethyl-2-biphenylcarboxylic ester which has hitherto been used has a high activity to react easily, but it could not be stored because it was poor in stability due to its high activity. Therefore, it had been prepared immediately before the use and was extremely poor in workability. Furthermore, due to the high activity, the ester also has a disadvantage of being liable to cause decomposition or a side reaction in the reaction, so that the obtained N-alkylation product had a low purity and the by-products were varied to result in difficult purification. Under these circumstances, an active 4'-chloromethyl-2-biphenylcarboxylic ester and the like excellent in operability have also been expected, but the process disclosed in the Japanese Patent Publication-A No. 63-23868 failed in the preparation thereof.

As described above, the 4'-bromomethyl-2-biphenylcarboxylic ester which has hitherto been used took much labor to separate and purify the N-alkylation product and had disadvantages in economic efficiency and safeness, in addition to its poor working efficiency as an intermediate. Thus, the ester was not always satisfactory as an intermediate for industrial production.

Under these circumstances, an industrially advantageous active biphenyl intermediate with which the imidazopyridine derivative useful as an antagonist against angiotensin II receptor can be prepared safely in a high yield at a high purity and a high economic efficiency has been expected. Additionally, an industrially advantageous process for preparing a halomethyl-biphenylcarboxylic ester derivative (such as a 4'-chloromethyl-2-biphenylcarboxylic ester) with which the imidazopyridine derivative useful as an antagonist against angiotensin II receptor can be prepared safely in a high yield at a high purity and a high economic efficiency and which has a desirable activity.

DESCRIPTION OF THE INVENTION

The present inventors have extensively studied with top priority being given to an improvement in the yield of the N-alkylation and also with the purpose of improving the nitration step, because, in the production of an imidazopyridine derivative as an objective compound, lower the yield of a step near the final one in a process, less efficious the process as an industrial one. As a result, they have found that the above objects can be attained and a 2-alkyl-3-(biphenyl-4-yl)methyl-3H-imidazo[4,5-b]pyridine derivative (II) can be produced by converting a 2-amino-3-nitropyridine derivative (V) into a 2-[N-(biphenyl-4-yl)methyl]-alkylamido-3-nitropyridine derivative (I) through amidation followed by N-alkylation and conducting the cyclization thereof under reducing conditions. The present invention has been accomplished on the basis of this finding.

Meanwhile, it is known that a 2-amino-5-bromopyridine derivative or 2-amino-5-chloropyridine derivative can be prepared from a 2-aminopyridine derivative by bromination or chlorination in a high yield [see Journal of American Chemical Society (J.A.C.S.), 79, 6421 to 6426, 1957, Journal of Organic Chemistry (J. Org. Chem.), 24, 1455 to 1460, 1959 and so forth]. The present inventors have also found that such a 2-amino-5-halogenopyridine derivative as a starting material can be selectively nitrated into a 3-nitro derivative by virtue of the presence of a halogen atom at the 5-position of the derivative, by which the problem of the nitration process according to the prior art can be solved.

Further, the present invention is advantageous that no particular step is necessitated for eliminating the halogen atom introduced at the 5-position as a protecting group against nitration because the halogen atom at the 5-position can be eliminated and replaced by a hydrogen atom simultaneously with the reductive cyclization of the final step. Accordingly, the process of the present invention is industrially advantageous.

Further, the present inventors have also found that the objective imidazopyridine derivative can be prepared at high purity with excellent operability by using an active biphenyl derivative (IV), examples of which include not only 2-(4'-bromomethylphenyl)benzoic acid esters which have hitherto been used, but also 2-(4'-chloromethylphenyl)benzoic acid esters, 2-( 4'-alkylsulfonyloxymethylphenyl)benzoic acid ester derivatives, 2-(4'-arylsulfonyloxymethylphenyl- )benzoic acid ester derivatives, 4,4-dimethyl-2-(4'-hydroxymethylbiphenyl- 2-yl)oxazoline, 4,4-dimethyl-2-(4'-halomethylbiphenyl-2-yl)oxazoline derivatives, 4,4-dimethyl-2-(4'-alkylsulfonyloxymethylbiphenyl- 2-yl)oxazoline derivatives and 4,4-dimethyl-2-(4'-arylsulfonyloxymethyl-biphenyl- 2-yl)oxazoline derivatives, and has been accomplished the present invention. The outline of the reaction path according to the present invention is represented by the following chemical reaction formula (reaction scheme- 4):

Reaction Scheme-4

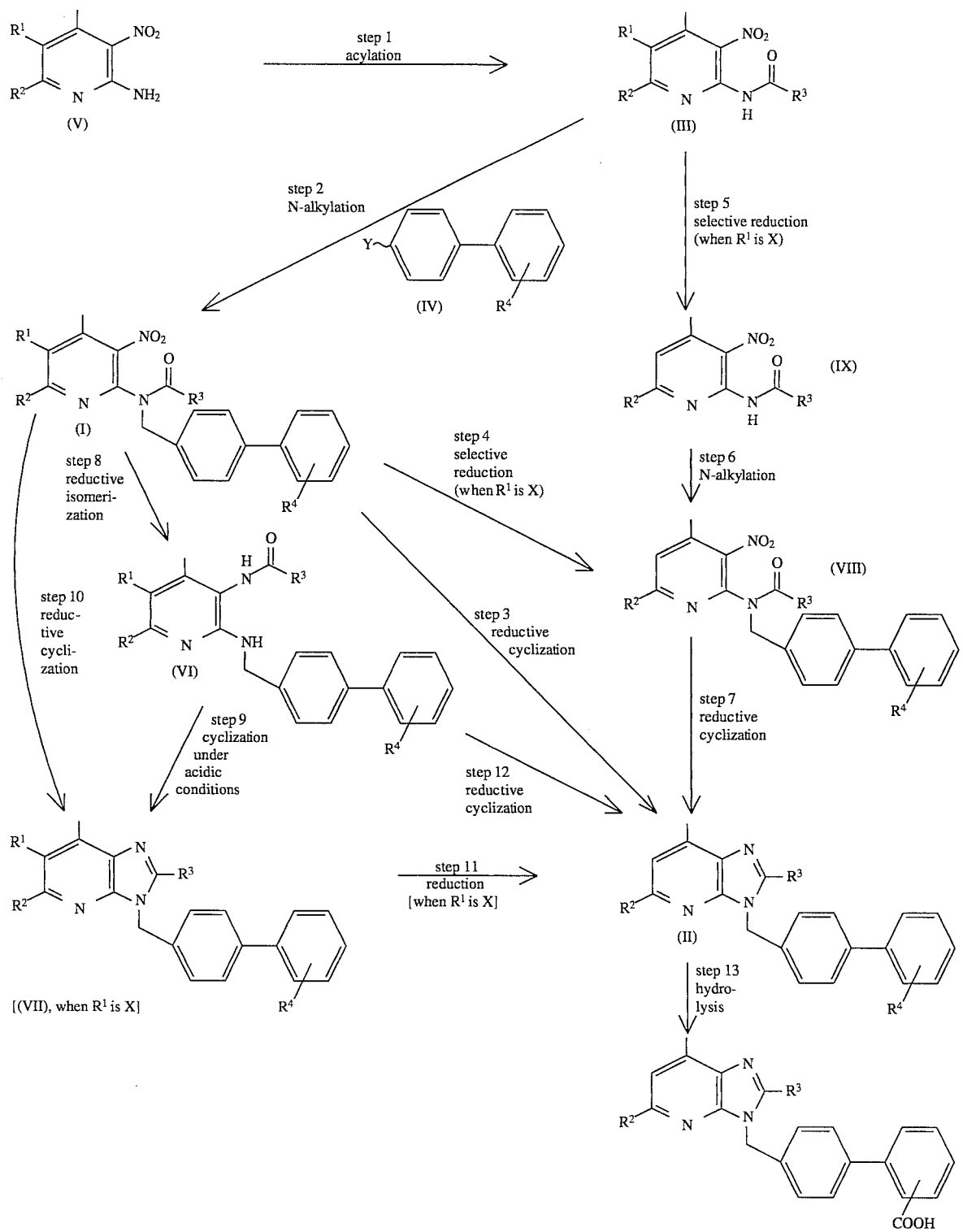

Accordingly, an object of the present invention is to provide an industrially advantageous process for the preparation of a 2-alkyl-8-(biphenyl-4-yl)methyl- 3H-imidazo[4,5-b]pyridine derivative (II) which is a precursor of an antagonist against an angiotensin II receptor useful as an antihypertensive drug or a remedy for hemal lesions.

Then, the 2-[N-(biphenyl-4-yl)methyl]alkylamido- 3-nitropyridine derivative (I) according to the present invention has the following chemical structural formula:

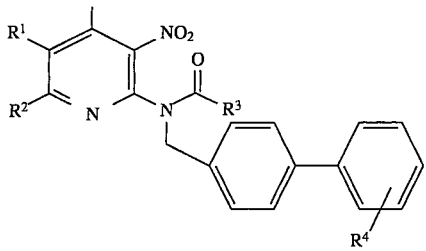

wherein $R^1$ represents a hydrogen atom or a halogen atom, with the proviso that the halogen atom is a bromine atom or a chlorine atom; $R^2$ represents a hydrogen atom or a methyl group; $R^3$ represents a cycloalkyl group, a lower alkyl group or a lower alkoxy group; and $R^4$ represents a group represented by the following general formula:

—COOR$^5$

[wherein $R^5$ represents a lower alkyl group, a cycloalkyl group, an alkoxyalkyl group, a thioalkoxyalkyl group, a cycloether group, an aryl group, an aralkyl group, an alkenyl group, an alkynyl group or a trialkylsilyl group] or a group represented by the following general formula:

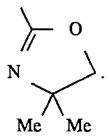

Specific examples of $R^3$ include cycloalkyl groups such as a cyclopropyl group, a cyclobutyl group, a cyclopentyl group and a cyclohexyl group, lower alkyl groups such as alkyl groups having 1 to 6 carbon atoms, e.g., a methyl group, an ethyl group, a n-propyl group, an i-propyl group, a n-butyl group, an i-butyl group, a t-butyl group, an amyl group and a hexyl group, and lower alkoxy groups such as lower alkoxy groups having 1 to 6 carbon atoms, e.g., a methoxy group, an ethoxy group, a n-propoxy group, an i-propoxy group, a butoxy group, a pentyloxy group and a hexyloxy group.

Specific examples of $R^5$ include lower alkyl groups such as alkyl groups having 1 to 10 carbon atoms, e.g., a methyl group, an ethyl group, a n-propyl group, an i-propyl group, a n-butyl group, an i-butyl group, a t-butyl group, a n-pentyl group, an i-pentyl group, a t-pentyl group, a hexyl group, an octyl group and a decyl group; cycloalkyl groups such as a cyclopropyl group, a cyclobutyl group, a cyclopentyl group and a cyclohexyl group; alkoxyalkyl groups such as a methoxymethyl group, an ethoxymethyl group, a methoxyethyl group, an ethoxyethyl group, a methoxyethoxymethyl group, a phenoxymethyl group and a benzyloxymethyl group; thioalkoxyalkyl groups such as a methylthiomethyl group, a methylthioethyl group, an ethylthiomethyl group, a phenylthiomethyl group and a benzylthiomethyl group; cycloether groups such as a tetrahydropyranyl group and a tetrahydrofuranyl group; aryl groups such as a phenyl group, a tolyl group and a xylyl group; aralkyl groups such as a benzyl group, a phenethyl group, a methylbenzyl group, a trimethylbenzyl group, a nitrobenzyl group and a phenacyl group; alkenyl groups such as an allyl group, a propenyl group and a cinnamyl group; alkynyl groups such as a propargyl group; and trialkylsilyl groups such as a trimethylsilyl group, a triethylsilyl group, t-butyldimethylsilyl group, an i-propyldimethylsilyl group and a phenyldimethylsilyl group. Among them, preferable ones include lower alkyl groups having 1 to 6 carbon atoms, a cycloalkyl group, a methoxymethyl group, a tetrahydropyranyl group, a phenyl group, a benzyl group and a trimethylsilyl group.

Further, specific and representative examples the 2-[N-(biphenyl-4-yl)methyl]alkylamido-3-nitropyridine derivative (I) according to the present invention include, for example, the following compounds, though the derivative (I) is not limited to them.

(1) 2-[N-(2'-methoxycarbonylbiphenyl-4-yl)methyl]-cyclopropanecarboxamido-4-methyl-3-nitropyridine
(2) 2-[N-(2'-methoxycarbonylbiphenyl-4-yl)methyl]-cyclopropanecarboxamido-4,6-dimethyl-3-nitropyridine
(3) 2-[N-(2'-methoxycarbonylbiphenyl-4-yl)methyl]-cyclopropanecarboxamido-5-bromo-4-methyl-3-nitropyridine
(4) 2-[N-(2'-methoxycarbonylbiphenyl-4-yl)methyl]-cyclopropanecarboxamido-5-chloro-4-methyl-3-nitropyridine
(5) 2-[N-(2'-methoxycarbonylbiphenyl-4-yl)methyl]-cyclopropanecarboxamido-5-bromo-4,6-dimethyl-3-nitropyridine
(6) 2-[N-(2'-methoxycarbonylbiphenyl-4-yl)methyl]-cyclopropanecarboxamido-5-chloro-4,6-dimethyl-3-nitropyridine
(7) 2-[N-(2'-methoxycarbonylbiphenyl-4-yl)methyl]-butyrylamino-4-methyl-3-nitropyridine
(8) 2-[N-(2'-methoxycarbonylbiphenyl-4-yl)methyl]-butyrylamino-4,6-dimethyl-3-nitropyridine
(9) 2-[N-(2'-methoxycarbonylbiphenyl-4-yl)methyl]-butyrylamino-5-bromo-4-methyl-3-nitropyridine
(10) 2-[N-(2'-methoxycarbonylbiphenyl-4-yl)methyl]-butyrylamino-5-bromo-4,6-dimethyl-3-nitropyridine
(11) 2-[N-(2'-methoxycarbonylbiphenyl-4-yl)methyl]-valerylamino-4-methyl-3-nitropyridine
(12) 2-[N-(2'-methoxycarbonylbiphenyl-4-yl)methyl]-valerylamino-4,6-dimethyl-3-nitropyridine
(13) 2-[N-(2'-methoxycarbonylbiphenyl-4-yl)methyl]-valerylamino-5-bromo-4-methyl-3-nitropyridine
(14) 2-[N-(2'-methoxycarbonylbiphenyl-4-yl)methyl]-valerylamino-5-bromo-4,6-dimethyl-3-nitropyridine
(15) 2-[N-{2'-(4",4"-dimethyloxazolin-2"-yl)biphenyl-4-yl}methyl]cyclopropanecarboxamido-4-methyl-3-nitropyridine
(16) 2-[N-{2'-(4",4"-dimethyloxazolin-2"-yl)biphenyl-4-yl}methyl]cyclopropanecarboxamido-4,6-dimethyl-3-nitropyridine
(17) 2-[N-{2'-(4",4"-dimethyloxazolin-2"-yl)biphenyl-4-yl}methyl]cyclopropanecarboxamido-5-bromo-4-methyl- 3-nitropyridine
(18) 2-[N-{2'-(4",4"-dimethyloxazolin-2"-yl)biphenyl-4-yl}methyl]cyclopropanecarboxamido-5-chloro-4-methyl- 3-nitropyridine
(19) 2-[N-{2'-(4",4"-dimethyloxazolin-2"-yl)biphenyl-4-yl}methyl]cyclopropanecarboxamido-5-bromo-4,6-dimethyl-3-nitropyridine
(20) 2-[N-{2'-(4",4"-dimethyloxazolin-2"-yl)biphenyl-4-yl}methyl]cyclopropanecarboxamido-5-chloro-4,6-dimethyl-3-nitropyridine
(21) 2-[N-{2'-(4",4"-dimethyloxazolin-2"-yl)biphenyl-4-yl}methyl]butyrylamino-4-methyl-3-nitropyridine

(22) 2-[N-{2'-(4",4"-dimethyloxazolin-2"-yl)biphenyl-4-yl}methyl]butyrylamino-4,6-dimethyl-3-nitropyridine
(23) 2-[N-{2'-(4",4"-dimethyloxazolin-2"-yl)biphenyl-4-yl}methyl]butyrylamino-5-bromo-4-methyl-3-nitropyridine
(24) 2-[N-{2'-(4",4"-dimethyloxazolin-2"-yl)biphenyl-4-yl}methyl]butyrylamino-5-bromo-4,6-dimethyl-3-nitropyridine
(25) 2-[N-{2'-(4",4"-dimethyloxazolin-2"-yl)biphenyl-4-yl}methyl]valerylamino-4-methyl-3-nitropyridine
(26) 2-[N-{2'-(4",4"-dimethyloxazolin-2"-yl)-biphenyl-4-yl}methyl]valerylamino-4,6-dimethyl-3-nitropyridine
(27) 2-[N-{2'-(4",4"-dimethyloxazolin-2"-yl)biphenyl-4-yl}methyl]valerylamino-5-bromo-4-methyl-3-nitropyridine
(28) 2-[N-{2'-(4",4"-dimethyloxazolin-2"-yl)biphenyl-4-yl}methyl]valerylamino-5-bromo-4,6-dimethyl-3-nitropyridine The 2-alkyl-3-(biphenyl-4-yl)methyl-3H-imidazo-[4,5-b]pyridine derivative (II) according to the present invention is represented by the following structural formula:

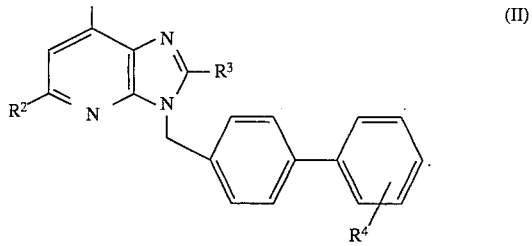

In the formula, R², R³ and R⁴ are each as defined above. Specific and representative examples of the 2-alkyl-3-(biphenyl-4-yl)methyl-3H-imidazo[4,5-b]-pyridine derivative (II) according to the present invention include, for example, the following compounds, though the derivative (II) is not limited to them.
(1) 2-cyclopropyl-3-(2'-methoxycarbonylbiphenyl-4 -yl)methyl-7-methyl-3H-imidazo[4,5-b]pyridine
(2) 2-cyclopropyl-3-(2'-methoxycarbonylbiphenyl-4 -yl)methyl-5,7-dimethyl-3H-imidazo[4,5-b]pyridine
(3) 2-n-propyl-3-(2'-methoxycarbonylbiphenyl-4 -yl)methyl-7-methyl-3H-imidazo[4,5-b]pyridine
(4) 2-n-propyl-3-(2'-methoxycarbonylbiphenyl-4 -yl)methyl-5,7-dimethyl-3H-imidazo[4,5-b]pyridine
(5) 2-n-butyl-3-(2'-methoxycarbonylbiphenyl-4-yl) -methyl-7-methyl-3H-imidazo[4,5-b]pyridine
(6) 2-n-butyl-3-(2'-methoxycarbonylbiphenyl-4-yl) -methyl-5,7-dimethyl-3H-imidazo[4,5b]pyridine
(7) 2-ethyl-8-(2'-methoxycarbonylbiphenyl-4-yl) -methyl-7-methyl-3H-imidazo[4,5-b]pyridine
(8) 2-ethyl-8-(2'-methoxycarbonylbiphenyl-4-yl) -methyl-5,7-dimethyl-3H-imidazo[4,5-b]pyridine
(9) 2-cyclopropyl-8-[2'-(4", 4"-dimethyloxazolin-2"-yl)biphenyl-4-yl]methyl-7-methyl-3H-imidazo[4,5-b]-pyridine
(10) 2-cyclopropyl-8-[2'-(4",4"-dimethyloxazolin-2"-yl)biphenyl-4-yl]methyl-5,7-dimethyl-3H-imidazo[4,5-b]pyridine
(11) 2-n-propyl-8-[2'-(4",4"-dimethyloxazolin-2"-yl) -biphenyl-4-yl]methyl-7-methyl-3H-imidazo[4,5-b]-pyridine
(12) 2-n-propyl-8-[2'-(4",4"-dimethyloxazolin-2" -yl)biphenyl-4-yl]methyl-5,7-dimethyl-3H-imidazo-[4,5-b]pyridine
(13) 2-n-butyl-8-[2'-(4",4"-dimethyloxazolin-2"-yl)biphenyl-4-yl]methyl-7-methyl-3H-imidazo[4,5-b]pyridine
(14) 2-n-butyl-8-[2'-(4",4"-dimethyloxazolin-2"-yl)biphenyl-4-yl]methyl-B,7-dimethyl-3H-imidazo- 4,5-b]pyridine
(15) 2-ethyl-8-[2'-(4",4"-dimethyloxazolin-2"-yl) -biphenyl-4-yl]methyl-7-methyl-3H-imidazo[4,5-b]-pyridine
(16) 2-ethyl-8-[2'-(4",4"-dimethyloxazolin-2"-yl) -biphenyl-4-yl]methyl-5,7-dimethyl-3H-imidazo[4,5-b]-pyridine The 2-alkylamido-3-nitropyridine derivative (III) obtained in step 1 is represented by the following chemical structural formula:

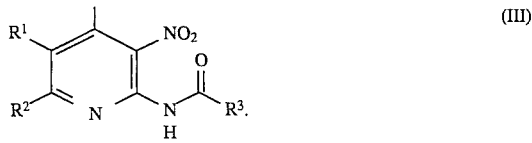

In the formula, R¹, R² and R³ are each as defined above. Further, specific examples of the 2-alkylamido- 3-nitropyridine derivative (III) according to the present invention include the following compounds, though the derivative (III) is not limited to them.
(1) 2-cyclopropanecarboxamido-4-methyl-3-nitropyridine
(2) 2-cyclopropanecarboxamido-4,6-dimethyl-3-nitropyridine
(3) 2-cyclopropanecarboxamido-5-bromo-4-methyl-3-nitropyridine
(4) 2-cyclopropanecarboxamido-5-chloro-4-methyl-3-nitropyridine
(5) 2-cyclopropanecarboxamido-5-bromo-4,6-dimethyl-3-nitropyridine
(6) 2-cyclopropanecarboxamido-5-chloro-4,6-dimethyl-3-nitropyridine
(7) 2-butyrylamino-4-methyl-3-nitropyridine
(8) 2-butyrylamino-4,6-dimethyl-3-nitropyridine
(9) 2-butyrylamino-5-bromo-4-methyl-3-nitropyridine
(10) 2-butyrylamino-5-bromo-4,6-dimethyl-3-nitropyridine
(11) 2-valerylamino-4-methyl-3-nitropyridine
(12) 2-valerylamino-4,6-dimethyl-3-nitropyridine
(13) 2-valerylamino-5-bromo-4-methyl-3-nitropyridine
(14) 2-valerylamino-5-bromo-4,6-dimethyl-3-nitropyridine The active biphenyl derivative (IV) according to the present invention is represented by the following general formula:

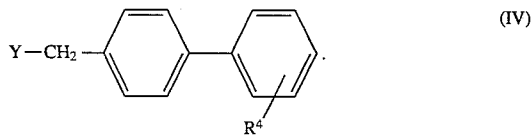

In the formula, Y represents a leaving group in the course of organic synthesis, preferably a hydroxyl group, a halogen atom, a lower alkylsulfonyl-oxy group or an arylsulfonyloxy group; and R⁴ is as defined above. Specific examples of the halogen atom include a chlorine atom, a bromine atom, an iodine atom and a fluorine atom; those of the lower alkylsulfonyloxy group include groups having a lower alkyl group of 1 to 6 carbon atoms in the molecule, such as a methanesulfonyloxy group and an ethanesulfonyloxy group; and those of the arylsulfonyloxy group include a benzenesulfonyloxy group and a p-toluenesulfonyloxy group. Furthermore, specific examples of the active biphenyl derivative (IV) according to the present invention include The following compounds, though the derivative (IV) is not limited to them. These compounds can be prepared by the process disclosed in the Japanese Patent Publication-A No. 3-236377 and the processes described hereinafter.
(1) methyl 2-(4'-hydroxymethylphenyl)benzoate (2) methyl 3-(4'-hydroxymethylphenyl)benzoate
(3) methyl 4-(4'-hydroxymethylphenyl)benzoate
(4) ethyl 2-(4'-hydroxymethylphenyl)benzoate
(5) ethyl 3-(4'-hydroxymethylphenyl)benzoate
(6) ethyl 4-(4'-hydroxymethylphenyl)benzoate
(7) propyl 2-(4'-hydroxymethylphenyl)benzoate
(8) butyl 2-(4'-hydroxymethylphenyl)benzoate
(9) phenyl 2-(4'-hydroxymethylphenyl)benzoate
(10) benzyl 2-(4'-hydroxymethylphenyl)benzoate
(11) tetrahydropyranyl 2-(4'-hydroxymethylphenyl)benzoate
(12) tetrahydrofuranyl 2-(4'-hydroxymethylphenyl)benzoate
(13) trimethylsilyl 2-(4'-hydroxymethylphenyl)benzoate
(14) methoxymethyl 2-(4'-hydroxymethylphenyl)benzoate
(15) thiomethoxymethyl 2-(4'-hydroxymethylphenyl)benzoate
(16) methyl 2-(4'-bromomethylphenyl)benzoate
(17) methyl 3-(4'-bromomethylphenyl)benzoate
(18) methyl 4-(4'-bromomethylphenyl)benzoate
(19) methyl 2-(4'-chloromethylphenyl)benzoate
(20) methyl 3-(4'-chloromethylphenyl)benzoate
(21) methyl 4-(4'-chloromethylphenyl)benzoate
(22) methyl 2-(4'-methanesulfonyloxymethylphenyl)benzoate
(23) methyl 38-(4'-methanesulfonyloxymethylphenyl)benzoate
(24) methyl 4-(4'-methanesulfonyloxymethylphenyl)benzoate
(25) ethyl 2-(4'-methanesulfonyloxymethylphenyl)benzoate
(26) ethyl 3-(4'-methanesulfonyloxymethylphenyl)benzoate
(27) ethyl 4-(4'-methanesulfonyloxymethylphenyl)benzoate
(28) methyl 2-(4'-ethanesulfonyloxymethylphenyl)benzoate
(29) methyl 3-(4'-ethanesulfonyloxymethylphenyl)benzoate
(30) methyl 4-(4'-ethanesulfonyloxymethylphenyl)benzoate
(31) ethyl 2-(4'-ethanesulfonyloxymethylphenyl)benzoate
(32) ethyl 3-(4'-ethanesulfonyloxymethylphenyl)benzoate
(33) ethyl 4-(4'-ethanesulfonyloxymethylphenyl)benzoate
(34) methyl 2-(4'-p-toluenesulfonyloxymethylphenyl)benzoate
(35) methyl 3-(4'-p-toluenesulfonyloxymethylphenyl)benzoate
(36) methyl 4-(4'-p-toluenesulfonyloxymethylphenyl)benzoate
(37) ethyl 2-(4'-p-toluenesulfonyloxymethylphenyl)benzoate
(38) ethyl 3-(4'-p-toluenesulfonyloxymethylphenyl)benzoate
(39) ethyl 4-(4'-p-toluenesulfonyloxymethylphenyl)benzoate
(40) methyl 2-(4'-benzenesulfonyloxymethylphenyl)benzoate
(41) methyl 3-(4'-benzenesulfonyloxymethylphenyl)benzoate
(42) methyl 4-(4'-benzenesulfonyloxymethylphenyl)benzoate
(43) ethyl 2-(4'-benzenesulfonyloxymethylphenyl)benzoate
(44) ethyl 3-(4'-benzenesulfonyloxymethylphenyl)benzoate
(45) ethyl 4-(4'-benzenesulfonyloxymethylphenyl)benzoate
(46) 4,4-dimethyl-2-(4'-hydroxymethylbiphenyl-2-yl)oxazoline
(47) 4,4-dimethyl-2-(4'-bromomethylbiphenyl-2-yl)-oxazoline
(48) 4,4-dimethyl-2-(4'-chloromethylbiphenyl-2-yl)oxazoline
(49) 4,4-dimethyl-2-(4'-methanesulfonyloxymethylbiphenyl- 2-yl)oxazoline
(50) 4,4-dimethyl-2-(4'-ethanesulfonyloxymethylbiphenyl-2-yl)oxazoline
(51) 4,4-dimethyl-2-(4'-benzenesulfonyloxymethylbiphenyl- 2-yl)oxazoline
(52) 4,4-dimethyl-2-[4'-(p-toluenesulfonyloxymethyl)biphenyl- 2-yl)oxazoline Then, the 2-amino-3-nitropyridine derivative (V) according to the present invention is a known substance and is represented by the following general formula:

In the formula, $R^1$ and $R^2$ are each as defined above. Further, specific examples of the 2-amino- 3-nitropyridine derivative (V) according to the present invention include the following compounds, though the derivative (V) is not limited to them.
(1) 2-amino-4-methyl-3-nitropyridine
(2) 2-amino-4,6-dimethyl-3-nitropyridine
(3) 2-amino-5-bromo-4-methyl-3-nitropyridine
(4) 2-amino-5-chloro-4-methyl-3-nitropyridine
(5) 2-amino-5-bromo-4,6-dimethyl-3-nitropyridine
(6) 2-amino-5-chloro-4,6-dimethyl-3-nitropyridine The 2-[N-(biphenyl-4-yl)methyl]amino-3-alkylamidopyridine derivative (VI) prepared in step 8 is represented by the following general formula:

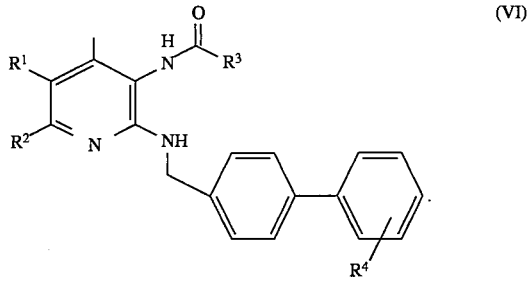

In the formula, $R^1$, $R^2$, $R^3$ and $R^4$ are each as defined above. Specific examples of the 2-[N-(biphenyl- 4-yl)methyl]amino-3-alkylamidopyridine derivative (VI) according to the present invention include the following compounds, though the derivative (VI) is not limited to them.
(1) 3-cyclopropanecarboxamido-2-[N-(2'-methoxycarbonylbiphenyl- 4-yl)methyl]amino-4-methylpyridine
(2) 3-cyclopropanecarboxamido-2-[N-(2'-methoxycarbonylbiphenyl- 4-yl)methyl]amino-4,6-dimethylpyridine
(3) 3-cyclopropanecarboxamido-2-[N-(2'-methoxycarbonylbiphenyl- 4-yl)methyl]amino-5-bromo-4-methylpyridine
(4) 3-cyclopropanecarboxamido-2-[N-(2'-methoxycarbonylbiphenyl- 4-yl)methyl]amino-5-chloro-4-methylpyridine
(5) 3-cyclopropanecarboxamido-2-[N-(2'-methoxycarbonylbiphenyl- 4-yl)methyl]amino-5-bromo-4,6-dimethylpyridine
(6) 3-cyclopropanecarboxamido-2-[N-(2'-methoxycarbonylbiphenyl- 4-yl)methyl]amino-5-chloro-4,6-dimethylpyridine
(7) 3-butyrylamino-2-[N-(2'-methoxycarbonylbiphenyl-4-yl)methyl]amino-4-methylpyridine
(8) 3-butyrylamino-2-[N-(2'-methoxycarbonylbiphenyl-4-yl)methyl]amino-4,6-dimethylpyridine
(9) 3-butyrylamino-2-[N-(2'-methoxycarbonylbiphenyl-4-yl)methyl]amino-5-bromo-4-methylpyridine
(10) 3-butyrylamino-2-[N-(2'-methoxycarbonylbiphenyl-4-yl)methyl]amino-5-bromo-4,6-dimethylpyridine

(11) 3-valerylamino-2-[N-(2'-methoxycarbonylbiphenyl-4-yl)methyl]amino-4-methylpyridine
(12) 3-valerylamino-2-[N-(2'-methoxycarbonylbiphenyl-4-yl)methyl]amino-4,6-dimethylpyridine
(13) 3-valerylamino-2-[N-(2'-methoxycarbonylbiphenyl-4-yl)methyl]amino-5-bromo-4-methylpyridine
(14) 3-valerylamino-2-[N-(2'-methoxycarbonylbiphenyl-4-yl)methyl]amino-5-bromo-4,6-dimethylpyridine
(15) 3-cyclopropanecarboxamido-2-[N-{2'-(4",4"-dimethyloxazolin-2"-yl)biphenyl-4-yl}methyl]amino-4-methylpyridine
(16) 3-cyclopropanecarboxamido-2-[N-{2'-(4",4"-dimethyloxazolin-2"-yl)biphenyl-4-yl}methyl]amino-4,6-dimethylpyridine
(17) 3-cyclopropanecarboxamido-2-[N-{2'-(4",4"-dimethyloxazolin-2"-yl)biphenyl-4-yl}methyl]amino-5-bromo-4-methylpyridine
(18) 3-cyclopropanecarboxamido-2-[N-{2'-(4",4"-dimethyloxazolin-2"-yl)biphenyl-4-yl}methyl]amino-5-chloro-4-methylpyridine
(19) 3-cyclopropanecarboxamido-2-[N-{2'-(4",4"-dimethyloxazolin-2"-yl)biphenyl-4-yl}methyl]amino-5-bromo-4,6-dimethylpyridine
(20) 3-cyclopropanecarboxamido-2-[N-{2'-(4",4"-dimethyloxazolin-2"-yl)biphenyl-4-yl}methyl]amino-5-chloro-4,6-dimethylpyridine
(21) 3-butyrylamino-2-[N-{2'-(4",4"-dimethyloxazolin-2"-yl)biphenyl-4-yl}methyl]amino-4-methylpyridine
(22) 3-butyrylamino-2-[N-{2'-(4",4"-dimethyloxazolin-2"-yl)biphenyl-4-yl}methyl]amino-4,6-dimethylpyridine
(23) 3-butyrylamino-2-[N-{2'-(4",4"-dimethyloxazolin-2"-yl)biphenyl-4-yl}methyl]amino-5bromo-4-methylpyridine
(24) 3-butyrylamino-2-[N-{2'-(4",4"-dimethyloxazolin-2"-yl)biphenyl-4-yl}methyl]amino-5-bromo-4,6-dimethylpyridine
(25) 3-valerylamino-2-[N-{2'-(4",4"-dimethyloxazolin-2"-yl)biphenyl-4-yl}methyl]amino-4-methylpyridine
(26) 3-valerylamino-2-[N-{2'-(4",4"-dimethyloxazolin-2"-yl)biphenyl-4-yl}methyl]amino-4,6-dimethylpyridine
(27) 3-valerylamino-2-[N-{2'-(4",4"-dimethyloxazolin-2"-yl)biphenyl-4-yl}methyl]amino-5-bromo-4-methylpyridine
(28) 3-valerylamino-2-[N-{2'-(4",4"-dimethyloxazolin-2"-yl)biphenyl-4-yl}methyl]amino-5-bromo-4,6-dimethylpyridine Then, the 2-alkyl-3-(biphenyl-4-yl)methyl-6-halogeno-3H-imidazo[4,5-b]pyridine derivative (VII) is represented by the following general formula:

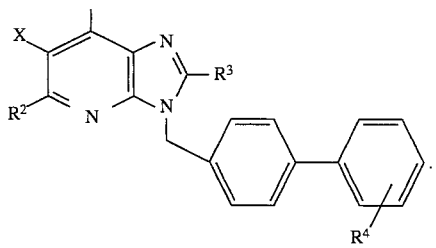

(VII)

In the formula, X represents a halogen atom; and $R^2$, $R^3$ and $R^4$ are each as defined above. Further, the halogen atom is a bromine atom or a chlorine atom. Furthermore, specific examples of the 2-alkyl-3-(biphenyl-4-yl)methyl-6-halogeno-3H-imidazo[4,5-b]-pyridine derivative (VII) according to the present invention include the following compounds, though the derivative (VII) is not limited to them.

(1) 2-cyclopropyl-3-(2'-methoxycarbonylbiphenyl-4-yl)methyl-6-bromo-7-methyl-3H-imidazo[4,5-b]pyridine
(2) 2-cyclopropyl-3-(2'-methoxycarbonylbiphenyl-4-yl)methyl-6-chloro-7-methyl-3H-imidazo[4,5-b]pyridine
(3) 2-cyclopropyl-3-(2'-methoxycarbonylbiphenyl-4-yl)methyl-6-bromo-5,7-dimethyl-3H-imidazo[4,5-b]-pyridine
(4) 2-cyclopropyl-3-(2'-methoxycarbonylbiphenyl-4-yl)methyl-6-chloro-5,7-dimethyl-3H-imidazo[4,5-b]-pyridine
(5) 2-n-propyl-3-(2'-methoxycarbonylbiphenyl-4-yl)methyl-6-bromo-7-methyl-3H-imidazo[4,5-b]pyridine
(6) 2-n-propyl-3-(2'-methoxycarbonylbiphenyl-4-yl)methyl-6-chloro-7-methyl-3H-imidazo[4,5-b]pyridine
(7) 2-n-propyl-3-(2'-methoxycarbonylbiphenyl-4-yl)methyl-6-bromo-5,7-dimethyl-3H-imidazo[4,5-b]-pyridine
(8) 2-n-propyl-3-(2'-methoxycarbonylbiphenyl-4-yl)methyl-6-chloro-5,7-dimethyl-3H-imidazo[4,5-b]-pyridine
(9) 2-n-butyl-3-(2'-methoxycarbonylbiphenyl-4-yl)methyl-6-bromo-7-methyl-3H-imidazo[4,5-b]pyridine
(10) 2-n-butyl-3-(2'-methoxycarbonylbiphenyl-4-yl)methyl-6-chloro-7-methyl-3H-imidazo[4,5-b]pyridine
(11) 2-n-butyl-3-(2'-methoxycarbonylbiphenyl-4-yl)methyl-6-bromo-5,7-dimethyl-3H-imidazo[4,5-b]pyridine
(12) 2-n-butyl-3-(2'-methoxycarbonylbiphenyl-4-yl)methyl-6-chloro-5,7-dimethyl-3H-imidazo[4,5-b]pyridine
(13) 2-ethyl-3-(2'-methoxycarbonylbiphenyl-4-yl)methyl-6-bromo-7-methyl-3H-imidazo[4,5-b]pyridine
(14) 2-ethyl-3-(2'-methoxycarbonylbiphenyl-4-yl)methyl-6-chloro-7-methyl-3H-imidazo[4,5-b]pyridine
(15) 2-ethyl-3-(2'-methoxycarbonylbiphenyl-4-yl)methyl-6-bromo-5,7-dimethyl-3H-imidazo[4,5-b]pyridine
(16) 2-ethyl-3-(2'-methoxycarbonylbiphenyl-4-yl)methyl-6-chloro-5,7-dimethyl-3H-imidazo[4,5-b]pyridine
(17) 2-cyclopropyl-3-[2'-(4",4"-dimethyloxazolin-2"-yl)biphenyl- 4-yl]methyl-6-bromo-7-methyl-3H-imidazo-[4,5-b]pyridine
(18) 2-cyclopropyl-3-[2'-(4",4"-dimethyloxazolin-2"-yl)biphenyl- 4-yl]methyl-6-chloro-7-methyl-3H-imidazo-[4,5-b]pyridine
(19) 2-cyclopropyl-3-[2'-(4",4"-dimethyloxazolin-2"-yl)biphenyl- 4-yl]methyl-6-bromo-5,7-dimethyl-3H-imidazo[4,5-b]pyridine
(20) 2-cyclopropyl-3-[2'-(4",4"-dimethyloxazolin-2"-yl)biphenyl- 4-yl]methyl-6-chloro-5,7-dimethyl-3H-imidazo[4,5-b]pyridine
(21) 2-n-propyl-3-[2'-(4",4"-dimethyloxazolin-2"-yl)biphenyl- 4-yl]methyl-6-bromo-7-methyl-3H-imidazo-[4,5-b]pyridine
(22) 2-n-propyl-3-[2'-(4",4"-dimethyloxazolin-2"-yl)biphenyl- 4-yl]methyl-6-chloro-7-methyl-3H-imidazo-[4,5-b]pyridine
(23) 2-n-propyl-3-[2'-(4",4"-dimethyloxazolin-2"-yl)biphenyl- 4-yl]methyl-6-bromo-5,7-dimethyl-3H-imidazo[4,5-b]pyridine
(24) 2-n-propyl-3-[2'-(4",4"-dimethyloxazolin-2"-yl)biphenyl- 4-yl]methyl-6-chloro-5,7-dimethyl-3H-imidazo[4,5-b]pyridine
(25) 2-n-butyl-3-[2'-(4",4"-dimethyloxazolin-2"-yl)biphenyl- 4-yl]methyl-6-bromo-7-methyl-3H-imidazo-[4,5-b]pyridine
(26) 2-n-butyl-3-[2'-(4",4"-dimethyloxazolin-2"-yl)biphenyl- 4-yl]methyl-6-chloro-7-methyl-3H-imidazo-[4,5-b]pyridine
(27) 2-n-butyl-3-[2'-(4",4"-dimethyloxazolin-2" yl)biphenyl-4-yl]methyl-6-bromo-5,7-dimethyl-3H-imidazo[4,5-b]pyridine
(28) 2-n-butyl-3-[2'-(4",4"-dimethyloxazolin-2"-yl)biphenyl- 4-yl]methyl-6-chloro-5,7-dimethyl-3H-imidazo-[4, 5-b]pyridine
(29) 2-ethyl-3-[2'-(4",4"-dimethyloxazolin-2"-yl)biphenyl-4-yl]methyl-6-bromo-7-methyl-3H-imidazo-[4,5-b]pyridine

(30) 2-ethyl-3-[2'-(4",4"-dimethyloxazolin-2"-yl)biphenyl-4-yl]methyl-6-chloro-7-methyl-3H-imidazo-[4,5-b]pyridine

(31) 2-ethyl-3-[2'-(4",4"-dimethyloxazolin-2"-yl)biphenyl-4-yl]methyl-6-bromo-5,7-dimethyl-3H-imidazo[4,5-b]pyridine

(32) 2-ethyl-3-[2'-(4",4"-dimethyloxazolin-2"-yl)biphenyl-4-yl]methyl-6-chloro-5,7-dimethyl-3H-imidazo[4,5-b]pyridine Then, the 2-[N-(biphenyl-4-yl)methyl]alkylamido- 3-nitropyridine derivative (VIII) is represented by the following general formula:

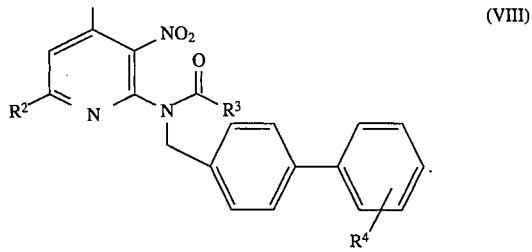

(VIII)

In the formula, $R^2$, $R^3$ and $R^4$ are each as defined above. Further, specific examples of the 2-[N-(biphenyl-4-yl)methyl]alkylamido-3-nitropyridine derivative (VIII) according to the present invention include the following compounds, though the derivative (VIII) is not limited to them.

(1) 2-[N-(2'-methoxycarbonylbiphenyl-4-yl)methyl]-cyclopropanecarboxamido-4-methyl-3-nitropyridine
(2) 2-[N-(2'-methoxycarbonylbiphenyl-4-yl)methyl]-cyclopropanecarboxamido-4,6-dimethyl-3-nitropyridine
(3) 2-[N-(2'-methoxycarbonylbiphenyl-4-yl)methyl]-butyrylamino-4-methyl-3-nitropyridine
(4) 2-[N-(2'-methoxycarbonylbiphenyl-4-yl)methyl]-butyrylamino-4,6-dimethyl-3-nitropyridine
(5) 2-[N-(2'-methoxycarbonylbiphenyl-4-yl)methyl]-valerylamino-4-methyl-3-nitropyridine
(6) 2-[N-(2'-methoxycarbonylbiphenyl-4-yl)methyl]-valerylamino-4,6-dimethyl-3-nitropyridine
(7) 2-[N-{2'-(4",4"-dimethyloxazolin-2"-yl) -biphenyl-4-yl}methyl]cyclopropanecarboxamido-4-methyl- 3-nitropyridine
(8) 2-[N-{2'-(4",4"-dimethyloxazolin-2"-yl)biphenyl-4-yl}methyl]cyclopropanecarboxamido-4,6-dimethyl-3-nitropyridine
(9) 2-[N-{2'-(4",4"-dimethyloxazolin-2"-yl)biphenyl-4-yl}methyl]butyrylamino-4-methyl-3-nitropyridine
(10) 2-[N-{2'-(4",4"-dimethyloxazolin-2"-yl)biphenyl-4-yl}methyl]butyrylamino-4,6-dimethyl-3-nitropyridine
(11) 2-[N-{2'-(4",4"-dimethyloxazolin-2"-yl)biphenyl-4-yl}methyl]valerylamino-4-methyl-3-nitropyridine
(12) 2-[N-{2'-(4",4"-dimethyloxazolin-2"-yl)biphenyl-4-yl}methyl]valerylamino-4,6-dimethyl-3-nitropyridine Then, the 2-alkylamido-5nitropyridine derivative (IX) is represented by the following general formula:

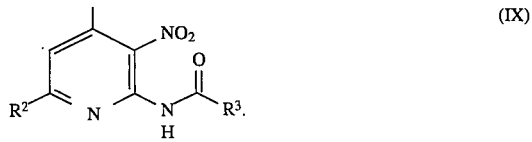

(IX)

In the formula, $R^2$ and $R^3$ are each as defined above. Further, specific examples of the 2-alkylamido- 3-nitropyridine derivative (IX) according to the present invention include the following compounds, though the derivative (IX) is not limited to them.

(1) 2-cyclopropanecarboxamido-4-methyl-3-nitropyridine
(2) 2,cyclopropanecarboxamido-4,6-dimethyl-3-nitropyridine
(3) 2-butyrylamino-4-methyl-3-nitropyridine
(4) 2-butyrylamino-4,6-dimethyl-3-nitropyridine
(5) 2-valerylamino-4-methyl-3-nitropyridine
(6) 2-valerylamino-4,6-dimethyl-3-nitropyridine Then, the steps constituting the process of the present invention will now be described in detail (see the above reaction scheme 4).

Step 1

This step is one wherein a 2-alkylamido-3-nitropyridine derivative (III) is obtained by reacting a 2-amino-3-nitropyridine derivative (V) with a compound represented by the general formulas $R^3COZ$ or $(R^3CO)_2O$ to conduct acid amidation. In this step, the amidation is conducted by using an acid chloride (Z=a halogen atom in the above general formula $R^3COZ$), a carboxylic acid (Z=OH in the same formula), a mixed acid anhydride (Z=an alkoxycarbonyl group, an aryloxy-carbonyl group or an aralkyloxycarbonyl group), an acid anhydride (the above general formula $(R^3CO)_2O$) or an active ester of a carboxylic acid with N-hydroxybenzotriazole or N-hydroxysuccinimide in the conventional manner.

Step 2

This step is one wherein the 2-alkylamido- 3-nitropyridine derivative (III) is subjected to N-alkylation with an active biphenyl derivative (IV) to prepare a 2-[N-(biphenyl-4-yl)methyl]alkylamido- 3-nitropyridine derivative (I).

Step 3

In this step, the 2-[N-(biphenyl-4-yl)methyl]alkylamido-3-nitropyridine derivative (I) is cyclized into a 2-alkyl-3-(biphenyl-4-yl)methyl-3H-imidazo-[4,5-b]pyridine derivative (II) under reducing conditions. As the catalyst and reducing agent to be used in this step, the following combination (a catalyst and a reducing agent), for example, can be cited specifically.

a) palladium-carbon (hereinafter referred to as "Pd-C"), amine and organic acid
b) Pd-C and hydrogen gas
c) sodium borohydride and cuptic chloride
d) Pd-C and sodium hypophosphite ($NaH_2PO_2$)
e) Pd-C, iron and acetic acid The Pd-C catalyst according to the present invention may be any one so far as it is generally used in catalytic reduction. The palladium content of the catalyst is generally 2 to 20%, preferably 5 to 10%. Further, the form of the catalyst is not limited, but may be a dry powder, a wet body or an aqueous slurry. The amount of the catalyst to be used is generally 0.001 to 10% by weight, preferably 0.01 to 5% by weight, still preferably 0.1 to 1% by weight based on the compound (I), though the amount is not limited.

The organic acid according to the present invention is a lower carboxylic acid having 1 to 6 carbon atoms and specific examples thereof include formic acid, acetic acid and propionic acid.

The amine according to the present invention may be any one, so far as it can form a salt together with an organic acid such as formic acid or acetic acid. Specific examples of the amine to be generally used include triethylamine, trimethylamine, tripropylamine, diethylamine, dimethylamine, dipropylamine, diisopropylamine, dibutylamine, N,N-dimethylethylamine, N,N-dimethylpropylamine, N,N-dimethylisopropylamine, N,N-dimethylbutylamine, N,N-dimethylhexylamine, N,N-dimethylcyclohexylamine, N,N-dimethyloctylamine, N,N-dimethyldodecylamine, N,N-dimethylbenzylamine, N,N-dimethyl-2-chloroethylamine, N,N-dimethyl- 2-chloropropylamine, 2-chlorotriethylamine, N,N-diethylmethylamine, N,N,N',N'-tetramethylmethanediamine, N,N,N',N'-tetramethylethylenediamine, N,N-dimethylaniline, N,N-dimethyltoluidine, N,N-diethylaniline, ethanolamine, diethanolamine, triethanolamine, N-methylethanolamine, N,N-dimethylethanolamine, pyridine, N-methylpiperidine, N-methylmorpholine, 1,4-dimethylpiperazine, N-methylpyrrole, N-methylpyrrolidine and ammonia. Among these amines, triethylamine, trimethylamine, tripropylamine, diethylamine and ethanolamine are preferable, and triethylamine is still preferable.

When triethylamine and formic acid are used as the reducing agents, the cyclization can be generally conducted according to the process described in Journal of Organic Chemistry (J. Org. Chem.), 42 (22), 3491 to 3494, 1977. According to the present invention, the amine is used generally in an amount of 1 to 150 equivalents, preferably 1.5 to 50 equivalents, still preferably 2 to 20 equivalents based on the compound (I), while the organic acid is used generally in an amount of 1 to 50 equivalents, preferably 1.5 to 20 equivalents, still preferably to 10 equivalents based on the compound (I).

Furthermore, according to the present invention, the reductive cyclization with a combination of a Pd-C catalyst with an amine and an organic acid may be conducted in the absence or presence of a solvent. Specific examples of the solvent to be used include, e.g., water, methanol, ethanol, n-propanol, i-propanol, butanol, tetrahydrofuran, 1,2-dimethoxyethane, diethyl ether, diisopropyl ether, methyl acetate, ethyl acetate, propyl acetate, methyl propionate, ethyl propionate, 1,4-dioxane, benzene, toluene, xylene, formic acid, acetic acid, propionic acid, diethylamine, triethylamine, tripropylamine, ethanolamine, n-hexane, n-octane and petroleum ether, among which water, methanol, ethanol, n-propanol, i-propanol, tetrahydrofuran, 1,2-dimethoxyethane, methyl acetate, ethyl acetate, propyl acetate, methyl propionate, ethyl propionate, formic acid, acetic acid, triethylamine and toluene are preferable, and water, methanol, ethanol, ethyl acetate, tetrahydrofuran, 1,2-dimethoxyethane, triethylamine and toluene are still preferable.

When the solvent is used, the amount thereof is generally 0.5 to 100 parts by volume, preferably 0.5 to 50 parts by volume, still preferably i to 20 parts by volume based on i part by weight of the compound (I), though the amount is not limited. The solvents may be used each alone or as a mixture of two or more of them.

The order of addition of the amine and the organic acid as the reducing agents is not limited. The amine may be added prior to the addition of the acid or the organic acid may be added prior to the addition of the amine. That is, the organic acid may be added to a suspension comprising the compound (I), the catalyst, the amine and, if necessary, a solvent, or the amine may be added to a suspension comprising the compound (I), the catalyst, the organic acid and, if necessary, a solvent.

The reaction temperature is not particularly limited. The reaction is generally conducted at from 0° C. to the refluxing temperature of the amine or solvent. Although the reaction time may be from about one minute to 48 hours, the reaction is generally completed in 30 minutes to 12 hours.

When hydrogen gas is used as the reducing agent, the cyclization can be carried out under the conditions employed conventionally in organic synthesis for catalytic reduction i.e., under the conditions of normal pressure (atmospheric pressure) to 150 kg/cm². This reaction is preferably conduted in a solvent and the kind and amount of the solvent and the temperature and time of the reaction may be the same as those described above for the case of using an amine and an organic acid as the reducing agents.

When sodium borohydride and cuptic chloride are used as the reducing agents, the amount of sodium borohydride to be used is generally about 1 to 100 equivalents, preferably 2 to 80 equivalents, still preferably 5 to 50 equivalents based on the compound. (I), though the amount is not limited. On the other hand, the amount of cuptic chloride to be used is generally 1 to 50 equivalents, preferably 2 to 30 equivalents, still preferably 5 to 20 equivalents based on the compound (I). This reaction is also preferably conducted in a solvent and the kind and amount of the solvent and the temperature and time of the reaction may be the same as those described above for the case of using an amine and an organic acid as the reducing agents.

When sodium hypophosphite is used as the reducing agent, the amount thereof is generally 1 to 100 equivalents, preferably 2 to 50 equivalents, still preferably 5 to 20 equivalents based on the compound (I), though the amount is not limited. This reaction is also preferably conducted in a solvent and the kind and amount of the solvent and the temperature and time of the reaction may be the same as those described above for the case of using an amine and an organic acid as the reducing agents.

When iron and acetic acid are used as the reducing agents, the amounts of them are not limited. The amount of iron used is generally 1 to 100 equivalents, preferably 5 to 75 equivalents, still preferably 10 to 50 equivalents based on the compound (I), while the amount of acetic acid used is generally 1 to 500 equivalents, preferably 10 to 300 equivalents, still preferably 50 to 200 equivalents based on the compound (I). When a solvent is used in this reaction, the kind and amount of the solvent to be used and the temperature and time of the reaction may be the same as those described above for the case of using an amine and an organic acid as the reducing agents, though this reaction may be carried out in the absence of any solvent.

Steps 4 and 5

In step 4, only the 5-position halogen atom of the pyridine ring in the 2-[N-(biphenyl-4-yl)methyl]alkylamido- 3-nitropyridine derivative (I) is selectively reduced, i.e.. replaced by a hydrogen atom, while in step 5, only the 5-position halogen atom of the pyridine ring in the 2-alkylamido-5-halogeno- 3-nitropyridine derivative (III) is selectively reduced, i.e., replaced by a hydrogen atom. These steps can be conducted by using the Pd-C catalyst and amine and organic acid as those described in explanation of step 3 as a combination of a catalyst and a reducing agent and by employing the same conditions as those of step 3 with respect to the solvent and reaction temperature. The reaction time is generally 5 minutes to 7 hours, preferably 30 minutes to 6 hours, still preferably 1 to 5 hours. Step 4 gives a 2-[N-(biphenyl-4-yl)methyl]alkylamido-3-nitropyridine derivative (VIII), while the step 5 gives a 2-alkylamido-3-nitropyridine derivative (IX).

Step 6

This step is one wherein a 2-[N-(biphenyl-4-yl)methyl] alkylamido-3-nitropyridine derivative (VIII) is prepared from the 2-alkylamido-3-nitropyridine derivative (IX) which has been prepared in the step 5 by replacing the halogen atom present at the 5-position of the pyridine ring with a hydrogen atom through N-alkylation, and can be conducted in the same manner as that of the step 2.

Step 7

This step is one wherein a 2-alkyl-3-(biphenyl-4-yl)methyl- 3H-imidazo[4,5-b]pyridine derivative (II) is prepared from the 2-[N-(biphenyl-4-yl)methyl]alkylamido- 3-nitropyridine derivative (VIII) which has been prepared in steps 4 or 6 and has a hydrogen atom at the 5-position through cyclization under reductive conditions.

In this step, the reductive cyclization can be conducted with the same combination of a catalyst and a reducing agent as that described above in explanation of step 3 under the same conditions as those described above in explanation of step 3. Alternatively, the reductive cyclization may be conducted by using any of the following reducing agents in the conventional manner:

a) iron and acetic acid
b) iron and hydrochloric acid

Step 8

This step is one wherein the 2-[N-(biphenyl-4-yl)methyl]alkylamido-3-nitropyridine derivative (I) is reductive isomerized with activated carbon, hydrazine and ferric chloride to form a 2-[N-(biphenyl-4-yl)methyl]amino-8-alkylamidopyridine derivative (VI). Although the amounts of activated carbon, hydrazine and ferric chloride used are not limited, activated carbon is generally used in an amount of 1 to 50% by weight, preferably 3 to 40% by weight, still preferably 5 to 30% by weight based on the compound (I); hydrazine generally in an amount of 1 to 50 equivalents, preferably 1.5 to 20 equivalents, still preferably 2 to 10 equivalents based on the compound (I): and ferric chloride generally in an amount of 1 to 50 equivalents, preferably 1.5 to 20 equivalents, still preferably 2 to 10 equivalents based on the compound (I). This step is preferably conducted in the presence of a solvent. The kind of the solvent and the reaction temperature may be the same as those of the case of using an amine and an organic acid in step 8. The reaction time is generally completed within 48 hours.

Step 9

This step is one wherein a 2-alkyl-8-(biphenyl-4-yl)methyl- 3H-imidazo[4,5-b]pyridine derivative is prepared from the 2-[N-(biphenyl-4-yl)methyl]amino-3-alkylamidopyridine derivative (VI) which has been prepared in step 8 through cyclization under acidic conditions. This reaction is not limited so far as it is conducted in the presence of any acid which is used in a conventional organic synthesis. The reaction is conducted with, for example, specifically, an inorganic acid such as hydrochloric acid, sulfuric acid, nitric acid, hydrobromic acid, hydroiodic acid, perchloric acid, phosphoric acid and polyphosphoric acid; or a sulfonic acid such as methanesulfonic acid, benzenesulfonic acid, p-toluenesulfonic acid and camphorsulfonic acid, under acidic conditions.

This step is also preferably conducted in the presence of a solvent. Specific examples of the solvent include tetrahydrofuran, 1,2-dimethoxyethane, diethyl ether, diisopropyl ether, methyl acetate, ethyl acetate, propyl acetate, methyl propionate, ethyl propionate, 1,4-dioxane, benzene, toluene, xylene, formic acid, acetic acid, propionic acid, n-hexane, n-octane and petroleum ether, among which tetrahydrofuran, 1,2-dimethoxyethane, formic acid, acetic acid, propionic acid, benzene, toluene and xylene are preferable, and formic acid, acetic acid, benzene, Toluene and xylene are still preferable. The solvent is generally used in an amount of 0.5 to 100 pares by volume, preferably 0.5 to 50 parts by volume, still preferably 1 to 20 parts by volume based on 1 part by weight of the compound (VI), though The amount thereof is not limited. The above solvents may be used each alone or as a mixture of two or more of them.

Further, though the reaction temperature is not particularly limited, The reaction is generally conducted at from 0° C. to the refluxing temperature of the amine or solvent.

Furthermore, in this step, the reaction can be accelerated by removing formed water from the reaction system by adding a dehydrating agent such as a molecular sieve or by forming an azeotropic mixture. In such a case, the reaction time is generally completed within 12 hours.

Step 10

This step is one wherein the 2-[N-(biphenyl-4-yl)methyl]alkylamido-3-nitropyridine derivative (I) having a substituent halogen atom at the 5-position is reductively cyclized without the elimination of the halogen atom. The reductive cyclization in this step may be conducted by the use of iron and acetic acid or iron and hydrochloric acid in the conventional manner.

Step 11

This step is one wherein the 2-alkyl- 3-(biphenyl-4-yl)methyl-6-halogeno-3H-imidazo[4,5-b]-pyridine derivative (VII), which is one of compounds prepared in step 10 and has a substituent halogen atom at the 6-position, is reductively dehalogenated into an objective 2-alkyl-3-(biphenyl-4-yl)methyl-3H-imidazo[4,5-b]pyridine derivative (II). This step may be conducted in the same manner as that of step 3.

Step 12

This step is one wherein the 2-[N-(biphenyl- 4-yl)methyl]amino-3-alkylamidopyridine derivative (VI) prepared in step 8 is reduced and dehalogenated into an objective 2-alkyl-3-(biphenyl-4-yl)methyl-3H-imidazo[4,5-b]pyridine derivative (II). This step may be conducted in the same manner as that of step 3.

Step 13

The imidazopyridine derivatives which is disclosed in Japanese Patent Publication-A Nos. 3- 95181 and 3-236377 and is useful as antagonists against angiotensin II receptor, include 2-cyclopropyl-3-(2'-carboxylbiphenyl-4-yl)-methyl-7-methyl-3H-imidazo[4,5-b]pyridine or the like and are compounds having a carboxyl group. To obtain these compounds, the ester group or the oxazoline group of 2-alkyl-3-(biphenyl-4-yl)methyl-3H-imidazo-[4,5-b]pyridine derivatives (II) (such as 2-cyclopropyl- 3-(2'-methoxycarbonylbiphenyl-4-yl)methyl-7-methyl- 3H-imidazo-[4,5-b] pyridine) prepared according to the process of the present invention is subjected to a conventional hydrolysis in the production of them. Among these imidazoline derivatives having a carboxyl group, one having a cyclopropyl group at the 2-position is particularly excellent in the antagonism against angiotensin II receptor and therefore is highly useful as an antihypertensive drug or a remedy for hemal lesions. According to the process for the preparation of a 2-alkyl-3-(biphenyl-4-yl)methyl-3H-imidazo[4,5-b]pyridine derivative (II) of the present invention, a precursor of such an-antagonist against angiotensin II receptor can be prepared.

Then, the 2-alkylamido-3-nitropyridine derivative (X) represented by the following general formula is a novel compound and is useful as an intermediate for the preparation of the 2-alkyl-3-(biphenyl-4-yl)methyl- 3H-imidazo[4,5-b]pyridine derivative (II):

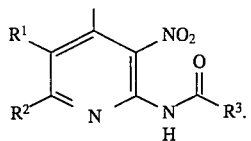

(X)

In the formula, $R^1$, $R^2$ and $R^3$ are each as defined above. $R^6$ represents a hydrogen atom or a group represented by the following general formula:

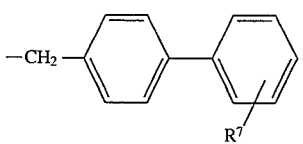

(wherein $R^7$ represents a group represented by the following general formula:

—COOR$^8$

{wherein $R^8$ represents a lower alkyl group, a cycloalkyl group, an alkoxyalkyl group, a thioalkoxyalkyl group, a cycloether group, an aryl group, an aralkyl group, an alkenyl group, an alkenyl group or a trialkylsilyl group} or a group represented by the following general formula:

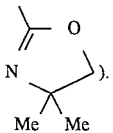

Specific examples of $R^8$ include the same groups as those described with respect to $R^5$ in the above 2-[N-(2'-biphenyl-4-yl)methyl]alkylamido-3-nitropyridine derivative (I). Further, specific examples of the 2-alkylamido- 3-nitropyridine derivative (X) according to the present invention include the following compounds, though the derivative (X) is not limited to them.

(1) 2-[N-(2'-methoxycarbonylbiphenyl-4-yl)methyl]-cyclopropanecarboxamido-4-methyl-3-nitropyridine
(2) 2-[N-(2'-methoxycarbonylbiphenyl-4-yl)methyl]-cyclopropanecarboxamido-4,6-dimethyl-3-nitropyridine
(3) 2-[N-(2'-methoxycarbonylbiphenyl-4-yl)methyl]-cyclopropanecarboxamido-5-bromo-4-methyl-3-nitropyridine
(4) 2-[N-(2'-methoxycarbonylbiphenyl-4-yl)methyl]-cyclopropanecarboxamido-5-chloro-4-methyl-3-nitropyridine
(5) 2-[N-(2'-methoxycarbonylbiphenyl-4-yl)methyl]-cyclopropanecarboxamido-5bromo-4,6-dimethyl-3-nitropyridine
(6) 2-[N-(2'-methoxycarbonylbiphenyl-4-yl)methyl]-cyclopropanecarboxamido-5chloro-4,6-dimethyl-3-nitropyridine
(7) 2-[N-(2'-methoxycarbonylbiphenyl-4-yl)methyl]-butyrylamino-4-methyl-3-nitropyridine
(8) 2-[N-(2'-methoxycarbonylbiphenyl-4-yl)methyl]-butyrylamino-4,6-dimethyl-3-nitropyridine
(9) 2-[N-(2'-methoxycarbonylbiphenyl-4-yl)methyl]-butyrylamino-5-bromo-4-methyl-3-nitropyridine
(10) 2-[N-(2'-methoxycarbonylbiphenyl-4-yl)methyl]-butyrylamino-5bromo-4,6-dimethyl-3-nitropyridine
(11) 2-[N-(2'-methoxycarbonylbiphenyl-4-yl)methyl]-valerylamino-4-methyl-3-nitropyridine
(12) 2-[N-(2'-methoxycarbonylbiphenyl-4-yl)methyl]-valerylamino-4,6-dimethyl-3-nitropyridine
(13) 2-[N-(2'-methoxycarbonylbiphenyl-4-yl)methyl]-valerylamino-5-bromo-4-methyl-3-nitropyridine
(14) 2-[N-(2'-methoxycarbonylbiphenyl-4-yl)methyl]-valerylamino-5bromo-4,6-dimethyl-3-nitropyridine
(15) 2-[N-{2'-(4",4"-dimethyloxazolin-2"-yl)biphenyl-4-yl}methyl]cyclopropanecarboxamido-4-methyl-3-nitropyridine
(16) 2-[N-{2'-(4",4"-dimethyloxazolin-2"-yl)biphenyl-4-yl}methyl]cyclopropanecarboxamido-4,8-dimethyl-3-nitropyridine
(17) 2-[N-{2'-(4",4"-dimethyloxazolin-2"-yl)biphenyl-4-yl}methyl]cyclopropanecarboxamido-5-bromo-4-methyl- 3-nitropyridine
(18) 2-[N-{2'-(4",4"-dimethyloxazolin-2"-yl)biphenyl-4-yl}methyl]cyclopropanecarboxamido-5-chloro-4-methyl- 3-nitropyridine
(19) 2-[N-{2'-(4",4"-dimethyloxazolin-2"-yl)biphenyl-4-yl}methyl]cyclopropanecarboxamido-5-bromo-4,6-dimethyl- 3-nitropyridine
(20) 2-[N-{2'-(4",4"-dimethyloxazolin-2"-yl)biphenyl-4-yl}methyl]cyclopropanecarboxamido-5-chloro-4,6-dimethyl- 3-nitropyridine
(21) 2-[N-{2'-(4",4"-dimethyloxazolin-2"-yl)biphenyl-4-yl}methyl]butyrylamino-4-methyl-3-nitropyridine
(22) 2-[N-{2'-(4",4"-dimethyloxazolin-2"-yl)biphenyl-4-yl}methyl]butyrylamino-4,6-dimethyl-3-nitropyridine
(23) 2-[N-{2'-(4",4"-dimethyloxazolin-2"-yl)biphenyl-4-yl}methyl]butyrylamino-5-bromo-4-methyl-3-nitropyridine
(24) 2-[N-{2'-(4",4"-dimethyloxazolin-2"-yl)biphenyl-4-yl}methyl]butyrylamino-5-bromo-4,6-dimethyl-3-nitropyridine
(25) 2-[N-{2'-(4",4"-dimethyloxazolin-2"-yl)biphenyl-4-yl}methyl]valerylamino-4-methyl-3-nitropyridine
(26) 2-[N-{2'-(4",4"-dimethyloxazolin-2"-yl)biphenyl-4-yl}methyl]valerylamino-4,6-dimethyl-3-nitropyridine
(27) 2-[N-{2'-(4",4"-dimethyloxazolin-2"-yl)biphenyl-4-yl}methyl]valerylamino-5-bromo-4-methyl-3-nitropyridine
(28) 2-[N-{2'-(4",4"-dimethyloxazolin-2"-yl)biphenyl-4-yl}methyl]valerylamino-5-bromo-4,6-dimethyl-3-nitropyridine
(29) 2-cyclopropanecarboxamido-4-methyl-3-nitropyridine
(30) 2-cyclopropanecarboxamido-4,6-dimethyl-3-nitropyridine
(31) 2-cyclopropanecarboxamido-5-bromo-4-methyl-3-nitropyridine
(32) 2-cyclopropanecarboxamido-5-chloro-4-methyl-3-nitropyridine
(33) 2-cyclopropanecarboxamido-5-bromo-4,5-dimethyl-3-nitropyridine
(34) 2-cyclopropanecarboxamido-5-chloro-4,6-dimethyl-3-nitropyridine
(35) 2-butyrylamino-4-methyl-3-nitropyridine
(36) 2-butyrylamino-4,6-dimethyl-3-nitropyridine
(37) 2-butyrylamino-5-bromo-4-methyl-3-nitropyridine
(38) 2-butyrylamino-5-bromo-4,6-dimethyl-3-nitropyridine
(39) 2-valerylamino-4-methyl-3-nitropyridine
(40) 2-valerylamino-4,6-dimethyl-3-nitropyridine
(41) 2-valerylamino-5-bromo-4-methyl-3-nitropyridine
(42) 2-valerylamino-5-bromo-4,6-dimethyl-3-nitropyridine The 2-[N-(biphenyl-4-yl)methyl]amino-3-alkylamidopyridine derivative (VI) represented by the following general formula is also a novel compound and is useful as an intermediate for the preparation of the 2-alkyl-3-(biphenyl-4-yl)methyl-3H-imidazo[4,5-b]-pyridine derivative (II):

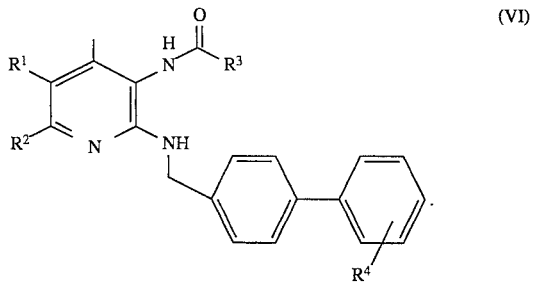

In the formula, $R^1$, $R^2$, $R^3$ and $R^4$ are each as defined above. Further, specific examples of the 2-[N-(biphenyl-4-yl)methyl]amino-3-alkylamidopyridine derivative (VI) according to the present invention include the following compounds, though the derivative (VI) is not limited to them.

(1) 3-cyclopropanecarboxamido-2-[N-(2'-methoxycarbonylbiphenyl- 4-yl)methyl]amino-4-methylpyridine
(2) 8-cyclopropanecarboxamido-2-[N-(2'-methoxycarbonylbiphenyl- 4-yl)methyl]amino-4,6-dimethylpyridine
(3) 8-cyclopropanecarboxamido-2-[N-(2'-methoxycarbonylbiphenyl- 4-yl)methyl]amino-5-bromo-4-methylpyridine
(4) 3-cyclopropanecarboxamido-2-[N-(2'-methoxycarbonylbiphenyl- 4-yl)methyl]amino-5-chloro-4-methylpyridine
(5) 3-cyclopropanecarboxamido-2-[N-(2'-methoxycarbonylbiphenyl- 4-yl)methyl]amino-5-bromo-4,6-dimethylpyridine
(6) 3-cyclopropanecarboxamido-2-[N-(2'-methoxycarbonylbiphenyl- 4-yl)methyl]amino-5-chloro-4,6-dimethylpyridine
(7) 3-butyrylamino-2-[N-(2'-methoxycarbonylbiphenyl-4-yl)methyl]amino-4-methylpyridine
(8) 3-butyrylamino-2-[N-(2'-methoxycarbonylbiphenyl-4-yl)methyl]amino-4,6-dimethylpyridine
(9) 3-butyrylamino-2-[N-(2'-methoxycarbonylbiphenyl-4 -yl)methyl]amino-5-bromo-4-methylpyridine
(10) 3-butyrylamino-2-[N-(2'-methoxycarbonylbiphenyl-4-yl)methyl]amino-5bromo-4,6-dimethylpyridine
(11) 3-valerylamino-2-[N-(2'-methoxycarbonylbiphenyl-4-yl)methyl]amino-4-methylpyridine
(12) 3-valerylamino-2-[N-(2'-methoxycarbonylbiphenyl-4-yl)methyl]amino-4,6-dimethylpyridine
(13) 3-valerylamino-2-[N-(2'-methoxycarbonylbiphenyl-4-yl)methyl]amino-5bromo-4-methylpyridine
(14) 3-valerylamino-2-[N-(2'-methoxycarbonylbiphenyl-4-yl)methyl]amino-5-bromo-4,6-dimethylpyridine
(15) 3-cyclopropanecarboxamido-2-[N-{2'-(4",4"-dimethyloxazolin-2"-yl)biphenyl-4-yl}methyl]amino-4-methylpyridine
(16) 3-cyclopropanecarboxamido-2-[N-{2'-(4",4"-dimethyloxazolin-2"-yl)biphenyl-4-yl}methyl]amino-4,6-dimethylpyridine
(17) 3-cyclopropanecarboxamido-2-[N-{2'-(4",4"-dimethyloxazolin- 2"-yl)biphenyl-4-yl}methyl]amino-5-bromo-4-methylpyridine
(18) 3-cyclopropanecarboxamido-2-[N-{2'-(4",4"-dimethyloxazolin-2"-yl)biphenyl-4-yl}methyl]amino-5-chloro-4-methylpyridine
(19) 3-cyclopropanecarboxamido-2-[N-{2'-(4",4"dimethyloxazolin- 2"-yl)biphenyl-4-yl}methyl]amino-5 -bromo-4,6-dimethylpyridine
(20) 3-cyclopropanecarboxamido-2-[N-{2'-(4",4"-dimethyloxazolin- 2"-yl)biphenyl-4-yl}-methylamino-5-chloro-4,6-dimethylpyridine
(21) 3-butyrylamino-2-[N-{2'-(4",4"-dimethyloxazolin-2"-yl)biphenyl-4-yl}methyl]amino-4-methylpyridine
(22) 3-butyrylamino-2-[N-{2'-(4",4"-dimethyloxazolin-2"-yl)biphenyl-4-yl}methyl]amino-4,6-dimethylpyridine
(23) 3-butyrylamino-2-[N-{2'-(4",4"-dimethyloxazolin-2"-yl)biphenyl-4-yl}methyl]amino-5bromo-4-methylpyridine
(24) 3-butyrylamino-2-[N-{2'-(4",4"-dimethyloxazolin-2"-yl)biphenyl-4-yl}methyl]amino-5-bromo-4,6-dimethylpyridine
(25) 3-valerylamino-2-[N-{2'-(4",4"-dimethyloxazolin-2"-yl)biphenyl-4-yl}methyl]amino-4-methylpyridine
(26) 3-valerylamino-2-[N-{2'-(4",4"-dimethyloxazolin-2"-yl)biphenyl-4-yl}methyl]amino-4,6-dimethylpyridine
(27) 3-valerylamino-2-[N-{2'-(4",4"-dimethyloxazolin-2"-yl)biphenyl-4-yl}methyl]amino-5-bromo-4-methylpyridine
(28) 3-valerylamino-2-[N-{2'-(4",4"-dimethyloxazolin-2"-yl)biphenyl-4-yl}methyl]amino-5-bromo-4,6-dimethylpyridine Compounds in which $R^4$ represents —$COOR^5$ and is present at 2'-position of the biphenyl in the above description, and the application of the process according to the present invention in the production of the compounds are particularly preferably.

Then, the present inventors have extensively studied for solving the problems of the process of the prior art. As a result, they have found that the above object can be attained by employing any of the following processes to enable an industrially preparation of a 2-alkyl-3-(2'-cyanobiphenyl-4-yl)methyl- 3H-imidazo[4,5-b]pyridine derivative (II), and have accomplished the present invention.

(1) subjecting a 2-[N-(2'-cyanobiphenyl-4-yl)methyl]-alkylamido-5-halogeno-3-nitropyridine derivative (I) to cyclization and dehalogenation under reducing conditions.

(2) reacting a 2-alkylamido-5-halogeno-3-nitropyridine derivative (III) with an active biphenyl derivative (IV) to form a 2-[N-(2'-cyanobiphenyl-4-yl)methyl]alkylamido-5-halogeno-3-nitropyridine derivative (I) through N-alkylation and then subjecting it to cyclization and dehalogenation under reducing conditions.

(3) reacting a 2-amino-5-halogeno-3-nitropyridine derivative (V) with a compound represented by the general formula: $R^2COZ$ or $(R^2CO)_2O$ to form a 2-alkylamido-5halogeno-3-nitropyridine derivative (III), reacting it with an active biphenyl derivative (IV) to form a 2-[N-(2'-cyanobiphenyl-4-yl)methyl]-alkylamido- 5-halogeno-3-nitropyridine derivative (I) through N-alkylation, and then subjecting it to cyclization and dehalogenation under reducing conditions.

(4) subjecting a 2-alkyl-3-(2'-cyanobiphenyl-4-yl)methyl-6-halogeno-3H-imidazo[4,5-b]pyridine derivative (VI) to reductive dehalogenation.

(5) subjecting a 2-[N-(2'-cyanobiphenyl-4-yl)methyl] alkylamido-5halogeno-3-nitropyridine derivative (I) to reductive cyclization with iron and acetic acid or iron and hydrochloric acid to form a 2-alkyl- 3-(2'-cyanobiphenyl-4-yl)methyl-6-halogeno-3H-imidazo[4,5-b]pyridine derivative (VI) and then subjecting it to reductive dehalogenation.

(6) cyclizing a 2-[N-(2'-cyanobiphenyl-4-yl)methyl]-amino- 5-halogeno-3-alkylamidopyridine derivative (VII) under acidic conditions into a 2-alkyl-8-(2'-cyanobiphenyl-4-yl)methyl-6-halogeno-3H-imidazo[4,5-b]-pyridine derivative (VI), and then subjecting it to reductive dehalogenation.

(7) subjecting to a 2-[N-(2'-cyanobiphenyl-4-yl) -methyl] alkylamido-5-halogeno-3-nitropyridine derivative (I) to reductive isomerization with activated carbon, hydrazine and ferric chloride to form a 2-[N-(2'-cyanobiphenyl-4-yl)methyl]amino-5-halogeno- 3-alkylamidopyridine derivative (VII), then cyclizing it under acidic conditions into a 2-alkyl-3-(2'-cyanobiphenyl-4-yl)methyl-6-halogeno-3H-imidazo-[4,5-b]pyridine derivative (VI), and further conducting reduction.

(8) subjecting a 2-[N-(2'-cyanobiphenyl-4-yl)methyl]-alkylamido- 5-halogeno-3-nitropyridine derivative (I) to selective reductive dehalogenation to form a 2-[N-(2'-cyanobiphenyl-4-yl)methyl]alkylamido-3-nitropyridine derivative (VIII) and then cyclizing it under reducing conditions.

(9) subjecting a 2-[N-(2'-cyanobiphenyl-4-yl)methyl]-amino- 5-halogeno-3-alkylamidopyridine derivative (VII) to cyclization and dehalogenation under reducing conditions.

(10) subjecting a 2-[N-(2'-cyanobiphenyl-4-yl)methyl] alkylamido-5-halogeno-3-nitropyridine derivative (I) to reductive isomerization with activated carbon, hydrazine and ferric chloride to form a 2-[N-(2'-cyanobiphenyl-4-yl)methyl]amino-5-halogeno- 3-alkylamidopyridine derivative (VII) and then subjecting it to cyclization and dehalogenation under reducing conditions.

Furthermore, according to the present invention the 5-position halogen atom can be eliminated and replaced by a hydrogen atom simultaneously with the reductive cyclization of the final step, so that the process of the present invention can dispense with the additional, industrially disadvantageous dehalogenation step with n-butyllithium unlike the process of the Japanese Patent Publication-A No. 3-95181, thus being extremely excellent. Alternatively, the dehalogenation may be selectively conducted prior to the reductive cyclization of the compound (I). The outline of the reaction path according to the present invention is represented by the following chemical reaction formula (reaction scheme-5):

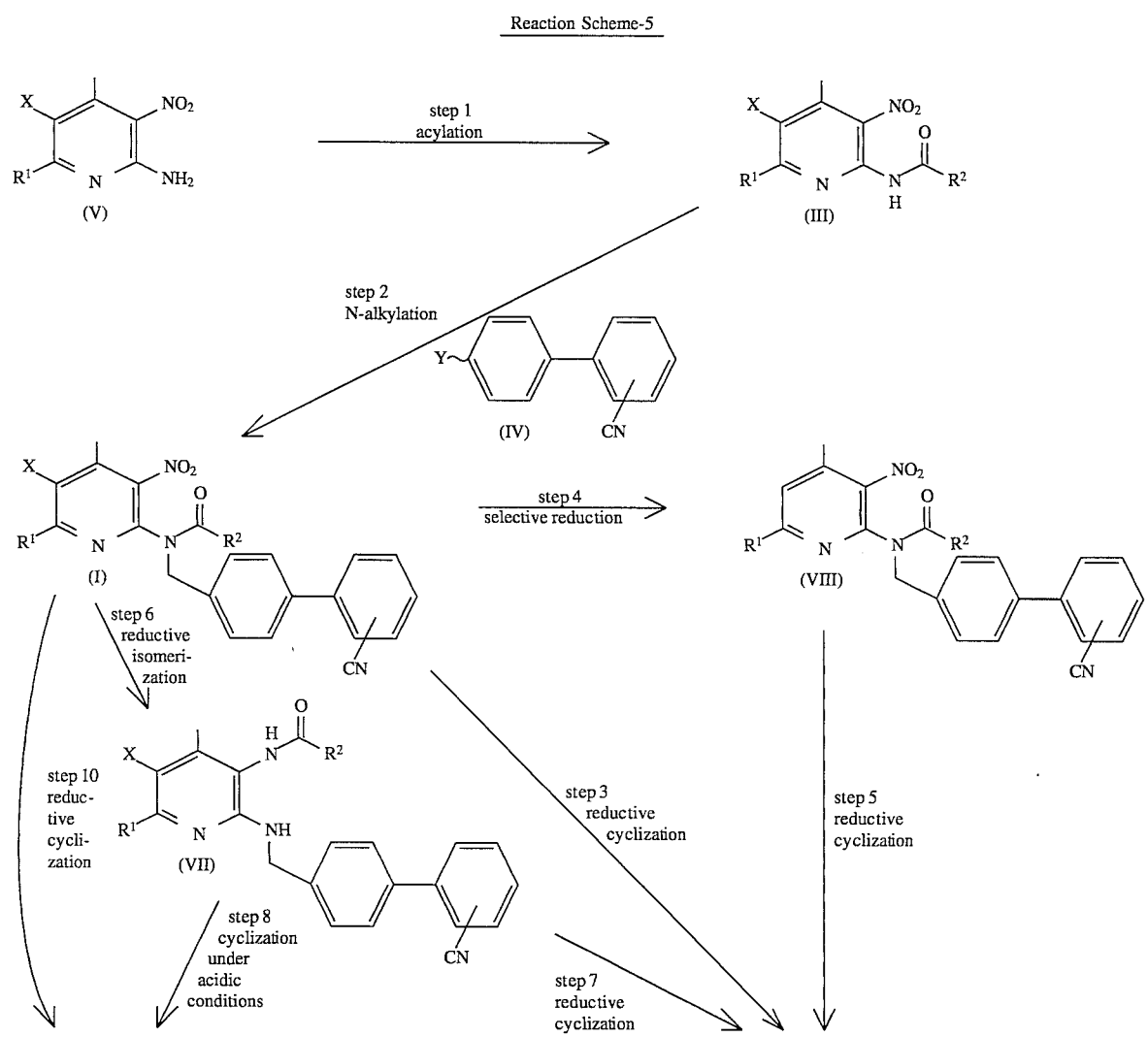

Reaction Scheme-5

-continued
Reaction Scheme-5

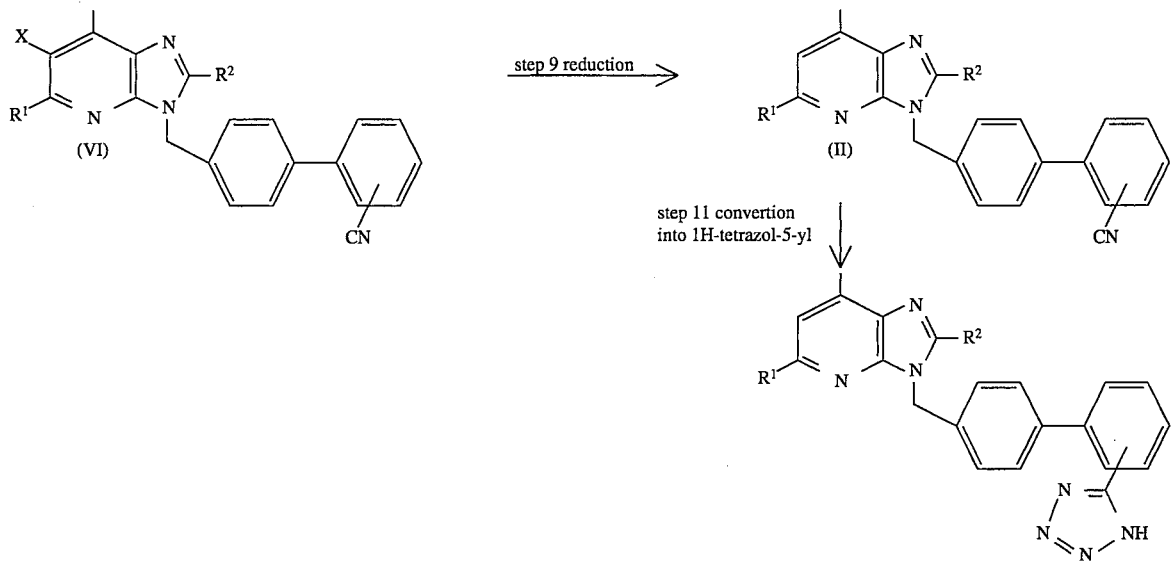

Accordingly, an object of the present invention is to provide an industrially advantageous process for preparing a 2-alkyl-3-(2'-cyanobiphenyl-4-yl)methyl-3H-imidazo[4,5-b]pyridine derivative (II) which is a precursor of an antagonist against angiotensin II receptor useful as an antihypertensive drug or a remedy for hemal lesions.

The 2-amino-5-halogeno-3-nitropyridine derivative (V) to be used as the starting material in step 1 (see the above reaction scheme-5, the same applies hereinafter) according to the present invention is represented by the following chemical structural formula:

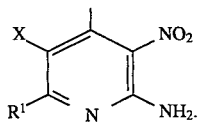
(V)

In the formula, X represents a halogen atom; and $R^1$ represents a hydrogen atom or a methyl group, with the proviso that the halogen atom is a bromine atom or a chlorine atom. Specific examples of the derivative (V) include the following compounds.

(1)  2-amino-5-bromo-4-methyl-3-nitropyridine  (2) 2-amino-5-chloro-4-methyl-3-nitropyridine
(3) 2-amino-5-bromo-4,6-dimethyl-3-nitropyridine
(4) 2-amino-5-chloro-4,6-dimethyl-3-nitropyridine The derivative (V) can be prepared by converting a 2-aminopyridine derivative into a 2-amino-5-bromopyridine derivative or a 2-amino-5-chloropyridine derivative through bromination or chlorination according to the process described in Journal of American Chemical Society (J.A.C.S.), 79, 6421 to 6426, 1957 or Journal of Organic Chemistry (J. Org. Chem.), 24, 1455 to 1460, 1959 and nitrating the obtained 5-halogenopyridine derivative in the conventional manner.

The 2-alkylamido-5-halogeno-3-nitropyridine derivative (III) obtained by conducting step 1 is represented by the following chemical structural formula:

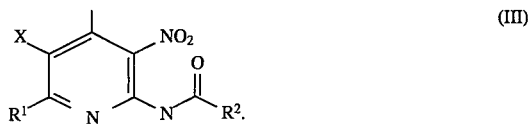
(III)

In the formula, $R^1$ and X are each as defined above and $R^2$ represents a cycloalkyl group, a lower alkyl group or a lower alkoxy group. Specific examples of cycloalkyl groups in the definition of $R^2$ include a cyclopropyl group, a cyclobutyl group, a cyclopentyl group and a cyclohexyl group; those of lower alkyl groups include alkyl groups having 1 to 6 carbon atoms, e.g., a methyl group, an ethyl group, a n-propyl group, an i-propyl group, a n-butyl group, an i-butyl group, a t-butyl group, an amyl group and a hexyl group; and those of lower alkoxy groups include lower alkoxy groups having 1 to 6 carbon atoms, e.g., a methoxy group, an ethoxy group, a n-propoxy group, an i-propoxy group, a butoxy group, a pentyloxy group and a hexyloxy group. Further, specific examples of the 2-alkylamido-5-halogeno-3-nitropyridine derivative (III) according to the present invention include the following compounds though the derivative (III) is not limited to them.

(1) 2-cyclopropanecarboxamido-5-bromo-4-methyl-3-nitropyridine
(2) 2-cyclopropanecarboxamido-5bromo-4,6-dimethyl-3-nitropyridine
(3) 2-cyclopropanecarboxamido-5chloro-4-methyl-3-nitropyridine
(4) 2-cyclopropanecarboxamido-5-chloro-4,6-dimethyl-3-nitropyridine
(5) 2-n-butyrylamino-5-bromo-4-methyl-3-nitropyridine
(6) 2-n-butyrylamino-5-bromo-4,6-dimethyl-3-nitropyridine
(7) 2-n-butyrylamino-5-chloro-4-methyl-3-nitropyridine
(8) 2-n-butyrylamino-5-chloro-4,6-dimethyl-3-nitropyridine
(9) 2-n-valerylamino-5-bromo-4-methyl-3-nitropyridine
(10) 2-n-valerylamino-5-bromo-4,6-dimethyl-3-nitropyridine

(11) 2-n-valerylamino-5-chloro-4-methyl-3-nitropyridine
(12) 2-n-valerylamino-5-chloro-4,6-dimethyl-3-nitropyridine The 2-[N-(2'-cyanobiphenyl-4-yl)methyl]alkylamido-5-halogeno-3-nitropyridine derivative (I) obtained as the result of step 2 has the following chemical structural formula:

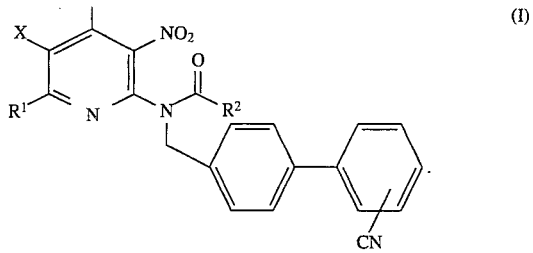

In the formula, $R^1$, $R^2$ and X are each as defined above. Furthermore, specific, representative examples of the compound (I) according to the present invention include, e.g., the following compounds, though the compound (I) is not limited to them.

(1) 2-[N-(2 -cyanobiphenyl-4-yl)methyl]cyclopropanecarboxamido- 5-bromo-4-methyl-3-nitropyridine
(2) 2-[N-(2 -cyanobiphenyl-4-yl)methyl]cyclopropanecarboxamido- 5-bromo-4,6-dimethyl-3-nitropyridine
(3) 2-[N-(2 -cyanobiphenyl-4-yl)methyl]cyclopropanecarboxamido- 5-chloro-4-methyl-3-nitropyridine
(4) 2-[N-(2 -cyanobiphenyl-4-yl)methyl]cyclopropanecarboxamido- 5-chloro-4,6-dimethyl-3-nitropyridine
(5) 2-[N-(2 -cyanobiphenyl-4-yl)methyl]butyrylamino- 5-bromo-4-methyl-3-nitropyridine
(6) 2-[N-(2 -cyanobiphenyl-4-yl)methyl]butyrylamino- 5-bromo-4,6-dimethyl-3-nitropyridine
(7) 2-[N-(2 -cyanobiphenyl-4-yl)methyl]butyrylamino-5-chloro-4,6-dimethyl-3-nitropyridine
(8) 2-[N-(2'-cyanobiphenyl-4-yl)methyl]butyrylamino-5-chloro-4-methyl-3-nitropyridine
(9) 2-[N-(2'-cyanobiphenyl-4-yl)methyl]valerylamino-5-bromo-4-methyl-3-nitropyridine
(10) 2-[N-(2'-cyanobiphenyl-4-yl)methyl]valerylamino-5-bromo-4,6-dimethyl-3-nitropyridine
(11) 2-[N-(2'-cyanobiphenyl-4-yl)methyl]valerylamino-5-chloro-4-methyl-3-nitropyridine
(12) 2-[N-(2'-cyanobiphenyl-4-yl)methyl]valerylamino-5-chloro-4,6-dimethyl-3-nitropyridine Then, the 2-[N-(2'-cyanobiphenyl-4-yl)methyl]-alkylamido- 3-nitropyridine derivative (VIII) obtained as the result of step 4 has the following chemical structural formula:

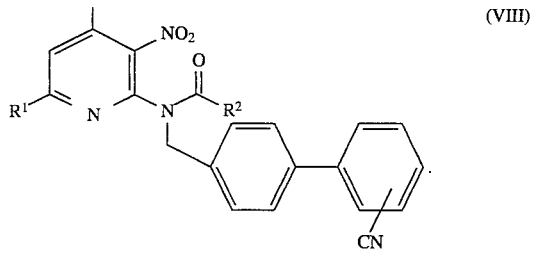

In the formula, $R^1$ and $R^2$ are each as defined above. Further specific and representative examples of the compound (VIII) according to the present invention include the following compounds, though the compound (VIII) is not limited to them.

(1) 2-[N-(2'-cyanobiphenyl-4-yl)methyl]cyclopropanecarboxamido- 4-methyl-3-nitropyridine
(2) 2-[N-(2'-cyanobiphenyl-4-yl)methyl]cyclopropanecarboxamido- 4,6-dimethyl-3-nitropyridine
(3) 2-[N-(2'-cyanobiphenyl-4-yl)methyl]cyclopropanecarboxamido- 4-methyl-3-nitropyridine
(4) 2-[N-(2'-cyanobiphenyl-4-yl)methyl]cyclopropanecarboxamido- 4,6-dimethyl-3-nitropyridine
(5) 2-[N-(2'-cyanobiphenyl-4-yl)methyl]butyrylamino-4-methyl-3-nitropyridine
(6) 2-[N-(2'-cyanobiphenyl-4-yl)methyl]butyrylamino- 4,6-dimethyl-3-nitropyridine
(7) 2-[N-(2'-cyanobiphenyl-4-yl)methyl]butyrylamino-4-methyl-3-nitropyridine
(8) 2-[N-(2'-cyanobiphenyl-4-yl)methyl]butyrylamino- 4,6-dimethyl-3-nitropyridine
(9) 2-[N-(2'-cyanobiphenyl-4-yl)methyl]valerylamino-4methyl-3-nitropyridine
(10) 2-[N-(2'-cyanobiphenyl-4-yl)methyl]valerylamino-4,6-dimethyl-3-nitropyridine
(11) 2-[N-(2'-cyanobiphenyl-4-yl)methyl]valerylamino-4-methyl-3-nitropyridine
(12) 2-[N-(2'-cyanobiphenyl-4-yl)methyl]valerylamino-4,6-dimethyl-3-nitropyridine Then, the 2-[N-(2'-cyanobiphenyl-4-yl)methyl]-amino-5-halogeno-3-alkylamidopyridine derivative (VII) obtained as the result of step 6 has the following chemical structural formula:

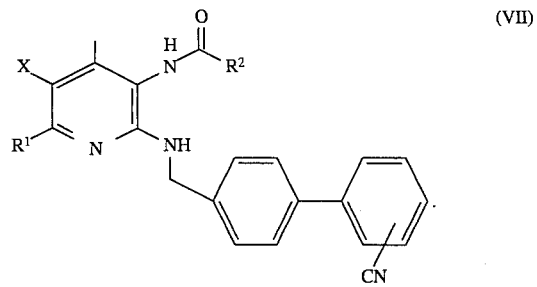

In the formula, $R^1$, $R^2$ and X are each as defined above. Further specific and representative examples of the compound (VII) according to the present invention include the following compounds, though the compound (VII) is not limited to them (1) 3-cyclopropanecarboxamido-2-[N-(2'-cyanobiphenyl-4-yl)methyl]amino-5-bromo-4-methylpyridine
(2) 3-cyclopropanecarboxamido-2-[N-(2'-cyanobiphenyl-4-yl)methyl]amino-5-bromo-4,6-dimethylpyridine
(3) 3-cyclopropanecarboxamido-2-[N-(2'-cyanobiphenyl-4-yl)methyl]amino-5-chloro-4-methylpyridine
(4) 3-cyclopropanecarboxamido-2-[N-(2'-cyanobiphenyl-4-yl)methyl]amino-5-chloro-4,6-dimethylpyridine
(5) 3-n-butyrylamino-2-[N-(2'-cyanobiphenyl-4-yl)methyl] amino-5-bromo-4-methylpyridine
(6) 3-n-butyrylamino-2-[N-(2'-cyanobiphenyl-4-yl)methyl] amino-5-bromo-4,6-dimethylpyridine
(7) 3-n-butyrylamino-2-[N-(2'-cyanobiphenyl-4-yl) -methyl]amino-5-chloro-4-methylpyridine
(8) 3-n-butyrylamino-2-[N-(2'-cyanobiphenyl-4-yl)-methyl]amino-5-chloro-4,6-dimethylpyridine
(9) 3-n-valerylamino-2-[N-(2'-cyanobiphenyl-4-yl)-methyl]amino-5-bromo-4-methylpyridine
(10) 3-n-valerylamino-2-[N-(2'-cyanobiphenyl-4-yl)-methyl]amino-5-bromo-4,6-dimethylpyridine
(11) 3-n-valerylamino-2-[N-(2'-cyanobiphenyl-4-yl)-methyl]amino-5-chloro-4-methylpyridine
(12) 3-n-valerylamino-2-[N-(2'-cyanobiphenyl-4-yl)-methyl]amino-5-chloro-4,6-dimethylpyridine Then, the 2-alkyl-5-(2'-cyanobiphenyl-4-yl)methyl-6-halogeno-3H-imidazo[4,5-b]pyridine derivative (VI) obtained by conducting steps 8 or 10 has the following structural formula:

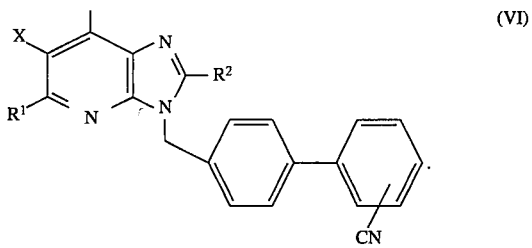

In the formula, $R^1$, $R^2$ and X are each as defined above. Further specific and representative examples of the compound (VI) according to the present invention include the following compounds, though the compound (VI) is not limited to them.

(1) 2-cyclopropyl-3-(2'-cyanobiphenyl-4-yl)methyl-6-bromo- 7-methyl-3H-imidazo[4,5-b]pyridine
(2) 2-cyclopropyl-8-(2'-cyanobiphenyl-4-yl)methyl-6-bromo- 5,7-dimethyl-3H-imidazo[4,5-b]pyridine
(3) 2-n-propyl-3-(2'-cyanobiphenyl-4-yl)methyl-6-bromo-7-methyl-3H-imidazo[4,5-b]pyridine
(4) 2-n-propyl-3-(2'-cyanobiphenyl-4-yl)methyl-5-bromo-5,7-dimethyl-3H-imidazo[4,5-b]pyridine
(5) 2-n-butyl-3-(2'-cyanobiphenyl-4-yl)methyl-6-bromo-7-methyl-3H-imidazo[4,5-b]pyridine
(6) 2-n-butyl-3-(2'-cyanobiphenyl-4-yl)methyl-6-bromo-5,7-dimethyl-3H-imidazo[4,5-b]pyridine
(7) 2-ethyl-3-(2'-cyanobiphenyl-4-yl)methyl-6-bromo-7-methyl-3H-imidazo[4,5-b]pyridine
(8) 2-ethyl-3-(2'-cyanobiphenyl-4-yl)methyl-6-bromo- 5,7-dimethyl-3H-imidazo[4,5-b]pyridine Further, the 2-alkyl-3-(2'-cyanobiphenyl-4-yl)methyl-3H-imidazo[4,5-b]pyridine derivative (II) obtained by conducting steps 8, 5, 7 or 9 is represented by the following chemical structural formula:

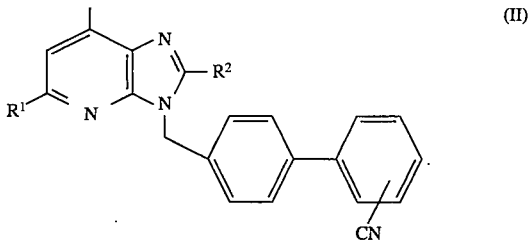

In the formula, $R^1$ and $R^2$ are each as defined above. Further, specific and representative examples of the compound (II) according to the present invention include the following compounds, though the compound (II) is not limited to them.

(1) 2-cyclopropyl-3-(2'-cyanobiphenyl-4-yl)methyl-7-methyl- 3H-imidazo[4,5-b]pyridine
(2) 2-cyclopropyl-3-(2'-cyanobiphenyl-4-yl)methyl- 5,7-dimethyl-3H-imidazo[4,5-b]pyridine
(3) 2-n-propyl-3-(2'-cyanobiphenyl-4-yl)methyl-7-methyl-3H-imidazo[4,5-b]pyridine
(4) 2-n-propyl-3-(2'-cyanobiphenyl-4-yl)methyl-5,7-dimethyl- 3H-imidazo[4,5-b]pyridine
(5) 2-n-butyl-3-(2'-cyanobiphenyl-4-yl)methyl-7-methyl-3H-imidazo[4,5-b]pyridine
(6) 2-n-butyl-3-(2'-cyanobiphenyl-4-yl)methyl-5,7-dimethyl- 3H-imidazo[4,5-b]pyridine
(7) 2-ethyl-3-(2'-cyanobiphenyl-4-yl)methyl-7-methyl-3H-imidazo[4,5-b]pyridine
(8) 2-ethyl-3-(2'-cyanobiphenyl-4-yl)methyl-5,7-dimethyl-3H-imidazo[4,5-b]pyridine Next, each step of the process according to the present invention will be described in detail hereinafter (see the above reaction scheme-5).

Step 1

This step is one wherein a 2-amino-5-halogeno-3-nitropyridine derivative (V) is reacted with a compound represented by the general formulas $R^2COZ$ or $(R^2CO)_2O$ to conduct amidation to obtain a 2-alkylamido-5-halogeno-3-nitropyridine derivative (III). In this step, the amidation is conducted by using an acid chloride (Z=a halogen atom in the above general formula $R^2COZ$), a carboxylic acid (Z=OH in the same formula), a mixed acid anhydride (Z=an alkoxycarbonyl group, an aryloxycarbonyl group or an aralkyloxycarbonyl group), an acid anhydride (the above general formula $((R^2CO)_2O)$ or an active ester of a carboxylic acid with N-hydroxybenozotriazole or N-hydroxysuccinimide in the conventional manner.

Step 2

This step is one wherein a 2-[N-(2'-cyanobiphenyl- 4-yl)methyl]alkylamido-5-halogeno-3-nitropyridine derivative (I) is prepared from the 2-alkylamido-5-halogeno-3-nitropyridine derivative (III). In conducting this step or step 6, an active biphenyl derivative (IV) represented by the following general formula is used as an N-alkylating agent:

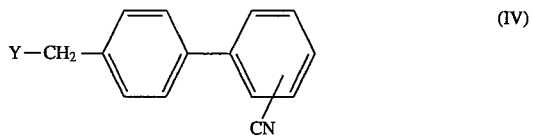

[wherein Y represents a leaving group used in the conventional organic synthesis, for example, a halogen atom, a methanesulfonyloxy group, an ethanesulfonyloxy group, a benzenesulfonyloxy group or a toluenesulfonyloxy group].

Specific examples thereof to be used include 2-(4'-bromomethylphenyl)benzonitrile, 2-(4'-chloromethylphenyl)benzonitrile, 2-(4'-methanesulfonyloxymethylphenyl)benzonitrile, 2-(4'-ethanesulfonyloxymethylphenyl)benzonitrile, 2-(4'-benzenesulfonyloxymethylphenyl)benzonitrile and 2-(4'-toluenesulfonyloxymethylphenyl)benzonitrile, which can be obtained by the producing process described in, e.g., the Japanese Patent Publication-A No. 3-236377 and according to the process which will be described below.

Step 3

This step is one wherein the 2-[N-(2'-cyanobiphenyl-4-yl)methyl]alkylamido-5-halogeno-3-nitropyridine derivative (I) is cyclized and dehalogenated into a 2-alkyl-3-(2'-cyanobiphenyl-4-yl)methyl-3H-imidazo[4,5-b]pyridine derivative (II) under reducing conditions. As the catalyst and reducing agent to be used in this step, the following combinations (a catalyst and a reducing agent), for example, can be cited specifically.

a) palladium-carbon (hereinafter referred to as "Pd-C"), amine and organic acid b) Pd-C and hydrogen gas c) sodium borohydride and cupric chloride d) Pd-C and sodium hypophosphite ($NaH_2PO_2$)

e) Pd-C, iron and acetic acid

The Pd-C catalyst according to the present invention may be any one so far as it is generally used in catalytic reduction. The palladium content of the catalyst is generally 2 to 20%, preferably 5 to 10%. Further, the form of the catalyst is not limited, but may be a dry powder, a wet body or an aqueous slurry. The amount of the catalyst to be used is generally 0.001 to 10% by weight, preferably 0.01 to 5% by weight, still preferably 0.1 to 1% by weight based on the compound (I), though the amount is not limited.

The organic acid according to the present invention is a lower carboxylic acid having 1 to 6 carbon atoms and specific examples thereof include formic acid, acetic acid and propionic acid.

The amine according to the present invention may be any one, so far as it can form a salt together with an organic acid such as formic acid or acetic acid. Specific examples of the amine to be generally used include triethylamine, trimethylamine, tripropylamine, diethylamine, dimethylamine, dipropylamine, diisopropylamine, dibutylamine, N,N-dimethylethylamine, N,N-dimethylpropylamine, N,N-dimethylisopropylamine, N,N-dimethylbutylamine, N,N-dimethylhexylamine, N,N-dimethylcyclohexylamine, N,N-dimethyloctylamine, N,N-dimethyldodecylamine, N,N-dimethylbenzylamine, N,N-dimethyl-2-chloroethylamine, N,N-dimethyl- 2-chloropropylamine, 2-chlorotriethylamine, N,N-diethylmethylamine, N,N,N',N'-tetramethylmethanediamine, N,N,N',N'-tetramethylethylenediamine, N,N-dimethylaniline, N,N-dimethyltoluidine, N,N-diethylaniline, ethanolamine, diethanolamine, triethanolamine, N-methylethanolamine, N,N-dimethylethanolamine, pyridine, N-methylpiperidine, N-methylmorpholine, 1,4-dimethylpiperazine, N-methylpyrrole, N-methylpyrrolidine and ammonia. Among these amines, triethylamine, trimethylamine, tripropylamine, diethylamine and ethanolamine are preferable, and triethylamine is still preferable.

When triethylamine and formic acid are used as the reducing agents, the cyclization can be generally conducted according to the process described in Journal of Organic Chemistry (J. Org. Chem.), 42 (22), 3491 to 3494, 1977. According to the present invention, the amine is used generally in an amount of 1 to 150 equivalents, preferably 1.5 to 50 equivalents, still preferably 2 to 20 equivalents based on the compound (I), while the organic acid is used generally in an amount of 1 to 50 equivalents, preferably 1.5 to 20 equivalents, still preferably 2 to 10 equivalents based on the compound (I).

Furthermore, according to the present invention, the reductive cyclization with a combination of a Pd-C catalyst with an amine and an organic acid may be conducted in the absence or presence of a solvent. Specific examples of the solvent to be used include, e.g., water, methanol, ethanol, n-propanol, i-propanol, butanol, tetrahydrofuran, 1,2-dimethoxyethane, diethyl ether, diisopropyl ether, methyl acetate, ethyl acetate, propyl acetate, methyl propionate, ethyl propionate, 1,4-dioxane, benzene, toluene, xylene, formic acid, acetic acid, propionic acid, diethylamine, triethylamine, tripropylamine. ethanolamine, n-hexane, n-octane and petroleum ether, among which water, methanol, ethanol, n-propanol, i-propanol, tetrahydrofuran, 1,2-dimethoxyethane, methyl acetate, ethyl acetate, propyl acetate, methyl propionate, ethyl propionate, formic acid, acetic acid, triethylamine and toluene are preferable, and water, methanol, ethanol, ethyl acetate, tetrahydrofuran, 1,2-dimethoxyethane, triethylamine and toluene are still preferable.

When the solvent is used, the amount thereof is generally 0.5 to 100 parts by volume, preferably 0.5 to 50 parts by volume, still preferably 1 to 20 parts by volume based on 1 part by weight of the compound (I), though the amount is not limited. The solvents may be used each alone or as a mixture of two or more of them.

The order of addition of the amine and the organic acid as the reducing agents is not limited. The amine may be added prior to the addition of the acid or the organic acid may be added prior to the addition of the amine. That is, the organic acid may be added to a suspension comprising the compound (I), the catalyst, the amine and, if necessary, a solvent, or the amine may be added to a suspension comprising the compound (I), the catalyst, the organic acid and, if necessary, a solvent.

The reaction temperature is not particularly limited. The reaction is generally conducted at from 0° C. to the refluxing temperature of the amine or solvent. Although the reaction time may be from about one minute to 48 hours, the reaction is generally completed in 30 minutes to 12 hours.

When hydrogen gas is used as the reducing agent, the cyclization can be carried out under the conditions employed conventionally in organic synthesis for catalytic reduction i.e., under the conditions of normal pressure (atmospheric pressure) to 150 kg/cm². This reaction is preferably conduted in a solvent and the kind and amount of the solvent and the temperature and time of the reaction may be the same as those described above for the case of using an amine and an organic acid as the reducing agents.

When sodium borohydride and cupric chloride are used as the reducing agents, the amount of sodium borohydride to be used is generally about 1 to 100 equivalents, preferably 2 to 80 equivalents, still preferably 5 to 50 equivalents based on the compound (I), though the amount is not limited. On the other hand, the amount of cupric chloride to be used is generally 1 to 50 equivalents, preferably 2 to 30 equivalents, still preferably 5 to 20 equivalents based on the compound (I). This reaction is also preferably conducted in a solvent and the kind and amount of the solvent and the temperature and time of the reaction may be the same as those described above for the case of using an amine and an organic acid as the reducing agents.

When sodium hypophosphite is used as the reducing agent, The amount thereof is generally 1 to 100 equivalents, preferably 2 to 50 equivalents, still preferably 5 to 20 equivalents based on the compound (I), though the amount is not limited. This reaction is also preferably conducted in a solvent and the kind and amount of the solvent and the temperature and time of the reaction may be the same as those described above for the case of using an amine and an organic acid as the reducing agents.

When iron and acetic acid are used as the reducing agents, the amounts of them are not limited. The amount of iron used is generally 1 to 100 equivalents, preferably 5 to 75 equivalents, still preferably 10 to 50 equivalents based on the compound (I), while the amount of acetic acid used is generally 1 to 500 equivalents, preferably 10 to 300 equivalents, still preferably 50 to 200 equivalents based on the compound (I). When a solvent is used in this reaction, the kind and amount of the solvent to be used and the temperature and time of the reaction may be the same as those described above for the case of using an amine and an organic acid as the reducing agents, though this reaction may be carried out in the absence of any solvent.

Step 4

Step 4 is one wherein only the 5-position halogen atom of the pyridine skeleton in the 2-[N-(2'-cyanobiphenyl- 4-yl)methyl]alkylamido-5-halogeno-3-nitropyridine derivative (I) is selectively reduced, i.e., replaced by a hydrogen atom, to form a 2-[N-(2'-cyanobiphenyl- 4-yl)methyl]alkylamido-3-nitropyridine derivative (VIII). This step can be conducted by using the same amine and organic acid as those described in explanation of step 3 as a combination of a catalyst and a reducing agent and by employing the same conditions as those of step 3 with respect to the solvent and reaction temperature as well. However, the reaction time is generally 5 minutes to 7 hours, preferably 30 minutes to 6 hours, still preferably to 5 hours.

Step 5 is one wherein the 2-[N-(2'-cyanobiphenyl-4-yl)methyl]alkylamido-3-nitropyridine derivative (VIII) obtained by conducting step 4 is cyclized into a 2-alkyl-3-(2'-cyanobiphenyl-4-yl)methyl-3H-imidazo-[4,5-b]pyridine derivative (II) under reducing conditions.

In this step, the reductive cyclization can be conducted by using the same combination of a catalyst and a reducing agent as that described in explanation of step 3 under the same conditions as those described in explanation of step 3. Alternatively, the reductive cyclization may be conducted by using any of the following reducing agents in the conventional manner.

a) iron and acetic acid b) iron and hydrochloric acid

Step 6

This step is one wherein the 2-[N-(2'-cyanobiphenyl-4-yl)methyl]alkylamido-5-halogeno-3-nitropyridine derivative (I) is reductively isomerized with activated carbon, hydrazine and ferric chloride to form a 2-[N-(2'-cyanobiphenyl-4-yl)methyl]amino-5-halogeno- 3-alkylamidopyridine derivative (VII). Although the amounts of activated carton, hydrazine and ferric chloride used are not limited, activated carbon is generally used in an amount of 1 to 50% by weight, preferably 3 to 40% by weight, still preferably 5 to 30% by weight based on the compound (I); hydrazine is generally in an amount of 1 to 50 equivalents, preferably 1.5 to 20 equivalents, still preferably 2 to 10 equivalents based on the compound (I); and ferric chloride is generally in an amount of 1 to 50 equivalents, preferably in an amount of 1.5 to 20 equivalents, still preferably 2 to 10 equivalents based on the compound (I). In this step, it is preferable to use a solvent. The kind of the solvent to be used and the reaction temperature may be the same as those of the case of using an amine and an organic acid in step 3. The reaction is generally completed within 48 hours.

Step 7

This step is one wherein a 2-alkyl-3-(2'-cyanobiphenyl-4-yl)methyl-3H-imidazo[4,5-b]pyridine derivative (II) is prepared from the 2-[N-(2'-cyanobiphenyl- 4-yl)methyl] amino-5-halogeno-3-alkylamidopyridine derivative (VII) obtained as the result of step 6 through cyclization and dehalogenation under reducing conditions. In this step, the reduction and cyclization can be conducted by using the same combination of a catalyst and a reducing agent as that described in explanation of step 3 under the same conditions as those described in explanation of step 3.

Step 8

This step is one wherein the 2-[N-(2'-cyanobiphenyl-4-yl)methyl]amino-5-halogeno-3-alkylamidopyridine derivative (VII) obtained in step 6 through reductive isomerization is cyclized into a 2-alkyl-3-(2'-cyanobiphenyl-4-yl)methyl-6-halogeno-3H-imidazo-[4,5-b]pyridine derivative (VI) under acidic conditions.

This reaction is not limited so far as it is conducted in the presence of any acid which is used in a conventional organic synthesis. The reaction is conducted with, for example, specifically, an inorganic acid such as hydrochloric acid, sulfuric acid, nitric acid, hydrobromic acid, hydroiodic acid, perchloric acid, phosphoric acid and polyphosphoric acid; or a sulfonic acid such as methanesulfonic acid, benzenesulfonic acid, p-toluenesulfonic acid and camphorsulfonic acid, under acidic conditions.

This step is also preferably conducted in the presence of a solvent. Specific examples of the solvent include tetrahydrofuran, 1,2-dimethoxyethane, diethyl ether, diisopropyl ether, methyl acetate, ethyl acetate, propyl acetate, methyl propionate, ethyl propionate, 1,4-dioxane, benzene, toluene, xylene, formic acid, acetic acid, propionic acid, n-hexane, n-octane and petroleum ether, among which tetrahydrofuran, 1,2-dimethoxyethane, formic acid, acetic acid, propionic acid, benzene, toluene and xylene are preferable, and formic acid, acetic acid, benzene, toluene and xylene are still preferable. The solvent is generally used in an amount of 0.5 to 100 parts by volume, preferably 0.5 to 50 parts by volume, still preferably 1 to 20 parts by volume based on 1 part by weight of the compound (VIII), though the amount thereof is nor limited. The above solvents may be used each alone or as a mixture of two or more of them.

Further, though the reaction temperature is not particularly limited, the reaction is generally conducted at from 0° C. to the refluxing temperature of the amine or solvent. Furthermore, in this step, the reaction can be accelerated by removing formed water from the reaction system by adding a dehydrating agent such as a molecular sieve or by forming an azeotropic mixture. In such a case, the reaction time is generally completed within 12 hours.

Step 9

This step is one wherein an objective 2-alkyl-3-( 2'-cyanobiphenyl-4-yl)methyl-3H-imidazo[4,5-b]-pyridine derivative (II) is obtained by reductively dehalogenating the 2-alkyl-3-(2'-alkoxycarbonylbiphenyl- 4-yl)methyl-6-halogeno-3H-imidazo[4,5-b]-pyridine derivative (VI) obtained by conducting step 8. This step can be conducted in the same manner as that of step 3.

Step 10

This step is one wherein the 2-[N-(2'-cyanobiphenyl-4-yl)methyl]cyclopropanecarboxamido- 5-halogeno-3-nitropyridine derivative (I) is reductively cyclized without the elimination of the halogen atom. In this step, reductive cyclization may be conducted by the use of iron and acetic acid or iron and hydrochloric acid in the conventional manner.

Step 11

The imidazopyridine derivatives which are disclosed in, e.g., Japanese Patent Publication-A Nos. 3-5480, 3-95181, 3-188076 and 3-236377 and are useful as antagonists against angiotensin II receptor are those having a 1H-tetrazol-5-yl group, for example, 2-alkyl-3-[{2'-(1H-tetrazol-5-yl)biphenyl-4-yl}-methyl]-3H-imidazo[4,5-b]pyridines. To obtain these compounds, they can be prepared by converting the cyano group of the compound (II) (such as 2-cyclopropyl-3-(2'-cyanobiphenyl-4-yl)methyl-7-methyl-3H-imidazo[4, 5-b]pyridine) prepared by the process of the present invention into a 1H-tetrazol-5-yl group by, e.g., the process (described in, e.g., Japanese Patent Publication-A No. 3-236377) using sodium azide and ammonium chloride. Among these imidazopyridine derivatives having a tetrazolyl group, one having a cyclopropyl group at the 2-position is particularly excellent in the antagonism against angiotensin II receptor and therefore is highly useful as an antihypertensive drug or a remedy for hemal lesions. The process for the preparation of a 2-alkyl-3-(2'-cyanobiphenyl-4-yl)methyl-3H-imidazo[4,5-b]pyridine derivative (II) according to the present invention enables the industrial production of a precursor of such an excellent antagonist against angiotensin II receptor.

Then, the 2-alkylamido-5-halogeno-3-nitropyridine derivative (III) of the following general formula is a novel compound and is useful as an intermediate for the preparation of the 2-alkyl-3-(2'-cyanobiphenyl-4-yl)methyl-3H-imidazo[4,5-b]pyridine derivative (II). The objective 2-alkyl-3-(2'-cyano-biphenyl-4-yl) -methyl-3H-imidazo[4,5-b]pyridine derivative (II) can be prepared from this intermediate (III) by conducting the above step 2 and then one of step 3, steps 4 and 5, steps 6 and 7, steps 10 and 9, and steps 6, 8 and 9.

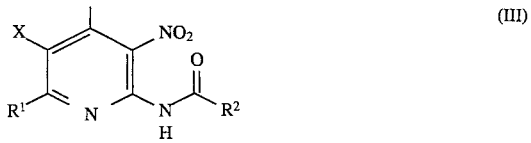

In the formula, $R^1$, $R^2$ and X are each as defined above. Further specific examples of the intermediate (III) according to the present invention include the following compounds, though the intermediate (III) is not limited to them.

(1) 2-cyclopropanecarboxamido-5-bromo-4-methyl-3-nitropyridine
(2) 2-cyclopropanecarboxamido-5-bromo-4,6-dimethyl-3-nitropyridine
(3) 2-cyclopropanecarboxamido-5-chloro-4-methyl-3-nitropyridine
(4) 2-cyclopropanecarboxamido-5-chloro-4,6-dimethyl-3-nitropyridine
(5) 2-n-butyrylamino-5-bromo-4-methyl-3-nitropyridine
(6) 2-n-butyrylamino-5-bromo-4,6-dimethyl-3-nitropyridine
(7) 2-n-butyrylamino-5-chloro-4-methyl-3-nitropyridine
(8) 2-n-butyrylamino-5-chloro-4,6-dimethyl-3-nitropyridine
(9) 2-n-valerylamino-5-bromo-4-methyl-3-nitropyridine
(10) 2-n-valerylamino-5-bromo-4,6-dimethyl-3-nitropyridine
(11) 2-n-valerylamino-5-chloro-4-methyl-3-nitropyridine
(12) 2-n-valerylamino-5-chloro-4,6-dimethyl-3-nitropyridine Further, the 2-[N-(2'-cyanobiphenyl-4-yl)methyl]-alkylamido- 5-halogeno-3-nitropyridine derivative (I) of the following general formula is also a novel compound and is useful as an intermediate for the preparation of the imidazopyridine derivative (II). The objective 2-alkyl-3-(2-cyanobiphenyl-4-yl)methyl- 3H-imidazo[4,5-b]pyridine derivative (II) can be prepared from the intermediate (I) through one of step 3, steps 4 and 5, steps 6 and 7, steps 10 and 9, and steps 6, 8 and 9.

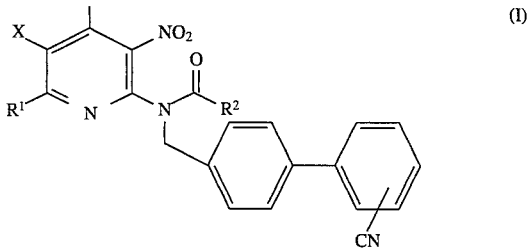

In the formula, $R^1$, $R^2$ and X are each as defined above, with the proviso that a case wherein $R^1$ is a hydrogen atom, $R^2$ is a n-butyl group and X is a bromine atom is excepted. Further specific examples of the intermediate (I) according to the present invention include the following compounds, though the intermediate (I) is not limited to them.

(1) 2-[N-(2'-cyanobiphenyl-4-yl)methyl]cyclopropanecarboxamido- 5-bromo-4-methyl-3-nitropyridine
(2) 2-[N-(2'-cyanobiphenyl-4-yl)methyl]cyclopropanecarboxamido- 5-bromo-4,6-dimethyl-3-nitropyridine
(3) 2-[N-(2'-cyanobiphenyl-4-yl)methyl]cyclopropanecarboxamido- 5-chloro-4-methyl-3-nitropyridine
(4) 2-[N-(2'-cyanobiphenyl-4-yl)methyl]cyclopropanecarboxamido- 5-chloro-4,6-dimethyl-3-nitropyridine
(5) 2-[N-(2'-cyanobiphenyl-4-yl)methyl]butyrylamino-5-bromo-4-methyl-3-nitropyridine
(6) 2-[N-(2'-cyanobiphenyl-4-yl)methyl]butyrylamino-5-bromo-4,6-dimethyl-3-nitropyridine
(7) 2-[N-(2'-cyanobiphenyl-4-yl)methyl]butyrylamino-5-chloro-4-methyl-3-nitropyridine
(8) 2-[N-(2'-cyanobiphenyl-4-yl)methyl]butyrylamino-5-chloro-4,6-dimethyl-3-nitropyridine
(9) 2-[N-(2'-cyanobiphenyl-4-yl)methyl]valerylamino-5-bromo-4,6-dimethyl-3-nitropyridine
(10) 2-[N-(2'-cyanobiphenyl-4-yl)methyl]valerylamino-5-chloro-4-methyl-3-nitropyridine
(11) 2-[N-(2'-cyanobiphenyl-4-yl)methyl]valerylamino-5-chloro-4,6-dimethyl-3-nitropyridine Further, the 2-[N-(2'-cyanobiphenyl-4-yl)methyl]-amino-5-halogeno-3-alkylamidopyridine derivative (VII) of the following general formula is also a novel compound and is useful as an intermediate for the preparation of the imidazopyridine derivative (II). The objective 2-alkyl-3-(2'-cyanobiphenyl-4-yl)-methyl- 3H-imidazo[4,5-b]pyridine derivative (II) can be prepared from this intermediate (VII) through either the above steps 6 and 7 or the above seeps 8 and 9.

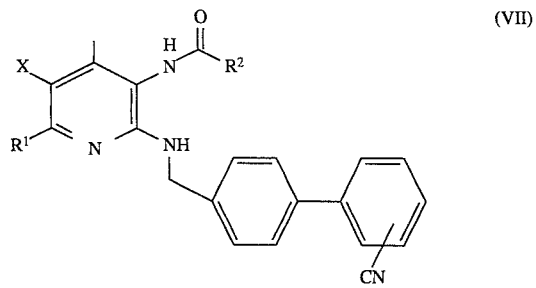

In the formula, $R^1$, $R^2$ and X are each as defined above. Further specific examples of the intermediate (VII) according to the present invention include the following compounds, though the intermediate (VII) is not limited to them.

(1) 3-cyclopropanecarboxamido-2-[N-(2'-cyanobiphenyl-4-yl)methyl]amino-5-bromo-4-methylpyridine
(2) 3-cyclopropanecarboxamido-2-[N-(2'-cyanobiphenyl-4-yl)methyl]amino-5-bromo-4,6-dimethylpyridine
(3) 3-cyclopropanecarboxamido-2-[N-(2'-cyanobiphenyl-4-yl)methyl]amino-5-chloro-4-methylpyridine
(4) 3-cyclopropanecarboxamido-2-[N-(2'-cyanobiphenyl-4-yl)methyl]amino-5-chloro-4,6-dimethylpyridine
(5) 3-n-butyrylamino-2-[N-(2'-cyanobiphenyl-4-yl)methyl] amino-5-bromo-4-methylpyridine
(6) 3-n-butyrylamino-2-[N-(2'-cyanobiphenyl-4-yl)-methyl] amino-5-bromo-4,6-dimethylpyridine
(7) 3-n-butyrylamino-2-[N-(2'-cyanobiphenyl-4-yl)-methyl] amino-5-chloro-4-methylpyridine
(8) 3-n-butyrylamino-2-[N-(2'-cyanobiphenyl-4-yl)-methyl] amino-5-chloro-4,6-dimethylpyridine
(9) 3-n-valerylamino-2-[N-(2'-cyanobiphenyl-4-yl)-methyl] amino-5-bromo-4-methylpyridine
(10) 3-n-valerylamino-2-[N-(2'-cyanobiphenyl-4-yl)-methyl]amino-5-bromo-4,6-dimethylpyridine
(11) 3-n-valerylamino-2-[N-(2'-cyanobiphenyl-4-yl)-methyl]amino-5-chloro-4-methylpyridine
(12) 3-n-valerylamino-2-[N-(2'-cyanobiphenyl-4-yl)-methyl]amino-5-chloro-4,6-dimethylpyridine Compounds in which $R^1$ is a hydrogen atom and the —CN is present at the 2'-position of the biphenyl in the above description and the application of the process of the present invention to the preparation of such compounds are particularly preferable.

Then, the present inventors have extensively studied to find an active biphenyl intermediate improved on the above disadvantages. As a result, they have found that a biphenyloxazoline derivative (I) represented by the following general formula which is a novel compound is an excellent industrial intermediate satisfying the above requirements, and have accomplished the present invention:

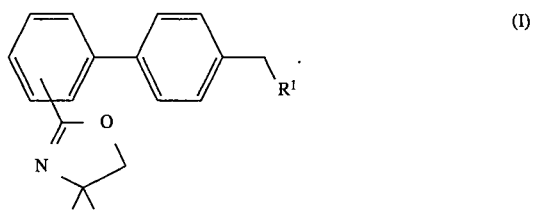
(I)

In the formula, R¹ represents a hydroxyl group, a lower alkylsulfonyloxy group, an arylsulfonyloxy group or a halogen atom.

The biphenyloxazoline derivative (I) according to the present invention can be prepared by any of the following processes.

(1) protecting 4-bromobenzyl alcohol to form a 4-bromobenzyl ether derivative (V), coupling it with oxazolylanisole to form an alkoxymethyl-biphenyloxazoline derivative (IV) through the Grignard reaction, eliminating the protective group to form a hydroxymethyl-biphenyloxazoline derivative (II), and then conducting sulfonylation or halogenation.

(2) oxidizing a methyl-biphenyloxazoline derivative (VIII) to form a carboxy-biphenyloxazoline derivative (VII), either esterifying it with a lower alcohol and then reducing it with a metal hydride complex or reducing it with a metal hydride complex to form a hydroxymethyl-biphenyloxazoline derivative (II), and then conducting sulfonylation or halogenation.

The outline of the reaction path according to the present invention is represented by the following chemical reaction scheme (reaction scheme-6):

Reaction Scheme-6

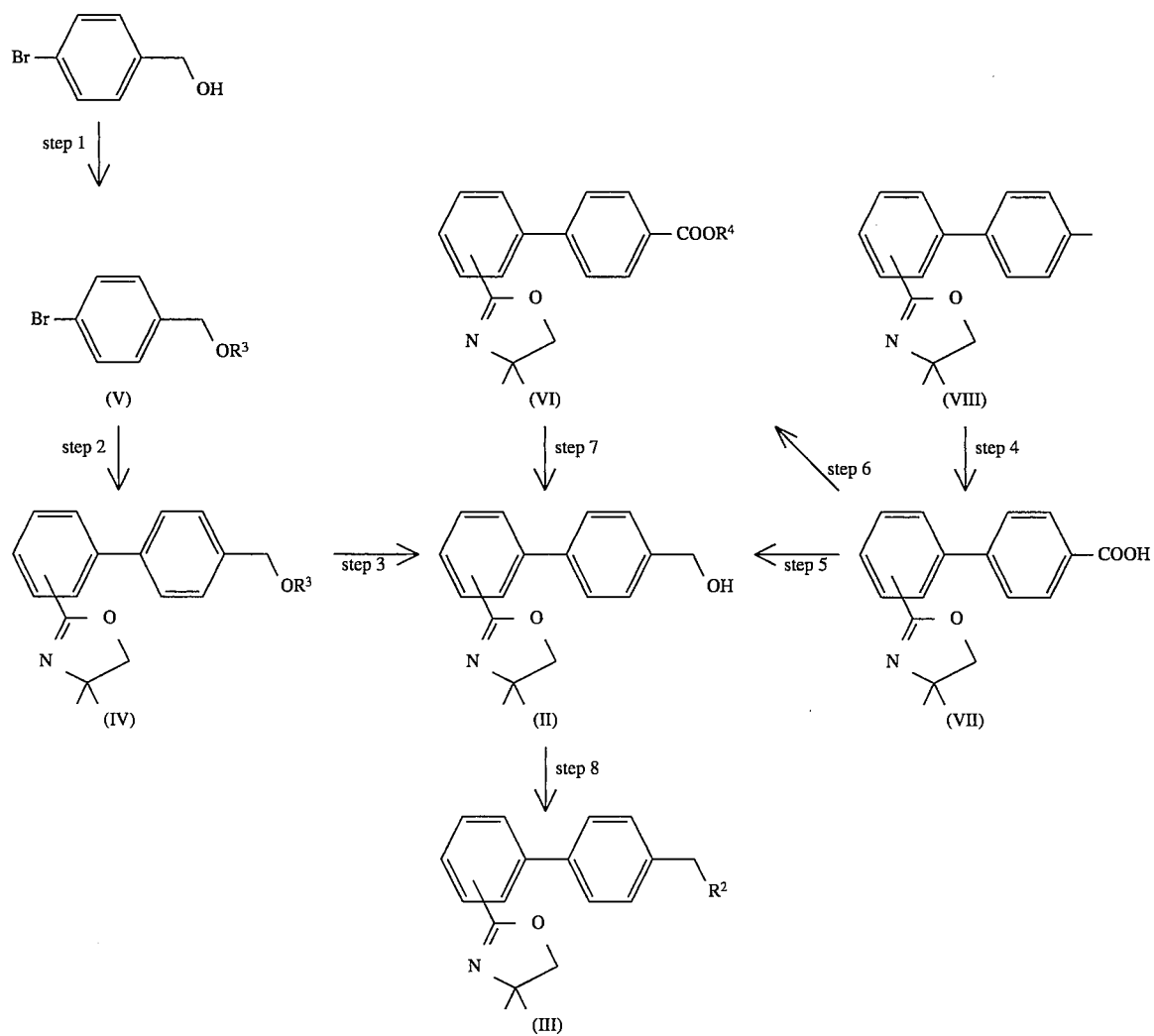

Accordingly, an object of the present invention is to provide a biphenyloxazoline derivative (I) which is an active intermediate useful for introducing the side chain of biphenyl in the preparation of a 2-alkyl- 3-(2'-alkoxycarbonylbiphenyl-4-yl)methyl-3H-imidazo[4,5-b]pyridine derivative which is an antagonist against angiotensin II receptor useful as an antihypertensive drug or a remedy for hemal lesions, a process for the preparation thereof, and further an intermediate useful for the preparation thereof.

The biphenyloxazoline derivative (I) according to the present invention has the following general formula:

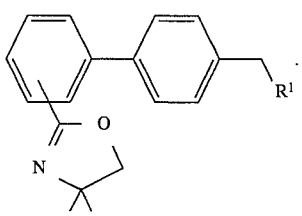

(I)

In the formula, $R^1$ represents a hydroxyl group, a lower alkylsulfonyloxy group, an arylsulfonyloxy group or a halogen atom. Specific examples of the lower alkylsulfonyloxy group include those having a lower alkyl group of 1 to 6 carbon atoms, such as a methanesulfonyloxy group and an ethanesulfonyloxy group: those of the arylsulfonyloxy group include a benzenesulfonyloxy group and a toluenesulfonloxy group; and those of the halogen atom include a chlorine atom, a bromine atom, an iodine atom and a fluorine atom.

Further, specific examples of the biphenyloxazoline derivative (I) include the following compounds, though the biphenyloxazoline derivative (I) according to the present invention is not limited to them.

(1) 4,4-dimethyl-2-(4'-hydroxymethylbiphenyl-2-yl)oxazoline
(2) 4,4-dimethyl-2-(4'-chloromethylbiphenyl-2-yl)oxazoline
(3) 4,4-dimethyl-2-(4'-bromomethylbiphenyl-2-yl)oxazoline
(4) 4,4-dimethyl-2-(4'-iodomethylbiphenyl-2-yl)oxazoline
(5) 4,4-dimethyl-2-(4'-methanesulfonyloxymethylbiphenyl-2-yl)oxazoline
(6) 4,4-dimethyl-2-(4'-ethanesulfonyloxymethylbiphenyl-2-yl)oxazoline
(7) 4,4-dimethyl-2-(4'-p-toluenesulfonyloxymethylbiphenyl- 2-yl)oxazoline
(8) 4,4-dimethyl-2-(4'-benzenesulfonyloxymethylbiphenyl-2-yl)oxazoline Then, the hydroxymethyl-biphenyloxazoline derivative (II) according to the present invention has the following general formula:

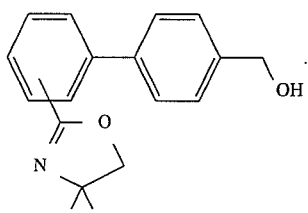

(II)

Specific examples thereof include the following compounds.
(1) 4,4-dimethyl-2-(4'-hydroxymethylbiphenyl-2-yl)oxazoline
(2) 4,4-dimethyl-2-(4'-hydroxymethylbiphenyl-3-yl)oxazoline
(3) 4,4-dimethyl-2-(4'-hydroxymethylbiphenyl-4-yl)oxazoline Then, the active biphenyloxazoline derivative (III) has the following chemical structural formula:

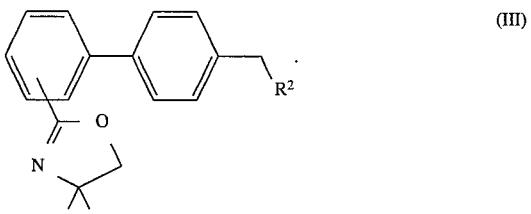

(III)

In the formula, $R^2$ represents a lower alkylsulfonyloxy group, an arylsulfonyloxy group or a halogen atom. Specific examples of these groups include the same groups as those described above.

Further specific examples of the active biphenyloxazoline derivative (III) include the following compounds, though the active biphenyloxazoline derivative (III) according to the present invention is not limited to them.

(1) 4,4-dimethyl-2-(4'-chloromethylbiphenyl-2-yl)oxazoline
(2) 4,4-dimethyl-2-(4'-bromomethylbiphenyl-2-yl)oxazoline
(3) 4,4-dimethyl-2-(4'-iodomethylbiphenyl-2-yl)oxazoline
(4) 4,4-dimethyl-2-(4'-methanesulfonyloxymethylbiphenyl-2-yl)oxazoline
(5) 4,4-dimethyl-2-(4'-ethanesulfonyloxymethylbiphenyl-2-yl)oxazoline
(6) 4,4-dimethyl-2-(4'-p-toluenesulfonyloxymethylbiphenyl- 2-yl)oxazoline
(7) 4,4-dimethyl-2-(4'-benzenesulfonyloxymethylbiphenyl-2-yl)oxazoline Further, the alkoxymethyl-biphenyloxazoline derivative (IV) according to the present invention has the following chemical structural formula:

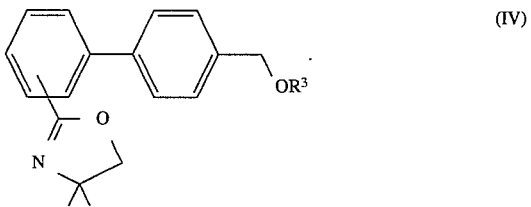

(IV)

In the formula, $R^3$ represents a lower alkoxyalkyl group, an aryloxyalkyl group, an aralkyloxyalkyl group, a lower alkoxyalkoxyalkyl group, a lower thioalkoxyalkyl group, a cycloether group, a trialkylsilyl group, a triarylsilyl group, a lower alkyl group, a vinyl group, an aralkyl group or a triphenylmethyl group.

Further specific examples of the lower alkoxyalkyl group include a methoxymethyl group, an ethoxymethyl group, a propoxymethyl group, a methoxyethyl group, an ethoxyethyl group, a propoxyethyl group and a propoxypropyl group: those of the aryloxyalkyl group include a phenoxymethyl group, a phenoxyethyl group and a tolyloxymethyl group; those of the aralkyloxyalkyl group include a benzyloxymethyl group and a phenethyloxymethyl group; those of the lower alkoxyalkoxyalkyl group include a methoxyethoxymethyl group and an ethoxyethoxymethyl group; those of the lower thioalkoxyalkyl group include a methylthiomethyl group, a methylthioethyl group, an ethylthiomethyl group, a phenylthiomethyl group and a benzylthiomethyl group; those of the cycloether group include a tetrahydropyranyl group and a tetrahydrofuranyl group; those of the trialkylsilyl group include a trimethylsilyl group, a triethylsilyl group, a t-butyldimethylsilyl group, an i-propyldimethylsilyl group and a phenyldimethylsilyl group; that of the triarylsilyl group includes a triphenylsilyl group; those of the lower alkyl group include a methyl group, an ethyl group, a propyl group and a t-butyl group; and those of the aralkyl group include a benzyl group, a phenethyl group, a methylbenzyl group, a trimethylbenzyl group, a nitrobenzyl group and a phenacyl group.

Further, specific and representative examples of the alkoxymethyl-biphenyloxazoline derivative (IV) include the following compounds, though the alkoxymethyl-biphenyloxazoline derivative (IV) according to the present invention is not limited to them.
(1) 4,4-dimethyl-2-(4-methoxymethoxymethylbiphenyl-2-yl)oxazoline
(2) 4,4-dimethyl-2-(4'-methoxyethoxymethoxymethylbiphenyl- 2-yl)oxazoline
(3) 4,4-dimethyl-2-(4'-thiomethoxymethoxymethylbiphenyl- 2-yl)oxazoline
(4) 4,4-dimethyl-2-(4-tetrahydropyranyloxymethylbiphenyl- 2-yl)oxazoline
(5) 4,4-dimethyl-2-(4-tetrahydrofurabyloxymethylbiphenyl-2-yl)oxazoline
(6) 4,4-dimethyl-2-(4-trimethylsilyloxymethylbiphenyl-2-yl)oxazoline
(7) 4,4-dimethyl-2-(4'-2-butoxymethylbiphenyl-2-yl)oxazoline
(8) 4,4-dimethyl-2-(4'-benzyloxymethylbiphenyl-2-yl)oxazoline Further, the 4-bromobenzyl ether derivative (V) according to the present invention has the following chemical structural formula:

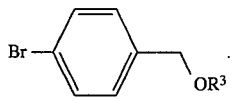
(V)

In the formula, $R^3$ is as defined above. Further specific examples of the 4-bromobenzyl ether derivative (V) include the following compounds, though the 4-bromobenzyl ether derivative (V) according to the present invention is not limited to them.
(1) 4-bromobenzyl-methoxymethyl ether
(2) 4-bromobenzyl-methoxyethoxymethyl ether
(3) 4-bromobenzyl-thiomethoxymethyl ether
(4) 4-bromobenzyl-tetrahydropyranyl ether
(5) 4-bromobenzyl-tetrahydrofuranyl ether
(6) 4-bromobenzyl-trimethylsilyl ether
(7) 4-bromobenzyl-t-butyl ether
(8) 4-bromobenzyl-benzyl ether Further, the alkoxycarbonyl-biphenyloxazoline derivative (VI) according to the present invention has the following chemical structural formula:

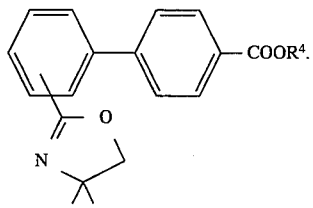
(VI)

In the formula, $R^4$ represents a lower alkyl group, an aryl group, an aralkyl group, a cycloether group, a trialkylsilyl group, a triarylsilyl group, a vinyl group, a lower alkoxyalkyl group, an aryloxyalkyl group, an aralkyloxyalkyl group, a thioalkoxyalkyl group or a triphenylmethyl group. It is preferable that $R^4$ be a lower alkyl group, an aryl group, an aralkyl group, a cycloether group, a trialkylsilyl group, a vinyl group, a lower alkoxyalkyl group, an aryloxyalkyl group, an aralkyloxyalkyl group, a thioalkoxyalkyl group or a triphenylmethyl group. Specific examples of the lower alkyl group include groups having 1 to 6 carbon atoms such as a methyl group, an ethyl group, a propyl group, a butyl group, a pentyl group and a hexyl group; those of the aryl group include a phenyl group, a tolyl group and a xylyl group; those of the aralkyl group include a benzyl group and a phenethyl group; those of the cycloether group include a tetrahydropyranyl group and a tetrahydrofuranyl group; those of the triarylsilyl group include a trimethylsilyl group, a triethylsilyl group, a t-butyldimethylsilyl group, an i-propyldimethylsilyl group and a phenyldimethylsilyl group; those of the lower alkoxyalkyl group include a methoxymethyl group, an ethoxymethyl group, a propoxymethyl group, a methoxyethyl group, an ethoxyethyl group, a propoxyethyl group and a propoxypropyl group; those of the aryloxyalkyl group include a phenoxymethyl group, a phenoxyethyl group and a tolyloxymethyl group; those of the aralkyloxyalkyl group include a benzyloxymethyl group and a phenethyloxymethyl group; and those of the thioalkoxyalkyl group include a methylthiomethyl group, a methylthioethyl group, an ethylthiomethyl group, a phenylthiomethyl group and a benzylthiomethyl group. Further specific examples of the alkoxycarbonyl-biphenyloxazoline derivative (VI) include the following compounds, though the alkoxycarbonyl-biphenyloxazoline derivative (VI) according to the present invention is not limited to them.
(1) 4,4-dimethyl-2-(4'-methoxycarbonylbiphenyl-2-yl)oxazoline
(2) 4,4-dimethyl-2-(4'-ethoxycarbonylbiphenyl-2-yl)oxazoline
(3) 4,4-dimethyl-2-(4'-propoxycarbonylbiphenyl-2-yl)oxazoline
(4) 4,4-dimethyl-2-(4'-phenoxycarbonylbiphenyl-2-yl)oxazoline
(5) 4,4-dimethyl-2-(4'-benzyloxycarbonylbiphenyl-2-yl)oxazoline
(6) 4,4-dimethyl-2-(4'-tetrahydropyranyloxycarbonylbiphenyl- 2-yl)oxazoline Further, the carboxy-biphenyloxazoline derivative (VII) according to the present invention has the following chemical structural formula:

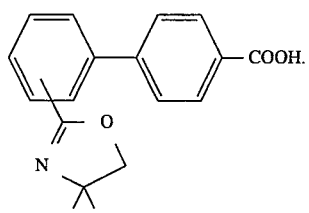
(VII)

Specific and representative examples of the carboxy-biphenyloxazoline derivative (VII) according to the present invention include the following compounds, though the derivative (VII) is not limited to them.
(1) 4,4-dimethyl-2-(4'-carboxybiphenyl-2-yl)oxazoline
(2) 4,4-dimethyl-2-(4'-carboxybiphenyl-3-yl)oxazoline
(3) 4,4-dimethyl-2-(4'-carboxybiphenyl-4-yl)oxazoline Further, the methyl-biphenyloxazoline derivative (VIII) according to the present invention has the following chemical structural formula:

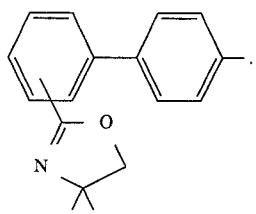
(VIII)

Specific and representative examples of the methyl-biphenyloxazoline derivative (VIII) according to the present invention include the following compounds, though the derivative (VIII) is not limited to them.
(1) 4,4-dimethyl-2-(4'-methylbiphenyl-2-yl)oxazoline
(2) 4,4-dimethyl-2-(4'-methylbiphenyl-3-yl)oxazoline
(3) 4,4-dimethyl-2-(4'-methylbiphenyl-4-yl)oxazoline Next, each step of the process according to the present invention will be described in detail hereinafter (see the above reaction scheme-6).

Step 1

This step is one wherein 4-bromobenzyl alcohol is protected to obtain a 4-bromobenzyl ether derivative (V). This step can be conducted according to the conventional process for introducing a protective group for a hydroxyl group in organic synthesis. Specific examples of the reagent for introducing a protective group usable in this step include chloromethyl methyl ether, 2-chloroethyl methyl ether, chloromethyl phenyl ether, chloromethyl benzyl ether, chloromethyl methoxyethyl ether, chloromethyl methyl sulfide, dihydropyrane, dihydrofuran, chlorotrimethylsilane, chlorotriethylsilane, chlorotriphenylsilane, methyl iodide, benzyl chloride and chlorotriphenylmethane.

Step 2

This step is one wherein the 4-bromobenzyl ether derivative (V) is coupled with oxazolylanisole to form an alkoxymethyl-biphenyloxazoline derivative (IV) through the Grignard reaction. This reaction can be conducted by the conventional process for the Grignard reaction as described in, e.g., Journal of Organic Chemistry (J. Org. Chem.), 43 (7), 1372 to 1379, 1978.

Step 3

In this step, the protective group of the alkoxymethyl-biphenyloxazoline derivative (IV) is eliminated to form a hydroxymethyl-biphenyloxazoline derivative (II). This reaction can be conducted according to a common process for eliminating the protective group such as hydrolysis and catalytic reduction.

Step 4

Step 4 is one wherein a methyl-biphenyloxazoline derivative (VIII) is oxidized into a carboxy-biphenyloxazoline derivative (VII). In this reaction, an oxidizing agent is used, and specific examples thereof usable in this reaction include permanganates, chromium oxide and bichromates, among which permanganates are preferable. This reaction can be conducted according to the process described in, e.g., Organic Synthesis, Col. Vol. II, 135. In the present invention, the methyl-biphenyloxazoline derivative (VIII) is dissolved in a solvent, a permanganate such as potassium permanganate is added thereto, and the obtained mixture is heated.

Although the amount of the permanganate used is not limited, it is generally used in an amount of about 1 to 100 equivalents, more preferably about 2 to 50 equivalents, still preferably about 3 to 20 equivalents per equivalent of the methyl-biphenyloxazoline derivative (VIII).

The solvent to be used in this reaction is not limited, so far as it is inert to the methyl-biphenyloxazoline derivative (VIII) or the oxidizing agent. Specific examples thereof include water, pyridine, formic acid and acetic acid. The solvent may be used either alone or as a mixture of two or more of them. Although the amount of the solvent used is not limited, it is generally used in an amount of about 0.5 to 100 parts by volume, more preferably about 0.5 to 50 parts by volume, still preferably about 1 to 20 parts by volume based on 1 part by weight of the methyl-biphenyloxazoline derivative (VIII).

This reaction is generally conducted under heating at a temperature ranging from 50° C. to the refluxing temperature of the solvent. Although the reaction time varies depending upon the kind or amount of the oxidizing agent, temperature or the like, it is generally completed in about 1 to 48 hours.

Steps 5 and 7

These steps are those wherein the carboxy-biphenyloxazoline derivative (VII) or the alkoxycarbonyl-biphenyloxazoline derivative (VI) is reduced with a metal hydride complex into a hydroxymethyl-biphenyloxazoline derivative (II). Specific examples of the metal hydride complex in the present invention include aluminum lithium hydride, bis(2-methoxyethoxy)aluminum sodium hydride, diisobutylaluminum hydride and diborane. Although the amount of the metal hydride complex used is not limited, it is generally used in an amount of about 0.2 to 50 equivalents, more preferably about 0.5 to 20 equivalents, still preferably about 1 to 10 equivalents per equivalent of the carboxy-biphenyloxazoline derivative (VII) or the alkoxycarbonyl-biphenyloxazoline derivative (VI).

It is preferable to use a solvent in this reaction. The solvent usable is not limited, so far as it is inert to the carboxy-biphenyloxazoline derivative (VII) or the alkoxycarbonyl-biphenyloxazoline derivative (VI), or the metal hydride complex. Specific examples thereof include tetrahydrofuran, 1,2-dimethoxyethane, ethyl ether, isopropyl ether, 2-methoxyethyl ether, dioxane, dioxolane, benzene, toluene, hexane and octane. The solvent may be used either alone or as a mixture of two or more of them. Although the amount of the solvent used is not limited, it is generally used in an amount of about 0.5 to 100 parts by volume, more preferably about 0.5 to 50 parts by volume, still preferably about 1 to-20 parts by volume based on 1 part by weight of the carboxy-biphenyloxazoline derivative (VII) or the alkoxycarbonyl-biphenyloxazoline derivative (VI).

Although this reaction can be generally conducted at a temperature ranging from −70° C. to the refluxing temperature of the solvent, it is generally conducted under cooling with ice. Although the reaction time varies depending upon the kind or amount of the metal hydride complex, temperature or the like, it is generally completed in about 5 minutes to 6 hours.

Step 6

This step is one wherein the carboxy-biphenyloxazoline derivative (VII) obtained in step 4 is esterified into an alkoxycarbonyl-biphenyloxazoline derivative (VI). This reaction can be conducted according to the common esterification process.

Step 8

This step is one wherein an active biphenyloxazoline derivative (III) is prepared through the sulfonylation or halogenation of the hydroxymethyl-biphenyloxazoline derivative (II).

The sulfonylation is conducted according to the conventional process with a reagent for sulfonylation such as methanesulfonyl chloride, ethanesulfonyl chloride, benzenesulfonyl chloride and p-toluenesulfonyl chloride. Although the amount of the reagent for sulfonylation used is not limited, it is generally used in an amount of about 1 to 50 equivalents, more preferably about 1.2 to 20 equivalents, still preferably 1.5 to 10 equivalents per equivalent of the hydroxymethyl-biphenyloxazoline derivative (II).

On the other hand, the halogenation is conducted according to the conventional process with a reagent for halogenation such as hydrochloric acid, thionyl chloride, sulfuryl chloride, phosphorus trichloride, phosphorus pentachloride, phosphorus oxychloride, oxalyl chloride, phosgene, diphosgene, triphosgene, hydrobromic acid, thionyl bromide and phosphorus tribromide. Although the amount of the reagent for halogenation used is not limited, it is generally used in an amount of about 1 to 50 equivalents, more preferably about 1.5 to 20 equivalents, still preferably about 2 to 10 equivalents per equivalent of the hydroxymethyl-biphenyloxazoline derivative (II).

The active biphenyloxazoline derivative (III) according to the present invention is highly stable and can be further purified by an ordinary method such as silica gel column chromatography and vacuum distillation.

Then, a 4-substituted biphenyloxazoline derivative (IX) represented by the following general formula is a novel compound and is useful as an intermediate for the preparation of the biphenyloxazoline derivative (I) according to the present invention:

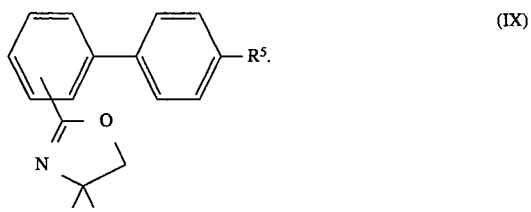

In the formula, $R^5$ represents a carboxyl group, a lower alkoxycarbonyl group, a lower alkoxyalkoxymethyl group, an aryloxyalkoxymethyl group, an aralkyloxyalkoxymethyl group, a lower alkoxyalkoxyalkoxymethyl group, a lower thioalkoxyalkoxymethyl group, a cycloetheroxymethyl group, a trialkylsilyloxymethyl group, a triarylsilyloxymethyl group, a lower alkoxymethyl group, a vinyloxymethyl group, an aralkyloxymethyl group or a triphenylmethoxymethyl group.

As specific examples of the substituent of $R^5$, those of the lower alkoxycarbonyl group include groups having an alkyl group of 1 to 6 carbon atoms in the molecule, such as a methoxycarbonyl group, an ethoxycarbonyl group and a propoxycarbonyl group; those of the lower alkoxyalkoxymethyl group include a methoxymethoxymethyl group, an ethoxymethoxymethyl group, a propoxymethoxymethyl group, a methoxyethoxymethyl group, an ethoxyethoxymethyl group, a propoxyethoxymethyl group and a propoxypropoxymethyl group; those of the aryloxyalkoxymethyl group include a phenoxymethoxymethyl group, a phenoxyethoxymethyl group and a tolyloxymethoxymethyl group; those of the aralkyloxyalkoxymethyl group include a benzyloxymethoxymethyl group and a phenethyloxymethoxymethyl group; those of the lower alkoxyalkoxyalkoxymethyl group include a methoxyethoxymethoxymethyl group and an ethoxyethoxymethoxymethyl group; those of the lower thioalkoxyalkoxymethyl group include a methylthiomethoxymethyl group, a methylthioethoxymethyl group, an ethylthiomethoxymethyl group, a phenylthiomethoxymethyl group and a benzylthiomethoxymethyl group; those of the cycloetheroxymethyl group include a tetrahydropyranyloxymethyl group and a tetrahydrofuranyloxymethyl group; those of the trialkylsilyloxymethyl group include a timethylsilyloxymethyl group, a triethylsilyloxymethyl group, a t-butyldimethylsilyloxymethyl group, an i-propyldimethylsilyloxymethyl group and a phenyldimethylsilyloxymethyl group, that of the triarylsilyloxymethyl group includes a triphenylsilyloxymethyl group; those of the lower alkoxymethyl group include a methoxymethyl group, an ethoxymethyl group, a propoxymethyl group and a t-butoxymethyl group; and those of the aralkyloxymethyl group include a benzyloxymethyl group, a phenethyloxymethyl group, a methylbenzyloxymethyl group, a trimethylbenzyloxymethyl group, a nitrobenzyloxymethyl group and a phenacyloxymethyl group.

Further specific and representative examples of the 4-substituted biphenyloxazoline derivative (IX) include the following compounds, though the 4-substituted biphenyloxazoline derivative (IX) according to the present invention is not limited to them.

(1) 4,4-dimethyl-2-(4'-methoxymethoxymethylbiphenyl-2-yl)oxazoline
(2) 4,4-dimethyl-2-(4'-methoxyethoxymethoxymethylbiphenyl- 2-yl)oxazoline
(3) 4,4-dimethyl-2-(4'-thiomethoxymethoxymethylbiphenyl- 2-yl)oxazoline
(4) 4,4-dimethyl-2-(4'-tetrahydropyranyloxymethylbiphenyl- 2-yl)oxazoline
(5) 4,4-dimethyl-2-(4'-tetrahydrofuranyloxymethylbiphenyl- 2-yl)oxazoline
(6) 4,4-dimethyl-2-(4'-trimethylsilyloxymethylbiphenyl-2-yl)oxazoline
(7) 4,4-dimethyl-2-(4'-2-butoxymethylbiphenyl-2-yl)oxazoline
(8) 4,4-dimethyl-2-(4'-benzyloxymethylbiphenyl-2-yl)oxazoline
(9) 4,4-dimethyl-2-(4'-carboxybiphenyl-2-yl)oxazoline
(10) 4,4-dimethyl-2-(4'-carboxybiphenyl-3-yl)oxazoline
(11) 4,4-dimethyl-2-(4'-carboxybiphenyl-4-yl)oxazoline
(12) 4,4-dimethyl-2-(4'-methoxycarbonylbiphenyl-2-yl)oxazoline
(13) 4,4-dimethyl-2-(4'-ethoxycarbonylbiphenyl-2-yl)oxazoline
(14) 4,4-dimethyl-2-(4'-propoxycarbonylbiphenyl-2-yl)oxazoline
(15) 4,4-dimethyl-2-(4'-phenoxycarbonylbiphenyl-2-yl)oxazoline
(16) 4,4-dimethyl-2-(4'-benzyloxycarbonylbiphenyl-2-yl)oxazoline
(17) 4,4-dimethyl-2-(4'-tetrahydropyranyloxycarbonylbiphenyl- 2-yl)oxazoline Then, the present inventors have extensively studied to find an active biphenyl intermediate improved in the above disadvantages. As a result, they have found that a sulfonyloxy-biphenylcarboxylic ester derivative (I) of the following general formula which is a novel compound is an excellent industrial intermediate satisfying the above requirements, and have accomplished the present invention:

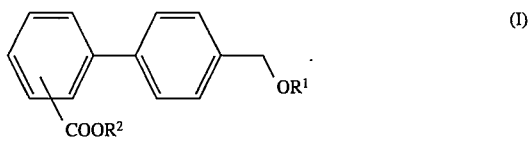

In the formula, $R^1$ represents a lower alkylsulfonyloxy group or an arylsulfonyloxy group; and $R^2$ represents a lower alkyl group, an aryl group, an aralkyl group, a cycloether group, a triarylsilyl group, a vinyl group, a lower alkoxyalkyl group, an aryloxyalkyl group, an aralkyloxyalkyl group, a thioalkoxyalkyl group or a triphenylmethyl group.

The sulfonyloxy-biphenylcarboxylic ester derivative (I) according to the present invention can be prepared by any of the following processes.

(1) protecting 4-bromobenzyl alcohol to form a 4-bromobenzyl ether derivative (VI), coupling it with oxazolylanisole to form an alkoxymethyl-biphenyloxazoline derivative (V) through the Grignard reaction, eliminating the protective group to form a hydroxymethyl-biphenyloxazoline derivative (IV), eliminating the protective group to form a hydroxymethyl-biphenylcarboxylic acid derivative (III), esterifying it into a hydroxymethyl-biphenylcarboxylic ester derivative (II), and then conducting sulfonylation.

(2) oxidizing a methyl-biphenyloxazoline derivative (IX) with an oxidizing agent into a carboxy-biphenyloxazoline derivative (VII), either esterifying it with a lower alcohol into an alkoxycarbonyl-biphenyloxazoline derivative (VIII) and then reducing it with a metal hydride complex or directly reducing it with a metal hydride complex to form a hydroxymethyl-biphenyloxazoline derivative (IV), eliminating the protective group to form a hydroxymethyl-biphenylcarboxylic acid derivative (III), esterifying it into a hydroxymethyl-biphenylcarboxylic ester derivative (II) and, further, conducting sulfonylation.

The outline of the reaction path according to the present invention is represented by the following chemical reaction scheme (reaction scheme-7).

Reaction Scheme-7

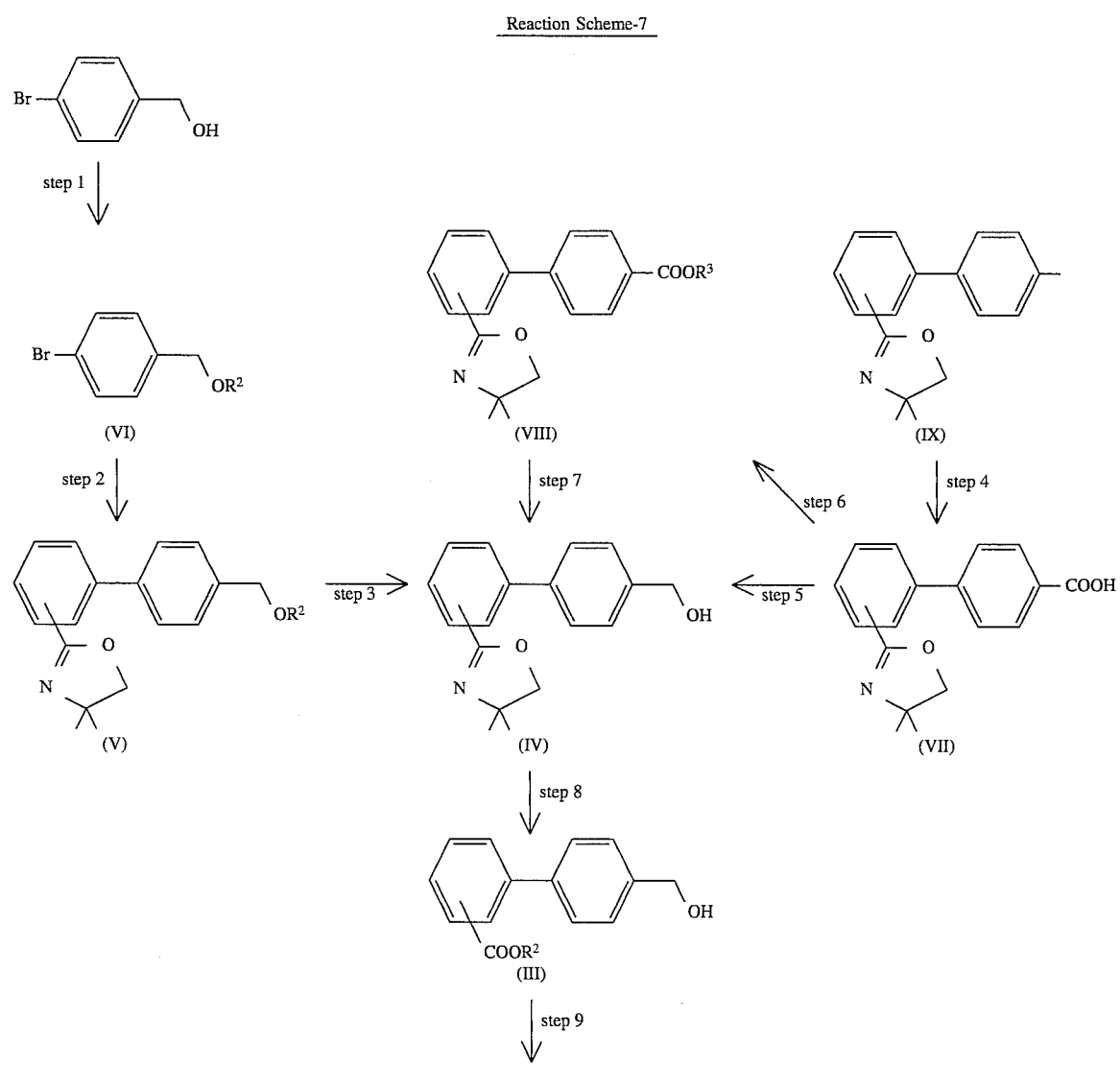

-continued
Reaction Scheme-7

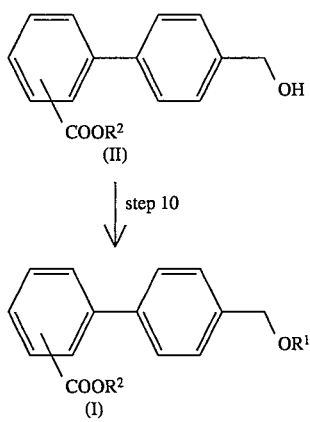

Accordingly, an object of the present invention is to provide a sulfonyloxy-biphenylcarboxylic ester derivative (I) which is an active intermediate useful for introducing the side chain of biphenyl in the preparation of a 2-alkyl-3-(2'-alkoxycarbonylbiphenyl- 4-yl)methyl-3H-imidazo[4,5-b] pyridine derivative which is an antagonist against angiotensin II receptor useful as an antihypertensive drug and a remedy for hemal lesions, a process for the preparation thereof, and an intermediate useful for the preparation thereof.

The sulfonyloxy-biphenylcarboxylic ester derivative (I) according to the present invention has the following general formula:

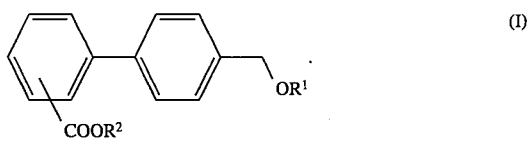

(I)

In the formula, $R^1$ represents a lower alkylsulfonyloxy group or an arylsulfonyloxy group; and $R^2$ represents a lower alkyl group, an aryl group, an aralkyl group, a cycloether group, a triarylsilyl group, a vinyl group, a lower alkoxyalkyl group, an aryloxyalkyl group, an aralkyloxyalkyl group, a thioalkoxyalkyl group or a triphenylmethyl group. Specific examples of the lower alkylsulfonyloxy group of $R^1$ include groups having an alkyl group of 1 to 6 carbon atoms in the molecule, such as a methanesulfonyloxy group and an ethanesulfonyloxy group; and those of the arylsulfonyloxy group include a benzenesulfonyloxy group and a toluenesulfonyloxy group. Further, specific examples of the lower alkyl group of $R^2$ include groups having 1 to 6 carbon atoms, such as a methyl group, an ethyl group, a n-propyl group, an i-propyl group, a n-butyl group, an i-butyl group, a t-butyl group, a pentyl group and a hexyl group; those of the aryl group include a phenyl group, a tolyl group and a xylyl group; those of the aralkyl group include a benzyl group and a phenethyl group; those of the cycloether group include a tetrahydropyranyl group and a tetrahydrofuranyl group; those of the triarylsilyl group include a trimethylsilyl group, a triethylsilyl group, a t-butyldimethylsilyl group, an i-propyldimethylsilyl group and a phenyldimethylsilyl group; those of the lower alkoxyalkyl group include a methoxymethyl group, an ethoxymethyl group, a propoxymethyl group, a methoxyethyl group, an ethoxyethyl group, a propoxyethyl group and a propoxypropyl group; those of the aryloxyalkyl group include a phenoxymethyl group, a phenoxyethyl group and a tolyloxymethyl group; those of the aralkyloxyalkyl group include a benzyloxymethyl group and a phenethyloxymethyl group; and those of the thioalkoxyalkyl group include a methylthiomethyl group, a methylthioethyl group, an ethylthiomethyl group, a phenylthiomethyl group and a benzylthiomethyl group.

Further specific examples of the sulfonyloxy-biphenylcarboxylic ester derivative (I) include the following compounds, though the sulfonyloxy-biphenylcarboxylic ester derivative (I) according to the present invention is not limited to them.

(1) methyl 2-(4'-methanesulfonyloxymethylphenyl)benzoate
(2) methyl 3-(4'-methanesulfonyloxymethylphenyl)benzoate
(3) methyl 4-(4'-methanesulfonyloxymethylphenyl)benzoate
(4) ethyl 2-(4'-methanesulfonyloxymethylphenyl)benzoate
(5) ethyl 3-(4'-methanesulfonyloxymethylphenyl)benzoate
(6) ethyl 4-(4'-methanesulfonyloxymethylphenyl)benzoate
(7) methyl 2-(4'-ethanesulfonyloxymethylphenyl)benzoate benzoate
(8) methyl 3-(4'-ethanesulfonyloxymethylphenyl)benzoate
(9) methyl 4-(4'-ethanesulfonyloxymethylphenyl)benzoate
(10) ethyl 2-(4'-ethanesulfonyloxymethylphenyl)benzoate
(11) ethyl 3-(4'-ethanesulfonyloxymethylphenyl)benzoate
(12) ethyl 4-(4'-ethanesulfonyloxymethylphenyl)benzoate
(13) methyl 2-(4'-p-toluenesulfonyloxymethylphenyl)benzoate (14) methyl 3-(4'-p-toluenesulfonyloxymethylphenyl)benzoate (15) methyl 4-(4'-p-toluenesulfonyloxymethylphenyl)benzoate (16) ethyl 2-(4'-p-toluenesulfonyloxymethylphenyl)benzoate (17) ethyl 3-(4'-p-toluenesulfonyloxymethylphenyl)benzoate (18) ethyl 4-(4'-p-toluenesulfonyloxymethylphenyl)benzoate (19) methyl 2-(4'-benzenesulfonyloxymethylphenyl)benzoate (20) methyl 3-(4'-benzenesulfonyloxymethylphenyl)benzoate (21) methyl 4-(4'-benzenesulfonyloxymethylphenyl)benzoate (22) ethyl 2-(4'-benzenesulfonyloxymethylphenyl)benzoate (23) ethyl 3-(4'-benzenesulfonyloxymethylphenyl)benzoate (24) ethyl 4-(4'-benzenesulfonyloxymethylphenyl)benzoate Then, the hydroxymethyl-biphenylcarboxylic ester derivative (II) according to the present invention has the following general formula:

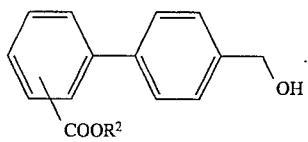
(II)

In the formula, $R^2$ is as defined above. Specific examples of the hydroxymethyl-biphenylcarboxylic ester derivative (II) according to the present invention include the following compounds, though the derivative (II) is not limited to them.
(1) methyl 2-(4'-hydroxymethylphenyl)benzoate
(2) methyl 3-(4'-hydroxymethylphenyl)benzoate
(3) methyl 4-(4'-hydroxymethylphenyl)benzoate
(4) ethyl 2-(4'-hydroxymethylphenyl)benzoate
(5) ethyl 3-(4'-hydroxymethylphenyl)benzoate
(6) ethyl 4-(4'-hydroxymethylphenyl)benzoate Then, the hydroxymethyl-biphenylcarboxylic acid derivative (III) has the following chemical structural formula:

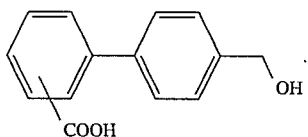
(III)

Further specific examples of the hydroxymethyl-biphenylcarboxylic acid derivative (III) include the following compounds, though the hydroxymethyl-biphenylcarboxylic acid derivative (III) according to the present invention is not limited to them.
(1) 2-(4'-hydroxymethylphenyl)benzoic acid
(2) 3-(4'-hydroxymethylphenyl)benzoic acid
(3) 4-(4'-hydroxymethylphenyl)benzoic acid Further, the hydroxymethyl-biphenyloxazoline derivative (IV) according to the present invention has the following chemical structural formula:

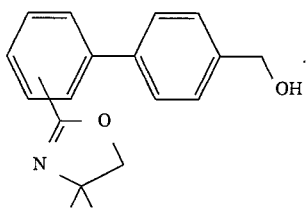
(IV)

Further specific examples of the hydroxymethyl-biphenyloxazoline derivative (IV) according to the present invention include the following compounds, though the derivative (IV) is not limited to them.
(1) 4,4-dimethyl-2-(4'-hydroxymethylbiphenyl-2-yl)oxazoline
(2) 4,4-dimethyl-2-(4'-hydroxymethylbiphenyl-3-yl)oxazoline
(3) 4,4-dimethyl-2-(4'-hydroxymethylbiphenyl-4-yl)oxazoline Then, the alkoxymethyl-biphenyloxazoline derivative (V) has the following chemical structural formula:

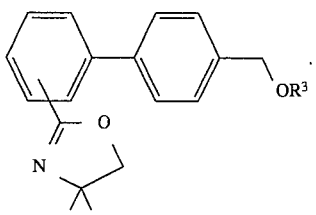
(V)

In the formula, $R^3$ represents a lower alkoxyalkyl group, an aryloxyalkyl group, an aralkyloxyalkyl group, a lower alkoxyalkoxyalkyl group, a thioalkoxyalkyl group, a cycloether group, a trialkylsilyl group, a triarylsilyl group, a lower alkyl group, a vinyl group, an aralkyl group or a triphenylmethyl group.

Further specially, examples of the lower alkoxyalkyl group include a methoxymethyl group, an ethoxymethyl group, a propoxymethyl group, a methoxyethyl group, an ethoxyethyl group, a propoxyethyl group and a propoxypropyl group; those of the aryloxyalkyl group include a phenoxymethyl group, a phenoxyethyl group and a tolyloxymethyl group; those of the aralkyloxyalkyl group include a benzyloxymethyl group and a phenethyloxymethyl group; those of the lower alkoxyalkoxyalkyl group include a methoxyethoxymethyl group and an ethoxyethoxymethyl group; those of the thioalkoxyalkyl group include a methylthiomethyl group, a methylthioethyl group, an ethylthiomethyl group, a phenylthiomethyl group and a benzylthiomethyl group; those of the cycloether group include a tetrahydropyranyl group and a tetrahydrofuranyl group; those of the trialkylsilyl group include a trimethylsilyl group, a triethylsilyl group, a t-butyldimethylsilyl group, an i-propyldimethylsilyl group and a phenyldimethylsilyl group; that of the triarylsilyl group includes a triphenylsilyl group; those of the lower alkyl group include a methyl group, an ethyl group, a propyl group and a t-butyl group; and those of the aralkyl group include a benzyl group, a phenethyl group, a methylbenzyl group, a trimethylbenzyl group, a nitrobenzyl group and a phenacyl group.

Further, specific and representative examples of the alkoxymethyl-biphenyloxazoline derivative (V) include the following compounds, though the alkoxymethyl-biphenyloxazoline derivative (V) according to the present invention is not limited to them.
(1) 4,4-dimethyl-2-(4'-methoxymethoxymethylbiphenyl-2-yl)oxazoline
(2) 4,4-dimethyl-2-(4'-methoxyethoxymethoxymethylbiphenyl- 2-yl)oxazoline
(3) 4,4-dimethyl-2-(4'-thiomethoxymethoxymethylbiphenyl- 2-yl)oxazoline
(4) 4,4-dimethyl-2-(4'-tetrahydropyranyloxymethylbiphenyl- 2-yl)oxazoline
(5) 4,4-dimethyl-2-(4'-tetrahydrofuranyloxymethylbiphenyl- 2-yl)oxazoline
(6) 4,4-dimethyl-2-(4'-trimethylsilyloxymethylbiphenyl-2-yl)oxazoline
(7) 4,4-dimethyl-2-(4'-t-butoxymethylbiphenyl-2-yl)oxazoline
(8) 4,4-dimethyl-2-(4'-benzyloxymethylbiphenyl-2-yl)oxazoline Further, the 4-bromobenzyl ether derivative (VI) according to the present invention has the following chemical structural formula:

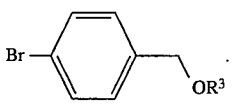
(VI)

In the formula, $R^3$ is as defined above. Further specific examples of the 4-bromobenzyl ether derivative (VI) include the following compounds, though the 4-bromobenzyl ether derivative (VI) according to the present invention is not limited to them.
(1) 4-bromobenzyl-methoxymethyl ether
(2) 4-bromobenzyl-methoxyethoxymethyl ether
(3) 4-bromobenzyl-thiomethoxymethyl ether
(4) 4-bromobenzyl-tetrahydropyranyl ether
(5) 4-bromobenzyl-tetrahydrofuranyl ether
(6) 4-bromobenzyl-trimethylsilyl ether
(7) 4-bromobenzyl-t-butyl ether
(8) 4-bromobenzyl-benzyl ether Further, the carboxy-biphenyloxazoline derivative (VII) according to the present invention has the following chemical structural formula:

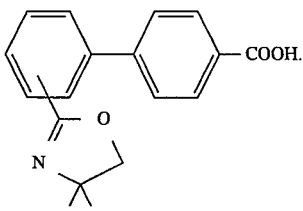
(VII)

Further specific examples of the carboxy-biphenyloxazoline derivative (VII) according to the present invention include the following compounds, though the derivative (VII) is not limited to them.
(1) 4,4-dimethyl-2-(4'-carboxybiphenyl-2-yl)oxazoline
(2) 4,4-dimethyl-2-(4'-carboxybiphenyl-3-yl)oxazoline
(3) 4,4-dimethyl-2-(4'-carboxybiphenyl-4-yl)oxazoline Further, the alkoxycarbonyl-biphenyloxazoline derivative (VIII) according to the present invention has the following chemical structural formula:

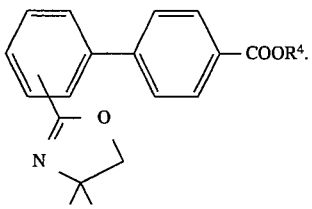
(VIII)

In the formula, $R^4$ represents a lower alkyl group, an aryl group, an aralkyl group, a cycloether group, a trialkylsilyl group, a triarylsilyl group, a vinyl group, a lower alkoxyalkyl group, an aryloxyalkyl group, an aralkyloxyalkyl group, a thioalkoxyalkyl group or a triphenylmethyl group. It is preferable that $R^4$ be a lower alkyl group, an aryl group, an aralkyl group, a cycloether group, a triarylsilyl group, a vinyl group, a lower alkoxyalkyl group, an aryloxyalkyl group, an aralkyloxyalkyl group, a thioalkoxyalkyl group or a triphenylmethyl group. Specific examples of the lower alkyl group include groups having 1 to 6 carbon atoms, such as a methyl group, an ethyl group, a propyl group, a butyl group, a pentyl group and a hexyl group; those of the aryl group include a phenyl group, a tolyl group and a xylyl group; those of the aralkyl group include a benzyl group and a phenethyl group; those of the cycloether group include a tetrahydropyranyl group and a tetrahydrofuranyl group; those of the triarylsilyl group include a trimethylsilyl group, a triethylsilyl group, a t-butyldimethylsilyl group, an i-propyldimethylsilyl group and a phenyldimethylsilyl group; those of the lower alkoxyalkyl group include a methoxymethyl group, an ethoxymethyl group, a propoxymethyl group, a methoxyethyl group, an ethoxyethyl group, a propoxyethyl group and a propoxypropyl group; those of the aryloxyalkyl group include a phenoxymethyl group, a phenoxyethyl group and a tolyloxymethyl group; those of the aralkyloxyalkyl group include a benzyloxymethyl group and a phenethyloxymethyl group; and those of the thioalkoxyalkyl group include a methylthiomethyl group, a methylthioethyl group, an ethylthiomethyl group, a phenylthiomethyl group and a benzylthiomethyl group. Further specific examples of the alkoxycarbonyl-biphenyloxazoline derivative (VIII) include the following compounds, though the alkoxycarbonyl-biphenyloxazoline derivative (VIII) according to the present invention is not limited to them.
(1) 4,4-dimethyl-2-(4'-methoxycarbonylbiphenyl-2-yl)oxazoline
(2) 4,4-dimethyl-2-(4'-ethoxycarbonylbiphenyl-2-yl)oxazoline
(3) 4,4-dimethyl-2-(4'-propoxycarbonylbiphenyl-2-yl)oxazoline
(4) 4,4-dimethyl-2-(4'-phenoxycarbonylbiphenyl-2-yl)oxazoline
(5) 4,4-dimethyl-2-(4'-benzyloxycarbonylbiphenyl-2-yl)oxazoline
(6) 4,4-dimethyl-2-(4'-tetrahydropyranyloxycarbonylbiphenyl- 2-yl)oxazoline Further, the methyl-biphenyloxazoline derivative (IX) according to the present invention has the following chemical structural formula:

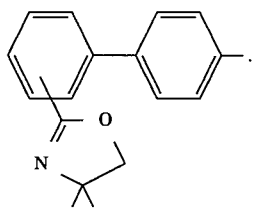
(IX)

Further, specific and representative examples of the methyl-biphenyloxazoline derivative (IX) according to the present invention include the following compounds, though the derivative (IX) is not limited to them.
(1) 4,4-dimethyl-2-(4'-methylbiphenyl-2-yl)oxazoline
(2) 4,4-dimethyl-2-(4'-methylbiphenyl-3-yl)oxazoline
(3) 4,4-dimethyl-2-(4'-methylbiphenyl-4-yl)oxazoline Next, each step of the process according to the present invention will be described in detail hereinafter (see the above reaction scheme-7).

Step 1

This step is one wherein 4-bromobenzyl alcohol is protected to obtain a 4-bromobenzyl ether derivative (VI). This step can be conducted according to the conventional process for introducing a protective group for a hydroxyl group in organic synthesis. Specific examples of the reagent for introducing a protective group usable in the present invention include chloro-methyl methyl ether, 2-chloroethyl methyl ether, chloromethyl phenyl ether, chloromethyl benzyl ether, chloromethyl methoxyethyl ether, chloromethyl methyl sulfide, dihydropyrane, dihydrofuran, chlorotrimethylsilane, chlorotriethylsilane, chlorotriphenylsilane, methyl iodide, benzyl chloride and chlorotriphenylmethane.

Step 2

This step is one wherein the 4-bromobenzyl ether derivative (VI) is coupled with oxazolylanisole to form an alkoxymethyl-biphenyloxazoline derivative (V) through the Grignard reaction. This reaction can be conducted by the conventional process for the Grignard reaction as described in, e.g., Journal of Organic Chemistry (J. Org. Chem.), 43 (7), 1372 to 1379, 1978.

Step 3

In this step, the protective group of the alkoxymethyl-biphenyloxazoline derivative (V) is eliminated to form a hydroxymethyl-biphenyloxazoline derivative (IV). This reaction can be conducted according to a common process for eliminating the protective group such as hydrolysis and catalytic reduction.

Step 4

Step 4 is one wherein a methyl-biphenyloxazoline derivative (IX) is oxidized into a carboxy-biphenyloxazoline derivative (VII). In this reaction, an oxidizing agent is used, and specific examples thereof usable in the present invention include permanganates, chromium oxide and bichromates, among which permanganates are preferable. This reaction can be conducted according to the process described in, Organic Synthesis, Col. Vol. II, 135. In the present invention, the methyl-biphenyloxazoline derivative (IX) is dissolved in a solvent, a permanganate such as potassium permanganate is added therto, and the obtained mixture is heated.

Although the amount of the permanganate used is not limited, it is generally used in an amount of about 1 to 100 equivalents, more preferably about 2 to 50 equivalents, still preferably about 3 to 20 equivalents per equivalent of the methyl-biphenyloxazoline derivative (IX).

The solvent to be used in this reaction is not limited, so far as it is inert to the methyl-biphenyloxazoline derivative (IX) or the oxidizing agent. Specific examples thereof include water, pyridine, formic acid and acetic acid. The solvent may be used either alone or as a mixture of two or more of them. Although the amount of the solvent used is not limited, it is generally used in an amount of about 0.5 to 100 parts by volume, more preferably about 0.5 to 50 parts by volume, still preferably about 1 to 20 parts by volume based on 1 part by weight of the methyl-biphenyloxazoline derivative (IX).

This reaction is generally conducted under heating at a temperature ranging from 50° C. to the refluxing temperature of the solvent. Although the reaction time varies depending upon the kind or amount of the oxidizing agent, temperature or the like, it is generally completed in about 1 to 48 hours.

Steps 5 and 7

These steps are those wherein the carboxy-biphenyloxazoline derivative (VII) or the alkoxycarbonyl-biphenyloxazoline derivative (VIII) is reduced with a metal hydride complex into a hydroxymethyl-biphenyloxazoline derivative (IV). Specific examples of the metal hydride complex in the present invention include aluminum lithium hydride, bis(2-methoxyethoxy)aluminum sodium hydride, diisobutylaluminum hydride and diborane. Although the amount of the metal hydride complex used is not limited, it is generally used in an amount of about 0.2 to 50 equivalents, more preferably about 0.5 to 20 equivalents, still preferably about 1 to 10 equivalents per equivalent of the carboxy-biphenyloxazoline derivative (VII) or the alkoxycarbonyl-biphenyloxazoline derivative (VIII).

It is preferable to use a solvent in this reaction. The solvent usable is not limited, so far as it is inert to the carboxy-biphenyloxazoline derivative (VII) or the alkoxycarbonyl-biphenyloxazoline derivative (VIII), or the metal hydride complex. Specific examples thereof include tetrahydrofuran, 1,2-dimethoxyethane, ethyl ether, isopropyl ether, 2-methoxyethyl ether, dioxane, dioxolane, benzene, toluene, hexane and octane. The solvent may be used either alone or as a mixture of two or more of them. Although the amount thereof used is not limited, it is generally used in an amount of about 0.5 to 100 parts by volume, more preferably about 0.5 to 50 parts by volume, still preferably about 1 to 20 parts by volume based on 1 part by weight of the carboxy-biphenyloxazoline derivative (VII) or the alkoxycarbonyl-biphenyloxazoline derivative (VIII).

Although this reaction can be generally conducted at a temperature ranging from −70° C. to the refluxing temperature of the solvent, it is generally conducted under cooling with ice. Although the reaction time varies depending upon the kind or amount of the metal hydride complex, temperature or the like, it is generally completed in about 5 minutes to 6 hours.

Step 6

This step is one wherein the carboxy-biphenyloxazoline derivative (VII) obtained in step 4 is esterified into an alkoxycarbonyl-biphenyloxazoline derivative (VIII). This reaction can be conducted according to the common esterification process.

Step 8

This step is one wherein the protective group of the hydroxymethyl-biphenyloxazoline derivative (IV) is eliminated to form a hydroxymethyl-biphenylcarboxylic acid derivative (III). Although this reaction can be conducted by the conventional processes for hydrolyzing oxazoline into a carboxylic acid in organic synthesis, i.e., by acidic hydrolysis, basic hydrolysis, a process using methyl iodide and sodium hydroxide described in Journal of Organic Chemistry (J. Org. Chem.), 39(3), 2778, 1974, or a combination thereof, sulfuric acid hydrolysis, a combination of hydrochloric acid hydrolysis and sodium hydroxide hydrolysis, or the above process using methyl iodide and sodium hydroxide is preferable in the present invention.

Step 9

This step is one wherein the hydroxymethyl-biphenylcarboxylic acid derivative (III) is esterified into a hydroxymethyl-biphenylcarboxylic ester derivative (II). This reaction can be conducted according to the common esterification process.

Step 10

This step is one wherein a sulfonyloxy-biphenylcarboxylic ester derivative (I) is prepared through the sulfonylation of the hydroxymethyl-biphenylcarboxylic ester derivative (II).

In the present invention, the sulfonylation is conducted according to the conventional process with a reagent for sulfonylation such as methanesulfonyl chloride, ethanesulfonyl chloride, benzenesulfonyl chloride and p-toluenesulfonyl chloride. Although the amount of the reagent for sulfonylation used is not limited, it is generally used in an amount of about 1 to 50 equivalents, more preferably about 1.2 to 20 equivalents, still preferably 1.5 to 10 equivalents per equivalent of the hydroxymethyl-biphenyloxazoline derivative (II).

The sulfonyloxy-biphenylcarboxylic ester derivative (I) according to the present invention is highly stable and can be further purified by an ordinary method such as silica gel column chromatography and vacuum distillation.

Then, a hydroxymethyl-biphenylcarboxylic acid derivative (X) represented by the following general formula is a novel compound and is useful as an intermediate for the preparation of the sulfonyloxy-biphenylcarboxylic ester derivative (I) according to the present invention:

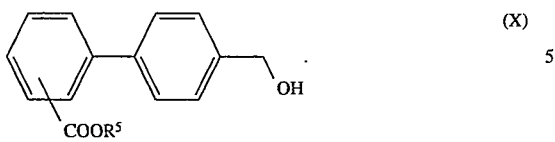

In the formula, $R^5$ represents a hydrogen atom, a lower alkyl group, an aryl group, an aralkyl group, a cycloether group, a trialkylsilyl group, a triarylsilyl group, a vinyl group, a lower alkoxyalkyl group, an aryloxyalkyl group, an aralkyloxyalkyl group, a thioalkoxyalkyl group or a triphenylmethyl group.

Further specific examples of the lower alkyl group include groups having 1 to 6 carbon atoms, such as a methyl group, an ethyl group, a n-propyl group, an i-propyl group, a n-butyl group, an i-butyl group, a t-butyl group, a pentyl group and a hexyl group; those of the aryl group include a phenyl group, a tolyl group and a xylyl group; those of the aralkyl group include a benzyl group and a phenethyl group; those of the cycloether group include a tetrahydropyranyl group and a tetrahydrofuranyl group; those of the trialkylsilyl group include a trimethylsilyl group, a triethylsilyl group, a t-butyldimethylsilyl group, an i-propyldimethylsilyl group and a phenyldimethylsilyl group; that of the triarylsilyl group includes a triphenylsilyl group; those of the lower alkoxyalkyl group include a methoxymethyl group, an ethoxymethyl group, a propoxymethyl group, a methoxyethyl group, an ethoxyethyl group, a propoxyethyl group and a propoxypropyl group; those of the aryloxyalkyl group include a phenoxymethyl group, a phenoxyethyl group and a tolyloxymethyl group; those of the aralkyloxyalkyl group include a benzyloxymethyl group and a phenethyloxymethyl group; and those of the thioalkoxyalkyl group include a methylthiomethyl group, a methylthioethyl group, an ethylthiomethyl group, a phenylthiomethyl group and a benzylthiomethyl group.

Further specific and representative examples of the hydroxymethyl-biphenylcarboxylic acid derivative (X) include the following compounds, though the hydroxymethyl-biphenylcarboxylic acid derivative (X) according to the present invention is not limited to them.
(1) 2-(4'-hydroxymethylphenyl)benzoic acid
(2) 3-(4'-hydroxymethylphenyl)benzoic acid
(3) 4-(4'-hydroxymethylphenyl)benzoic acid
(4) methyl 2-(4'-hydroxymethylphenyl)benzoate
(5) ethyl 2-(4'-hydroxymethylphenyl)benzoate
(6) propyl 2-(4'-hydroxymethylphenyl)benzoate
(7) t-butyl 2-(4'-hydroxymethylphenyl)benzoate
(8) phenyl 2-(4'-hydroxymethylphenyl)benzoate
(9) benzyl 2-(4'-hydroxymethylphenyl)benzoate
(10) tetrahydropyranyl 2-(4'-hydroxymethylphenyl)benzoate
(11) tetrahydrofuranyl 2-(4'-hydroxymethylphenyl)benzoate
(12) trimethylsilyl 2-(4'-hydroxymethylphenyl)benzoate
(13) methoxymethyl 2-(4'-hydroxymethylphenyl)benzoate
(14) thiomethoxymethyl 2-(4'-hydroxymethylphenyl)benzoate Then, the present inventors have extensively studied to develop a novel process for the preparation of a halomethyl-biphenylcarboxylic ester derivative (II) improved in the above disadvantages. As a result, they have found that the object can be attained by any of the following processes, and have accomplished the present invention.

(1) halogenating a hydroxymethyl-biphenylcarboxylic ester derivative (I).

(2) esterifying a hydroxymethyl-biphenylcarboxylic acid derivative (III) into a hydroxymethyl-biphenylcarboxylic ester derivative (I) and further halogenating it.

(3) eliminating the protective group of a hydroxymethyl-biphenyloxazoline derivative (IV) form a hydroxymethyl-biphenylcarboxylic acid derivative (III), then esterifying it into a hydroxymethyl-biphenylcarboxylic ester derivative (I), and further halogenating it.

(4) eliminating the protective group of an alkoxymethyl-biphenyloxazoline derivative (V) to form a hydroxymethyl-biphenyloxazoline derivative (IV), eliminating the protective group thereof to form a hydroxymethyl-biphenylcarboxylic acid derivative (III), then esterifying it into a hydroxymethyl-biphenylcarboxylic ester derivative (I), and further halogenating (5) coupling a 4-bromobenzyl ether derivative (VI) with oxazolylanisole to form an alkoxymethyl-biphenyloxazoline derivative (V) through the Grignard reaction, eliminating the protective group thereof to form a hydroxymethyl-biphenyloxazoline derivative (IV), eliminating the protective group thereof to form a hydroxymethyl-biphenylcarboxylic acid derivative (III), then esterifying it into a hydroxymethyl-biphenylcarboxylic ester derivative (I), and further halogenating it.

(6) protecting 4-bromobenzyl alcohol to form a 4-bromobenzyl ether derivative (VI), coupling it with oxazolylanisole to form an alkoxymethyl-biphenyloxazoline derivative (V) through the Grignard reaction, eliminating the protective group thereof to form a hydroxymethyl-biphenyloxazoline derivative (IV), eliminating the protective group thereof to form a hydroxymethyl-biphenylcarboxylic acid derivative (III), then esterifying it into a hydroxymethyl-biphenylcarboxylic ester derivative (I), and further halogenating it.

(7) reducing a carboxy-biphenyloxazoline derivative (VII) or an alkoxycarbonyl-biphenyloxazoline derivative (VIII) with a metal hydride complex into a hydroxymethyl-biphenyloxazoline derivative (IV), eliminating the protective group thereof to form a hydroxymethyl-biphenylcarboxylic acid derivative (III), then esterifying it into a hydroxymethyl-biphenylcarboxylic ester derivative (I), and further halogenating it.

(8) esterifying a carboxy-biphenyloxazoline derivative (VII) with a lower alcohol to form an alkoxycarbonyl-biphenyloxazoline derivative (VIII), reducing it with a metal hydride complex into a hydroxymethyl-biphenyloxazoline derivative (IV), eliminating the protective group thereof to form a hydroxymethyl-biphenylcarboxylic acid derivative (III), then esterifying it into a hydroxymethyl-biphenylcarboxylic ester derivative (I), and further halogenating it.

(9) oxidizing a methyl-biphenyloxazoline derivative (IX) with an oxidizing agent into a carboxy-biphenyloxazoline derivative (VII), either esterifying it with a lower alcohol to form an alkoxycarbonyl-biphenyloxazoline derivative (VIII) and reducing it with a metal hydride complex or reducing it with a metal hydride complex directly to form a hydroxymethyl-biphenyloxazoline derivative (IV), eliminating the protective group thereof to form a hydroxymethyl-biphenylcarboxylic acid derivative (III), then esterifying it into a hydroxymethyl-biphenylcarboxylic ester derivative (I), and further halogenating it.

The outline of the reaction path according to the present invention is represented by the following chemical reaction formula (reaction scheme-8).

Reaction Scheme-8

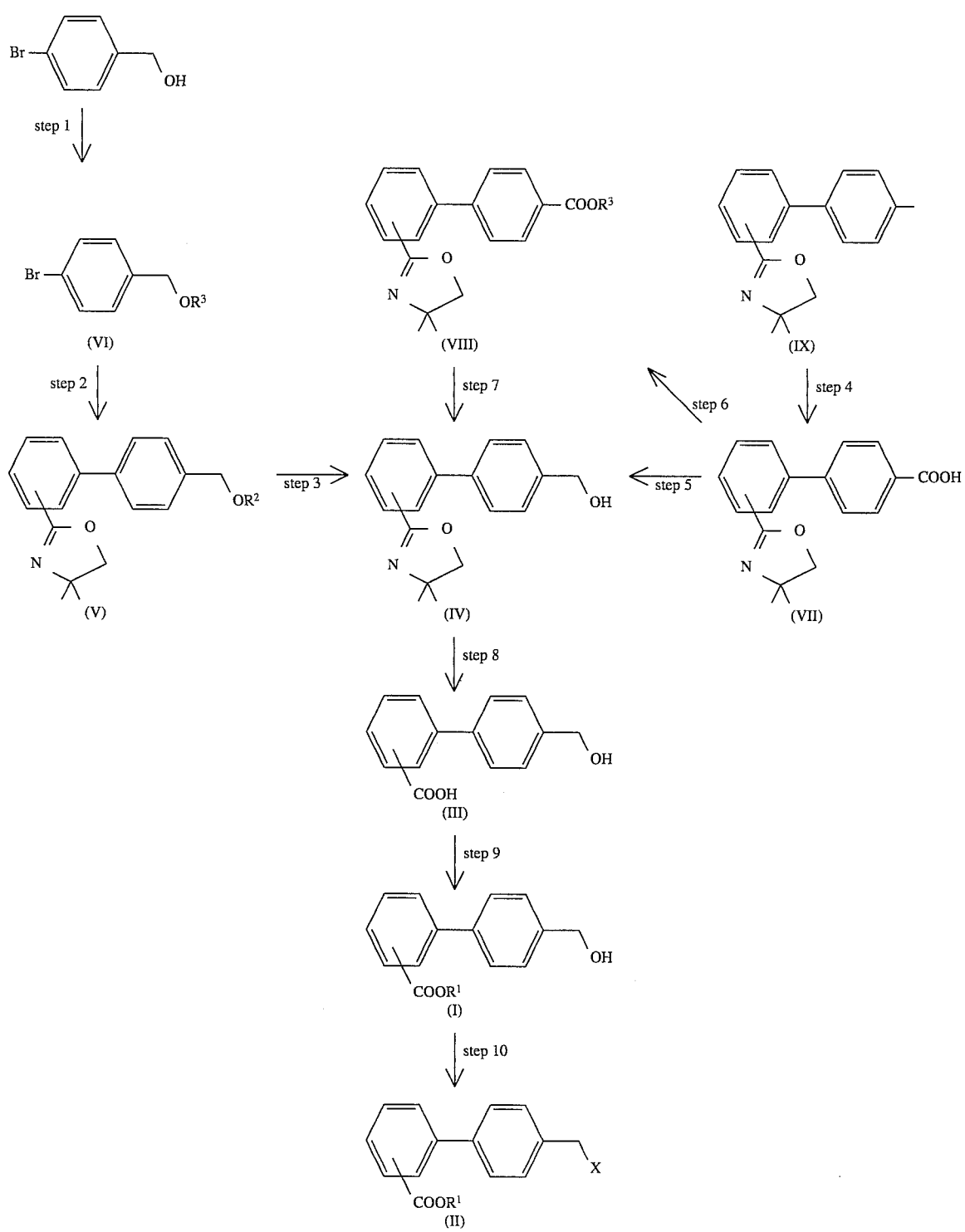

Accordingly, an object of the present invention is to provide a process for the preparation of a halomethyl-biphenylcarboxylic ester derivative (II) which is an active intermediate useful for the introduction of the side chain of biphenyl in preparing a 2-alkyl-3-(2'-alkoxycarbonylbiphenyl-4-yl)methyl-3H-imidazo-[4,5-b]pyridine derivative which is an antagonist against angiotensin II receptor useful as an antihypertensive drug and a remedy for hemal lesions.

The hydroxymethyl-biphenylcarboxylic ester derivative (I) according to the present invention has the following general formula:

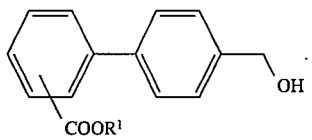

In the formula, $R^1$ represents a lower alkyl group, an aryl group, an aralkyl group, a cycloether group, a triarylsilyl group, a vinyl group, a lower alkoxyalkyl group, an aryloxyalkyl group, an aralkyloxyalkyl group, a thioalkoxyalkyl group or a triphenylmethyl group. Specific examples of the lower alkyl group include groups having 1 to 6 carbon atoms, such as a methyl group, an ethyl group, a n-propyl group, an i-propyl group, a n-butyl group, an i-butyl group, a t-butyl group, a pentyl group and a hexyl group; those of the aryl group include a phenyl group, a tolyl group and a xylyl group; those of the aralkyl group include a benzyl group and a phenethyl group; those of the cycloether group include a tetrahydropyranyl group and a tetrahydrofuranyl group; those of the triarylsilyl group include a trimethylsilyl group, a triethylsilyl group, a t-butyldimethylsilyl group, an i-propyldimethylsilyl group and a phenyldimethylsilyl group; those of the lower alkoxyalkyl group include a methoxymethyl group, an ethoxymethyl group, a propoxymethyl group, a methoxyethyl group, an ethoxyethyl group, a propoxyethyl group and a propoxypropyl group; those of the aryloxyalkyl group include a phenoxymethyl group, a phenoxyethyl group and a tolyloxymethyl group; those of the aralkyloxyalkyl group include a benzyloxymethyl group and a phenethyloxymethyl group; and those of the thioalkoxyalkyl group include a methylthiomethyl group, a methylthioethyl group, an ethylthiomethyl group, a phenylthiomethyl group and a benzylthiomethyl group.

Specific examples of the hydroxymethyl-biphenylcarboxylic ester derivative (I) include the following compounds, though the hydroxymethyl-biphenylcarboxylic ester derivative (I) according to the present invention is not limited to them.
(1) methyl 2-(4'-hydroxymethylphenyl)benzoate
(2) methyl 3-(4'-hydroxymethylphenyl)benzoate
(3) methyl 4-(4'-hydroxymethylphenyl)benzoate
(4) ethyl 2-(4'-hydroxymethylphenyl)benzoate
(5) ethyl 3-(4'-hydroxymethylphenyl)benzoate
(6) ethyl 4-(4'-hydroxymethylphenyl)benzoate Then, the halomethyl-biphenylcarboxylic ester derivative (II) according to the present invention has the following general formula:

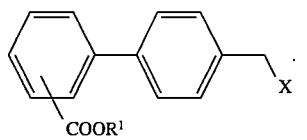

In the formula, $R^1$ and X are each as defined above. Further specific examples of the halomethyl-biphenylcarboxylic ester derivative (II) according to the present invention include the following compounds, though the derivative (II) is not limited to them.
(1) methyl 2-(4'-bromomethylphenyl)benzoate
(2) methyl 2-(4'-chloromethylphenyl)benzoate
(3) methyl 2-(4'-iodomethylphenyl)benzoate
(4) methyl 2-(4'-fluoromethylphenyl)benzoate
(5) methyl 3-(4'-bromomethylphenyl)benzoate
(6) methyl 3-(4'-chloromethylphenyl)benzoate
(7) methyl 4-(4'-bromomethylphenyl)benzoate
(8) methyl 4-(4'-chloromethylphenyl)benzoate
(9) ethyl 2-(4'-bromomethylphenyl)benzoate
(10) ethyl-2-(4'-chloromethylphenyl)benzoate
(11) ethyl 3-(4'-bromomethylphenyl)benzoate
(12) ethyl 3-(4'-chloromethylphenyl)benzoate
(13) ethyl 4-(4'-bromomethylphenyl)benzoate
(14) ethyl 4-(4'-chloromethylphenyl)benzoate Then, the hydroxymethyl-biphenylcarboxylic acid derivative (III) has the following chemical structural formula:

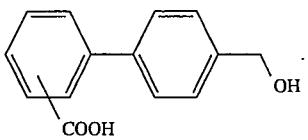

Further specific examples of the hydroxymethyl-biphenylcarboxylic acid derivative (III) include the following compounds, though the hydroxymethyl-biphenylcarboxylic acid derivative (III) according to the present invention is not limited to them.
(1) 2-(4'-hydroxymethyl)benzoic acid
(2) 3-(4'-hydroxymethyl)benzoic acid
(3) 4-(4'-hydroxymethyl)benzoic acid Further, the hydroxymethyl-biphenyloxazoline derivative (IV) according to the present invention has the following chemical structural formula:

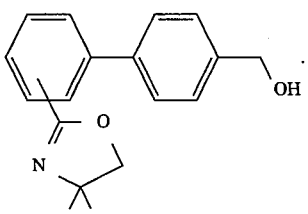

Further specific examples of the hydroxymethyl-biphenyloxazoline derivative (IV) according to the present invention include the following compounds, though the derivative (IV) is not limited to them.
(1) 4,4-dimethyl-2-(4'-hydroxymethylbiphenyl-2-yl)oxazoline
(2) 4,4-dimethyl-2-(4'-hydroxymethylbiphenyl-3-yl)oxazoline
(3) 4,4-dimethyl-2-(4'-hydroxymethylbiphenyl-4-yl)oxazoline Then, the alkoxymethyl-biphenyloxazoline derivative (V) has the following chemical structural formula:

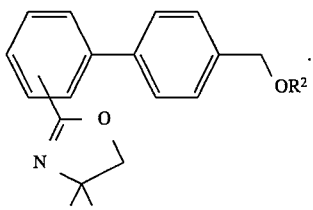

In the formula, $R^2$ represents a lower alkoxyalkyl group, an aryloxyalkyl group, an aralkyloxyalkyl group, a lower alkoxyalkoxyalkyl group, a thioalkoxyalkyl group, a cycloether group, a trialkylsilyl group, a triarylsilyl group, a lower alkyl group, a vinyl group, an aralkyl group or a triphenylmethyl group.

Further specific examples of the lower alkoxyalkyl group include a methoxymethyl group, an ethoxymethyl group, a propoxymethyl group, a methoxyethyl group, an ethoxyethyl group, a propoxyethyl group and a propoxypropyl group; those of the aryloxyalkyl group include a phenoxymethyl group, a phenoxyethyl group and a tolyloxymethyl group; those of the aralkyloxyalkyl group include a benzyloxymethyl group and a phenethyloxymethyl group; those of the lower alkoxyalkoxyalkyl group include a methoxyethoxymethyl group and an ethoxyethoxymethyl group; those of the thioalkoxyalkyl group include a methylthiomethyl group, a methylthioethyl group, an ethylthiomethyl group, a phenylthiomethyl group and a benzylthiomethyl group; those of the cycloether group include a tetrahydropyranyl group and a tetrahydrofuranyl group; those of the trialkylsilyl group include a trimethylsilyl group, a triethylsilyl group, a t-butyldimethylsilyl group, an i-propyldimethylsilyl group and a phenyldimethylsilyl group; that of the triarylsilyl group include a triphenylsilyl group; those of the lower alkyl group include a methyl group, an ethyl group, a propyl group and a t-butyl group; and those of the aralkyl group include a benzyl group, a phenethyl group, a methylbenzyl group, a trimethylbenzyl group, a nitrobenzyl group and a phenacyl group.

Further, specific and representative examples of the alkoxymethyl-biphenyloxazoline derivative (V) include the following compounds, though the alkoxymethyl-biphenyloxazoline derivative (V) according to the present invention is not limited to them.

(1) 4,4-dimethyl-2-(4'-methoxymethoxymethylbiphenyl-2-yl)oxazoline
(2) 4,4-dimethyl-2-(4'-methoxyethoxymethoxymethylbiphenyl- 2-yl)oxazoline
(3) 4,4-dimethyl-2-(4'-thiomethoxymethoxymethylbiphenyl- 2-yl)oxazoline
(4) 4,4-dimethyl-2-(4'-tetrahydropyranyloxymethylbiphenyl- 2-yl)oxazoline
(5) 4,4-dimethyl-2-(4-tetrahydrofuranyloxymethylbiphenyl-2-yl)oxazoline
(6) 4,4-dimethyl-2-(4'-trimethylsilyloxymethylbiphenyl-2-yl)oxazoline
(7) 4,4-dimethyl-2-(4'-2-butoxymethylbiphenyl-2-yl)oxazoline
(8) 4,4-dimethyl-2-(4'-benzyloxymethylbiphenyl-2-yl)oxazoline Further, the 4-bromobenzyl ether derivative (VI) according to the present invention has the following chemical structural formula:

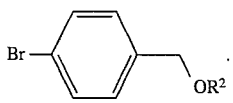

(VI)

In the formula, $R^2$ is as defined above. Further specific examples of the 4-bromobenzyl ether derivative (VI) include the following compounds, though the 4-bromobenzyl ether derivative (VI) according to the present invention is not limited to them.

(1) 4-bromobenzyl-methoxymethyl ether
(2) 4-bromobenzyl-methoxyethoxymethyl ether
(3) 4-bromobenzyl-thiomethoxymethyl ether
(4) 4-bromobenzyl-tetrahydropyranyl ether
(5) 4-bromobenzyl-tetrahydrofuranyl ether
(6) 4-bromobenzyl-trimethylsilyl ether
(7) 4-bromobenzyl-t-butyl ether
(8) 4-bromobenzyl-benzyl ether Further, the carboxy-biphenyloxazoline derivative (VII) according to the present invention has the following chemical structural formula:

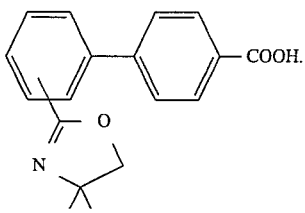

(VII)

Further specific examples of the carboxy-biphenyloxazoline derivative (VII) according to the present invention include the following compounds, though the derivative (VII) is not limited to them.

(1) 4,4-dimethyl-2-(4'-carboxybiphenyl-2-yl)oxazoline
(2) 4,4-dimethyl-2-(4'-carboxybiphenyl-3-yl)oxazoline
(3) 4,4-dimethyl-2-(4'-carboxybiphenyl-4-yl)oxazoline Further, the alkoxycarbonyl-biphenyloxazoline derivative (VIII) according to the present invention has the following chemical structural formula:

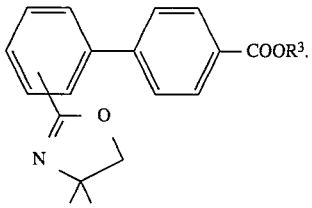

(VIII)

In the formula, $R^3$ represents a lower alkyl group, an aryl group, an aralkyl group, a cycloether group, a trialkylsilyl group a triarylsilyl group a vinyl group, a lower alkoxyalkyl group, an aryloxyalkyl group, an aralkyloxyalkyl group, a thioalkoxyalkyl group or a triphenylmethyl group. It is preferable that $R^3$ be a lower alkyl group, an aryl group, an aralkyl group, a cycloether group, a triarylsilyl group, a vinyl group, a lower alkoxyalkyl group, an aryloxyalkyl group, an aralkyloxyalkyl group, a thioalkoxyalkyl group or a triphenylmethyl group. Specific examples of the lower alkyl group include groups having 1 to 6 carbon atoms, such as a methyl group, an ethyl group, a propyl group, a butyl group, a pentyl group and a hexyl group; those of the aryl group include a phenyl group, a tolyl group and a xylyl group; those of the aralkyl group include a benzyl group and a phenethyl group; those of the cycloether group include a tetrahydropyranyl group and a tetrahydrofuranyl group; those of the triarylsilyl group include a trimethylsilyl group, a triethylsilyl group, a t-butyldimethylsilyl group, an i-propyldimethylsilyl group and a phenyldimethylsilyl group; those of the lower alkoxyalkyl group include a methoxymethyl group, an ethoxymethyl group, a propoxymethyl group, a methoxyethyl group, an ethoxyethyl group, a propoxyethyl group and a propoxypropyl group; those of the aryloxyalkyl group include a phenoxymethyl group, a phenoxyethyl group and a tolyloxymethyl group; those of the aralkyloxyalkyl group include a benzyloxymethyl group and a phenethyloxymethyl group; and those of the thioalkoxyalkyl group include a methylthiomethyl group, a methylthioethyl group, an ethylthiomethyl group, a phenylthiomethyl group and a benzylthiomethyl group.

Further specific examples of the alkoxycarbonyl-biphenyloxazoline derivative (VIII) include the following compounds, though the alkoxycarbonyl-biphenyloxazoline derivative (VIII) according to the present invention is not limited to them.

(1) 4,4-dimethyl-2-(4'-methoxycarbonylbiphenyl-2-yl)oxazoline (2) 4,4-dimethyl-2-(4'-ethoxycarbonylbiphenyl-2-yl)oxazoline
(3) 4,4-dimethyl-2-(4'-propoxycarbonylbiphenyl-2-yl)oxazoline
(4) 4,4-dimethyl-2-(4'-phenoxycarbonylbiphenyl-2-yl)oxazoline
(5) 4,4-dimethyl-2-(4'-benzyloxycarbonylbiphenyl-2-yl)oxazoline
(6) 4,4-dimethyl-2-(4'-tetrahydropyranyloxycarbonylbiphenyl- 2-yl)oxazoline Further, the methyl-biphenyloxazoline derivative (IX) according to the present invention has the following chemical structural formula:

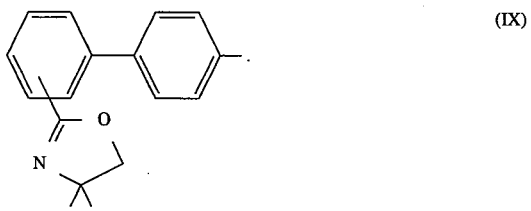
(IX)

Further, specific and representative examples of the methyl-biphenyloxazoline derivative (IX) according to the present invention include the following compounds, though the derivative (IX) is not limited to them.
(1) 4,4-dimethyl-2-(4'-methylbiphenyl-2-yl)oxazoline
(2) 4,4-dimethyl-2-(4'-methylbiphenyl-3-yl)oxazoline
(3) 4,4-dimethyl-2-(4'-methylbiphenyl-4-yl)oxazoline Next, each step of the process according to the present invention will be described in detail hereinafter (see the above reaction scheme-8).

Step 1

This step is one wherein 4-bromobenzyl alcohol is protected to obtain a 4-bromobenzyl ether derivative (VI). This step can be conducted according to the conventional process for introducing a protective group for a hydroxyl group in organic synthesis. Specific examples of the reagent for introducing a protective group usable in the present invention include chloromethyl methyl ether, 2-chloroethyl methyl ether, chloromethyl phenyl ether, chloromethyl benzyl ether, chloromethyl methoxyethyl ether, chloromethyl methyl sulfide, dihydropyrane, dihydrofuran, chlorotrimethylsilane, chlorotriethylsilane, chlorotriphenylsilane, methyl iodide, benzyl chloride and chlorotriphenylmethane.

Step 2

This step is one wherein the 4-bromobenzyl ether derivative (VI) is coupled with oxazolylanisole to form an alkoxymethyl-biphenyloxazoline derivative (V) through the Grignard reaction. This reaction can be conducted according to the conventional process for the Grignard reaction as described in, e.g., Journal of Organic Chemistry (J. Org. Chem.), 43 (7), 1372 to 1379, 1978.

Step 3

In this step, the protective group of the alkoxymethyl-biphenyloxazoline derivative (V) is eliminated to form a hydroxymethyl-biphenyloxazoline derivative (IV).

This reaction can be conducted according to a common process for eliminating the protective group such as hydrolysis and catalytic reduction. This reaction can be conducted according to a common process for eliminating the protective group such as hydrolysis and catalytic reduction.

Step 4

Step 4 is one wherein a methyl-biphenyloxazoline derivative (IX) is oxidized into a carboxy-biphenyloxazoline derivative (VII). In this reaction, an oxidizing agent is used, and specific examples thereof usable in the present invention include permanganates, chromium oxide and bichromates, among which permanganates are preferable. This reaction can be conducted according to the process described in, e.g., Organic Synthesis, Col. Vol. II, 135. In the present invention, the methyl-biphenyloxazoline derivative (IX) is dissolved in a solvent, a permanganate such as potassium permanganate is added thereto and the obtained mixture is heated.

Although the amount of the permanganate used is not limited, it is generally used in an amount of about 1 to 100 equivalents, more preferably about 2 to 50 equivalents, still preferably about 3 to 20 equivalents per equivalent of the methyl-biphenyloxazoline derivative (IX).

The solvent to be used in this reaction is not limited, so far as it is inert to the methyl-biphenyloxazoline derivative (IX) or the oxidizing agent. Specific examples thereof include water, pyridine, formic acid and acetic acid. The solvent may be used either alone or as a mixture of two or more of them. Although the amount of the solvent used is not limited, it is generally used in an amount of about 0.5 to 100 parts by volume, more preferably about 0.5 to 50 parts by volume, still preferably about 1.0 to 20 parts by volume based on 1 part by weight of the methyl-biphenyloxazoline derivative (IX).

This reaction is generally conducted under heating at a temperature ranging from 50° C. to the refluxing temperature of the solvent. Although the reaction time varies depending upon the kind or amount of the oxidizing agent, temperature or the like, it is generally completed in about 1 to 48 hours.

Steps 5 and 7

These steps are those wherein the carboxy-biphenyloxazoline derivative (VII) or the alkoxycarbonyl-biphenyloxazoline derivative (VIII) is reduced with a metal hydride complex into a hydroxymethyl-biphenyloxazoline derivative (IV). Specific examples of the metal hydride complex in the present invention include aluminum lithium hydride, bis(2-methoxyethoxy)aluminum sodium hydride, diisobutylaluminum hydride and diborane. Although the amount of the metal hydride complex used is not limited, it is generally used in an amount of about 0.2 to 50 equivalents, more preferably about 0.5 to 20 equivalents, still preferably about 1 to 10 equivalents per equivalent of the carboxy-biphenyloxazoline derivative (VII) or the alkoxycarbonyl-biphenyloxazoline derivative (VIII).

It is preferable to use a solvent in this reaction. The solvent usable is not limited, so far as it is inert to the carboxy-biphenyloxazoline derivative (VII) or the alkoxycarbonyl-biphenyloxazoline derivative (VIII), or the metal hydride complex. Specific examples thereof include tetrahydrofuran, 1,2-dimethoxyethane, ethyl ether, isopropyl ether, 2-methoxyethyl ether, dioxane, dioxolane, benzene, toluene, hexane and octane. The solvent may be used either alone or as a mixture of two or more of them. Although the amount of the solvent used is not limited, it is generally used in an amount of about 0.5 to 100 parts by volume, more preferably about 0.5 to 50 parts by volume, still preferably about 1.0 to 20 parts by volume based on 1 part by weight of the carboxy-biphenyloxazoline derivative (VII) or the alkoxycarbonyl-biphenyloxazoline derivative (VIII).

Although this reaction can be generally conducted at a temperature ranging from −70° C. to the refluxing temperature of the solvent, it is generally conducted under cooling with ice. Although the reaction time varies depending upon the kind or amount of the metal hydride complex, temperature or the like, it is generally completed in about 5 minutes to 6 hours.

Step 6

This step is one wherein the carboxy-biphenyloxazoline derivative (VII) obtained in step 4 is esterified into an alkoxycarbonyl-biphenyloxazoline derivative (VIII). This reaction can be conducted according to the common esterification process.

Step 8

This step is one wherein the protective group of the hydroxymethyl-biphenyloxazoline derivative (IV) is eliminated to form a hydroxymethyl-biphenylcarboxylic acid derivative (III). Although this reaction can be conducted by the conventional processes for hydrolyzing oxazoline into a carboxylic acid in organic synthesis, i.e., by acidic hydrolysis, basic hydrolysis, a process using methyl iodide and sodium hydroxide described in Journal of Organic Chemistry (J. Org. Chem.), 39(3), 2778, 1974, or a combination thereof, sulfuric acid hydrolysis, a combination of hydrochloric acid hydrolysis and sodium hydroxide hydrolysis, or the above process using methyl iodide and sodium hydroxide is preferable in the present invention.

Step 9

This step is one wherein the hydroxymethyl-biphenylcarboxylic acid derivative (III) is esterified into a hydroxymethyl-biphenylcarboxylic ester derivative (I). This reaction can be conducted according to the common esterification process.

Step 10

This step is one wherein the hydroxymethyl-biphenylcarboxylic ester derivative (I) is halogenated into a halomethyl-biphenylcarboxylic ester derivative (II). This reaction is conducted according to the conventional manner by the use of a reagent for halogenation such as hydrochloric acid, thionyl chloride, sulfuryl chloride, phosphorus trichloride, phosphorus pentachloride, phosphorus oxychloride, oxalyl chloride, phosgene, diphosgene, triphosgene, hydrobromic acid, thionyl bromide and phosphorus tribromide. Although the amount of the reagent for halogenation used is not limited, it is generally used in an amount of about 1 to 50 equivalents, preferably about 1.5 to 20 equivalents, still preferably about 2 to 10 equivalents per equivalent of the hydroxymethyl-biphenylcarboxylic ester derivative (I).

The halomethyl-biphenylcarboxylic ester derivative (II) according to the present invention is highly stable and can also be further purified by an ordinary method such as silica gel column chromatography and vacuum distillation.

Further, a (4'-chloromethylphenyl)benzoic ester (X) represented by the following general formula is a novel compound and is useful as an intermediate for the synthesis of a medicine:

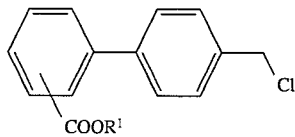

(X)

[wherein $R^1$ is as defined above].

Specific examples of the (4'-chloromethylphenyl)benzoic ester (X) include the following compounds, though the (4'-chloromethylphenyl)benzoic ester (X) according to the present invention is not limited to them.

(1) methyl 2-(4'-chloromethyl)benzoate
(2) methyl 3-(4'-chloromethyl)benzoate
(3) methyl 4-(4'-chloromethyl)benzoate
(4) ethyl 2-(4'-chloromethyl)benzoate
(5) ethyl 3-(4'-chloromethyl)benzoate
(6) ethyl 4-(4'-chloromethyl)benzoate
(7) propyl 2-(4'-chloromethyl)benzoate
(8) propyl 3-(4'-chloromethyl)benzoate
(9) propyl 4-(4'-chloromethyl)benzoate
(10) phenyl 2-(4'-chloromethyl)benzoate
(11) phenyl 3-(4'-chloromethyl)benzoate
(12) phenyl 4-(4'-chloromethyl)benzoate Preparative Examples for the raw materials and intermediates necessary for carrying out the present invention with now be described prior to Examples.

PREPARATIVE EXAMPLE 1

Synthesis of 4-bromobenzylmethoxymethyl ether

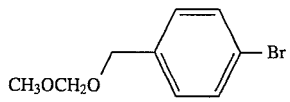

10.0 g (53.5 mmol) of 4-bromobenzyl alcohol was dissolved in tetrahydrofuran (200 ml). 6.6 g (58.8 mmol) of potassium t-butoxide was added thereto under cooling with ice, followed by stirring for one hour. Then, 5.2 g (64.6 mmol) of chloromethyl methyl ether was dropwise added thereto, followed by stirring at room temperature for 12 hours. The reaction liquid was added to a saturated aqueous solution of ammonium chloride, followed by the extraction with ethyl acetate. After washing with water and drying vacuum concentration was conducted. The residue was purified by silica gel column chromatography to give 11.0 g of the title compound as an oil (yield 89%).

$^1$H-NMR(90 MHz, CDCl$_3$); δ(ppm) 3.40(3H, s), 4.52(2H, s), 4.66(2H, s), 7.16(2H, d, g=8.0 Hz), 7.40(2H, d, J=8.0 Hz)

PREPARATIVE EXAMPLE 2

Synthesis of 4-bromobenzyltetrahydropylanyl ether

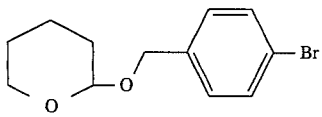

10.0 g (53.5 mmol) of 4-bromobenzyl alcohol and 4.95 g (58.8 mmol) of 3,4-dihydro-2H-pyrane were dissolved in methylene chloride (50 ml). Under cooling with ice, 100 mg of p-toluenesulfonic acid monohydrate was added thereto, followed by stirring for 3 hours. The reaction liquid was added to an aqueous solution of sodium hydrogencarbonate, followed by the extraction with chloroform. After washing with water and drying, vacuum concentration was conducted. The residue was subjected to vacuum distillation (160° C./1 mmHg) to give 12.0 g of the title compound as an oil (yield 83%).

$^1$H-NMR(90 MHz, CDCl$_3$); δ(ppm) 1.40~2.10 (6H, m), 3.38~3.70(1H, m), 3.70~4.02(1H, m), 4.41(1H, d, J=13.0 Hz), 4.64(1H, s), 4.70(1H, d, J=13.0 Hz), 7.18(2H, d, J=8.0 Hz), 7.44(2H, d, J=8.0 Hz)

PREPARATIVE EXAMPLE 3

Synthesis of 4,4-dimethyl-2-(4'-methylbiphenyl-2-yl)oxazoline

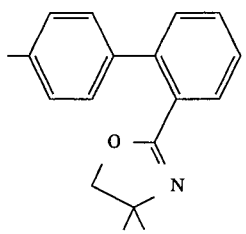

Tetrahydrofuran (200 ml) was added to 2.5 g (103 mmol) of flaky magnesium, followed by the addition of a small amount of dibromoethane under stirring. After the confirmation of bubbling, 13 ml (106 mmol) of 4-bromotoluene was dropwise added thereto. After the confirmation of the dissolution of the magnesium, the mixture was further stirred at room temperature for one hour. This reaction liquid was dropwise added to a solution of 10.0 g (48.7 mmol) of 4,4-dimethyl-2-( 2'-methoxyphenyl)oxazoline in tetrahydrofuran (100 ml), followed by stirring for 12 hours. The reaction liquid was poured into a saturated aqueous solution of ammonium chloride, followed by the extraction with chloroform. After washing with water and drying, vacuum concentration was conducted. The residue was purified by silica gel column chromatography (a n-hexane/ethyl acetate system) to give 11.0 g of the title compound as a crystal (yield 85%).

m.p.; 56°–59° C.

$^1$H-NMR(200 MHz, CDCl$_3$); δ(ppm, 1.30 (6H, s), 2.38 (3H, s), 3.80(2H, s), 7.00~7.50(7H, m), 7.70(1H, dd, J=7.5, 1.5 Hz)

FAB-MS; 266(MH$^+$)

Next, Examples will be given hereinafter to illustrate the present invention in definite, though it is needless to say that the present invention is not limited to them.

EXAMPLE 1

Synthesis of 4,4-dimethyl-2-(4'-methoxymethoxymethylbiphenyl-2-yl)oxazoline

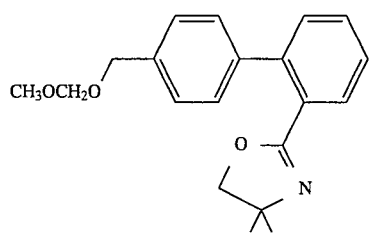

Tetrahydrofuran (15 ml) was added to 408 mg (16.8 mmol) of flaky magnesium, followed by the addition of a small amount of dibromoethane under stirring. After the confirmation of bubbling, a solution of 3.23 g (14.0 mmol) of 4-bromobenzyl-methoxymethyl ether in tetrahydrofuran (15 ml) was dropwise added thereto. After the confirmation of the dissolution of the magnesium, the resulting mixture was further stirred at room Temperature for one hour. Then, a solution of 2.10 g (10.2 mmol) of 4,4-dimethyl-2-(2'-methoxyphenyl)oxazoline in tetrahydrofuran (15 ml) was dropwise added thereto, followed by stirring for 12 hours. The reaction liquid was poured into a saturated aqueous solution of ammonium chloride, followed by the extraction with chloroform. After washing with water and drying, vacuum concentration was conducted. The residue was purified by silica gel column chromatography (a n-hexane/ ethyl acetate system) to give 3.20 g of the title compound as an oil (yield 96%).

$^1$H-NMR(400 MHz, CDCl$_3$); δ(ppm) 1.30(6H, s), 3.45(3H, s), 3.80(2H, s), 4.64(2H, s), 4.74(2H, s), 7.34~7.40(6H, m), 7.48(1H, ddd, J=8.5, 8.0, 1.5 Hz), 7.73(1H, dd, J=8.0, 1.5 Hz)

FAB-MS; 326(MH$^+$)

EXAMPLE 2

Synthesis of 4,4-dimethyl-2-(4'-tetrahydropyranyloxymethyl-biphenyl-2-yl)oxazoline

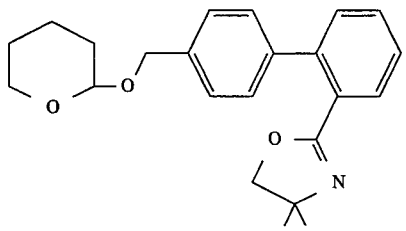

Tetrahydrofuran (15 ml) was added to 1.2 g (49.4 mmol) of flaky magnesium, followed by the addition of a small amount of dibromoethane under stirring. After the confirmation of bubbling, a solution of 11.0 g (40.6 mmol) of 4-bromobenzyl-tetrahydropyranyl ether in tetrahydrofuran (15 ml) was dropwise added thereto. After the confirmation of the dissolution of the magnesium, the resulting mixture was further stirred at room temperature for one hour. Then, a solution of 7.0 g (34.1 mmol) of 4,4-dimethyl-2-( 2'-methoxyphenyl)oxazoline in tetrahydrofuran (5 ml) was dropwise added thereto, followed by stirring for 12 hours. The reaction liquid was poured into a saturated aqueous solution of ammonium chloride, followed by the extraction with chloroform. After washing with water and drying, vacuum concentration was conducted. The residue was purified by silica gel column chromatography (a n-hexane/ethyl acetate system) to give 6.61 g of the title compound as an oil (yield 53%).

$^1$H-NMR(400 MHz, CDCl$_3$); δ(ppm) 1.29(6H, s), 1.50~1.94(6H, m), 3.52~3.59(1H, m), 3.80(2H, s), 3.91~3.97(1H, m), 4.55(1H, d, J=12.3 Hz), 4.73(1H, t, J=3.7 Hz), 4.84(1H, d, J=12.3 Hz), 7.38(4H, s), 7.34~7.40(2H, m), 7.48(1H, ddd, J=8.0, 7.5, 1.5 Hz), 7.72(1H, ddd, J=8.0, 1.5, 1.0 Hz)

FAB-MS; 366(MH$^+$)

EXAMPLE 3

Synthesis of
4,4-dimethyl-2-(4'-hydroxymethylbiphenyl-
2-yl)oxazoline

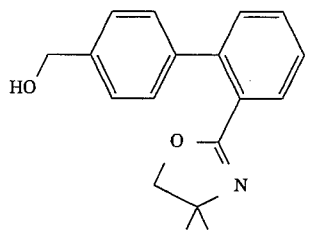

2.62 g (8.05 mmol) of 4,4-dimethyl-2-(4'-methoxymethoxymethylbiphenyl- 2-yl)oxazoline was dissolved in methanol (20 ml). 6N hydrochloric acid (10 ml) was added thereto, followed by stirring at 40° C. for 2 hours. The reaction liquid was poured into a saturated aqueous solution of sodium hydrogencarbonate, followed by the extraction with chloroform. After washing with water and drying vacuum concentration was conducted. The residue was purified by silica gel column chromatography (a n-hexane/ethyl acetate system) to give 2.20 g of the title compound as a crystal (yield 97%).

m.p.; 97°–100° C.

$^1$H-NMR(400 MHz, CDCl$_3$); δ(ppm) 1.30(6H, s), 1.75(1H, br-s), 3.80(2H, s), 4.75(2H, s), 7.40(4H, s), 7.35~7.42(2H, m), 7.48(1H, ddd, J=8.0, 7.5, 1.3 Hz), 7.73(1H, dd, J=8.1, 1.3 Hz)

EI-MS; 280(M-H$^+$)

EXAMPLE 4

Synthesis of
4,4-dimethyl-2-(4'-hydroxymethylbiphenyl-
2-yl)oxazoline 4.0 g (10.9 mmol) of 4,4-dimethyl-2-(4'-tetrahydropyranyloxymethylbiphenyl- 2-yl)oxazoline was dissolved in methanol (50 ml), and 6N hydrochloric acid (15 ml) was added thereto, followed by stirring at room temperature for 2 hours. The reaction liquid was poured into a saturated aqueous solution of sodium hydrogencarbonate, followed by the extraction with chloroform. After washing with water and drying, vacuum concentration was conducted. The residue was purified by silica gel column chromatography (a n-hexane/ethyl acetate system) to give 3.0 g of the title compound (yield 98%).

EXAMPLE 5

Synthesis of
4,4-dimethyl-2-(4'-carboxybiphenyl-2-yl)oxazoline

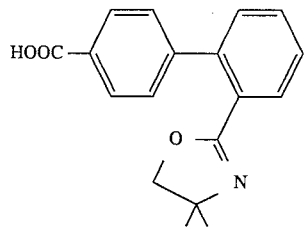

20.0 g (75.4 mmol) of 4,4-dimethyl-2-(4'-methylbiphenyl- 2-yl)oxazoline was dissolved in pyridine (75 ml) and water (150 ml), followed by the addition of 71.4 g (452 mmol) of potassium permanganate in portions under reflux by heating. After the completion of the addition, the obtained mixture was further refluxed for 4 hours. The reaction liquid was cooled and filtered to remove insolubles. After washing the residue with hot water, the filtrates were combined and subjected to vacuum concentration. The crystal which was precipitated by adding concentrated hydrochloric acid to the residue was recovered by filtration. 20.4 g of the title compound was obtained as a crystal (yield 92%).

m.p.; 190°–193° C.

$^1$H-NMR(600 MHz, CDCl$_3$); δ(ppm) 1.16(6H, s), 3.79(2H, s), 7.43~7.48(4H, m), 7.49 (1H, dt, J=7.5, 1.5 Hz), 7.58(1H, dd, J=7.5, 1.0 Hz), 7.96(2H, dd, J=8.6, 1.9 Hz), 2.90(1H, br)

FAB-MS; 296(MH$^+$)

EXAMPLE 6

Synthesis of
4,4-dimethyl-2-(4'-hydroxymethylbiphenyl-
2-yl)oxazoline 1.28 g (33.7 mmol) of aluminum lithium hydride was suspended in tetrahydrofuran (20 ml). At room temperature, 5.0 g (16.9 mmol) of 4,4-dimethyl-2-(4'-carboxybiphenyl-2-yl)oxazoline was gradually added thereto, followed by stirring for 2 hours. After the reaction liquid was cooled with ice, 100 ml of water was added thereto to conduct hydrolysis, followed by the extraction with chloroform. After washing with water and drying, vacuum concentration was conducted. The residue was purified by silica gel column chromatography (a n-hexane/ethyl acetate system) to give 4.2 g of the title compound (yield 88%).

EXAMPLE 7

Synthesis of
4.4-dimethyl-2-(4'-methoxycarbonylbiphenyl
-2-yl)oxazoline

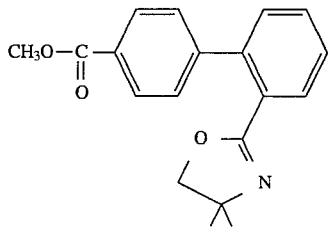

10.0 g (33.8 mmol) of 4,4-dimethyl-2-(4'-carboxybiphenyl- 2-yl)oxazoline was dissolved in methylene chloride (200 ml). 4.8 g (40.3 mmol) of thionyl chloride was added thereto, followed by stirring at room temperature for 2 hours. The reaction liquid was subjected to vacuum concentration. Methanol (100 ml) was added to the residue, followed by stirring for 3 hours. After distilling out the solvent under a reduced pressure, methylene chloride and a saturated aqueous solution of sodium hydrogencarbonate were added to the residue and obtained mixture was caused liquid-liquid separation. After washing with water and drying, vacuum concentration was conducted. The residue was purified by silica gel column chromatography (an ethyl acetate/n-hexane system) to give 9.53 g of the title compound as an oil (yield 91%).

¹H-NMR(400 MHz, CDCl₃); δ(ppm) 1.26(6H, s), 3.77(2H, s), 3.92(3H, s), 7.28~7.56(5H, m), 7.75(1H, d, J=8.5 Hz), 8.03(2H, d, J=7.5 Hz)

FAB-MS; 310(MH⁺)

EXAMPLE 8

Synthesis of 4,4-dimethyl-2-(4'-hydroxymethylbiphenyl-2-yl)oxazoline 2.0 g (6.48 mmol) of 4,4-dimethyl-2-(4'-methoxycarbonylbiphenyl- 2-yl)oxazoline was dissolved in tetrahydrofuran (20 ml). 0.49 g (12.9 mmol) of aluminum lithium hydride was gradually added thereto under cooling with ice, followed by the stirring for 2 hours as such. Water (50 ml) was added thereto to conduct hydrolysis, followed by the extraction with chloroform. After washing with water and drying, vacuum concentration was conducted. The residue was purified by silica gel column chromatography (a n-hexane/ethyl acetate system) to give 1.69 g of the title compound (yield 93%).

EXAMPLE 9

Synthesis of 4,4-dimethyl-2-(4'-chloromethylphenyl-2-yl)oxazoline

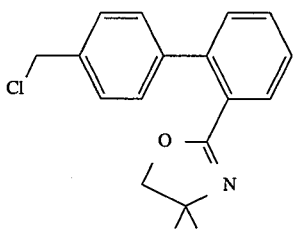

1.0 g (3.55 mmol) of 4,4-dimethyl-2-(4'-hydroxymethylbiphenyl- 2-yl)oxazoline was dissolved in methylene chloride (15 ml). Under cooling with ice, 0.51 g (4.29 mmol) of thionyl chloride was dropwise added thereto, followed by stirring for one hour. The reaction liquid was poured into an aqueous solution of sodium hydrogencarbonate, followed by the extraction with methylene chloride. After washing with water and drying, vacuum concentration was conducted. 1.05 g of the title compound was obtained as a crystal (yield 99%).

m.p.; 72°–75° C.

¹H-NMR(400 MHz, CDCl₃); δ(ppm) 1.29(6H, s), 3.80(2H, s), 4.64(2H, s), 7.35~7.43(6H, m), 7.62(1H, td, J=7.6, 1.5 Hz), 7.73(1H, ddd, J=7.6, 1.S, 1.0 Hz)

FAB-MS; 300(MH⁺)

EXAMPLE 10

Synthesis of 4,4-dimethyl-2-(4'-methanesulfonyloxymethylbiphenyl-2-yl)oxazoline

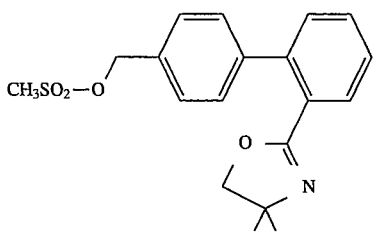

2.0 g (7.1 mmol) of 4,4-dimethyl-2-(4'-hydroxymethylbiphenyl- 2-yl)oxazoline and 1.43 g (14.1 mmol) of triethylamine were dissolved in methylene chloride (20 ml). A solution of 0.98 g (8.6 mmol) of methanesulfonyl chloride in methylene chloride (10 ml) was dropwise added thereto under cooling with salt-ice. After stirring for 3 hours as such, the reaction liquid was poured into water, followed by the extraction with methylene chloride. After washing with water and drying, vacuum concentration was conducted. 2.53 g of the title compound was obtained as an oil (yield 99%).

¹H-NMR (90 MHz, CDCl₃); δ(ppm) 1.31(6H, s), 2.94(3H, s), 3.80(2H, s), 6.26(2H, s), 7.40(4H, s), 7.14~7.80(4H, m)

EXAMPLE 11

Synthesis of 4,4-dimethyl-2-(4'-p-toluenesulfonyloxymethyl-biphenyl-2-yl) oxazoline

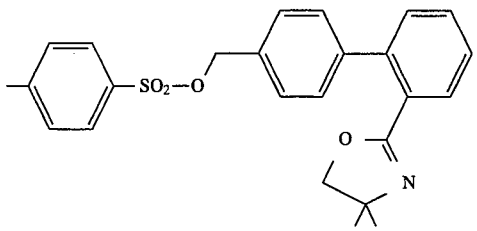

0.34 g (8.5 mmol) of a 60% oily sodium hydride was suspended in tetrahydrofuran (20 ml). A solution of 2.0 g (7.1 mmol) of 4,4-dimethyl-2-(4'-hydroxymethylbiphenyl-2-yl)oxazoline in tetrahydrofuran (30 ml) was dropwise added thereto at room temperature, followed by further stirring at room temperature for one hour. After the reaction liquid was cooled with ice, a solution of 1.6 g (8.4 mmol) of p-toluenesulfonyl chloride in tetrahydrofuran (20 ml) was dropwise added thereto. After stirring for 3 hours as such, the reaction liquid was poured into a saturated aqueous solution of ammonium chloride, followed by the extraction with chloroform. After washing with water and drying, vacuum concentration was conducted. The residue was purified by silica gel column chromatography (a n-hexane/ethyl acetate system) to give 1.7 g of the title compound as an oil (yield 55%).

¹H-NMR(90 MHz, CDCl₃); δ(ppm) 1.28(6H, s), 2.24(3H, s), 3.76(2H, s), 5.07(2H, s), 7.11~7.70(10H, m), 7.78(2H, d, J=8 Hz)

FAB-MS; 436 (MH⁺)

EXAMPLE 12

Synthesis of 2-(4'-hydroxymethylphenyl)benzoic acid

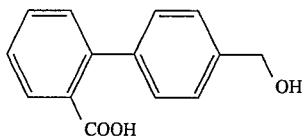

2.0 g (7.11 mmol) of 4,4-dimethyl-2-(4'-hydroxymethyl-biphenyl- 2-yl)oxazoline was dissolved in methylene chloride (10 ml). 3.0 g (21.1 mmol) of methyl iodide was added thereto, followed by stirring for 12 hours. After the reaction liquid was concentrated to dryness, methanol (20 ml) and a 20% aqueous solution of sodium hydroxide (20 ml) was added thereto, followed by heating under reflux For 13 hours. After cooling to room temperature and adjusting to pH 6 with hydrochloric acid, the resulting mixture was extracted with chloroform. After washing with water and drying, vacuum concentration was conducted. The residue was purified by silica gel column chromatography (a chloroform/methanol system) to give 1.24 g of the title compound as a crystal (yield 77%).

m.p.; 140°–142° C.

$^1$H-NMR(90 MHz, CDCl$_3$): δ(ppm) 4.70(2H, s), 5.25(1H, br-s). 7.20~7.82(7H, m), 7.50(1H, dd, J=7.6, 1.5Hz)

FAB-MS; 228 (M$^+$)

EXAMPLE 13

Synthesis of 2-(4'-hydroxymethylphenyl)benzene acid 2.0 g (7.11 mmol) of 4,4-dimethyl-2-(4'-hydroxymethyl-biphenyl- 2-yl)oxazoline was dissolved in ethanol (30 ml). 2N hydrochloric acid (10 ml) was added thereto, followed by heating under reflux for 3 hours. After the reaction liquid was cooled and concentrated, a saturated aqueous solution of sodium hydrogencarbonate (100 ml) was added thereto, followed by the extraction with chloroform. After the organic phase was washed with water and dried, it was subjected to vacuum concentration. A 20% aqueous solution of sodium hydroxide (20 ml) and ethanol (20 ml) were added to the residue, followed by heating under reflux for 8 hours. After the reaction liquid was cooled to room temperature and adjusted to pH 6 with hydrochloric acid, it was extracted with chloroform. After the organic phase was washed with water and dried, it was subjected to vacuum concentration. The residue was purified by silica gel column chromatography (a chloroform/methanol system) to give 1.31 g of the title compound (yield 81%).

EXAMPLE 14

Synthesis of 2-(4'-hydroxymethylphenyl)benzoic acid

Water (6 ml) and sulfuric acid (3.6 g) were added to 2.0 g (7.11 mmol) of 4,4-dimethyl-2-(4'-hydroxymethylbiphenyl- 2-yl)oxazoline, followed by heating under reflux for 30 hours. After the reaction liquid was cooled, it was neutralized with a 10% aqueous solution of sodium hydroxide and extracted with chloroform. After the organic phase was washed with water and dried, it was subjected to vacuum concentration. The residue was purified by silica gel column chromatography (a chloroform/methanol system) to give 1.05 g of the title compound (yield 65%).

EXAMPLE 15

Synthesis of methyl 2-(4'-hydroxymethylphenyl)benzoate

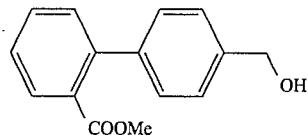

4.0 g (17.5 mmol) of 2-(4'-hydroxymethylphenyl)benzoic acid was dissolved in methanol (50 ml). Sulfuric acid (1 ml) was added thereto, followed by heating under reflux for 8 hours. After conducting vacuum concentration, water was added thereto, followed by the extraction with chloroform. After the organic phase was washed with water and dried, it was subjected to vacuum concentration. The residue was purified by silica gel column chromatography (a n-hexane/ethyl acetate system) to give 3.8 g of the title compound as an oil (yield 89%).

$^1$H-NMR(400 MHz, CDCl$_3$); δ(ppm) 1.60(1H, br-s), 3.64(3H, s), 4.72(2H, s), 7.29(2H, d, J=8.0 Hz), 7.33(1H, dd, J=7.7, 1.4 Hz), 7.38(1H, td, J=7.7, 1.4 Hz), 7.39(2H, d, J=8.0 Hz), 7.51(1H, td, J=7.7, 1.4 Hz), 7.81(1H, dd, J:7.7, 1.4 Hz)

FAB-MS; 242 (M$^+$)

EXAMPLE 16

Synthesis of methyl 2-(4'-methanesulfonyloxymethylphenyl)benzoate

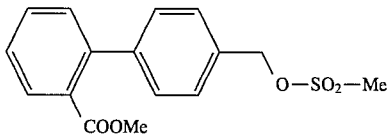

10.0 g (41 mmol) of methyl 2-(4'-hydroxymethylphenyl-)benzoate and 8.4 g (83.0 mmol) of triethylamine were dissolved in methylene chloride (150 ml). Under cooling with ice, a solution of 5.7 g (50 mmol) of methanesulfonyl chloride in methylene chloride (25 ml ) was dropwise added thereto, followed by further stirring for one hour. The reaction liquid was poured into water, followed by the extraction with methylene chloride. After the organic phase was washed with water and dried, it was subjected to vacuum concentration. 13.1 g of the title compound was obtained as a wax (yield 100%).

m.p.; 43°–45° C.

$^1$H-NMR(90 MHz, CDCl$_3$); δ(ppm) 2.96(3H, s), 3.64(3H, s), 5.25(2H, s), 7.20–7.60(7H, m), 7.72–7.90(1H, m)

EXAMPLE 17

Synthesis of methyl 2-(4'-p-toluenesulfonyloxymethylphenyl)benzoate

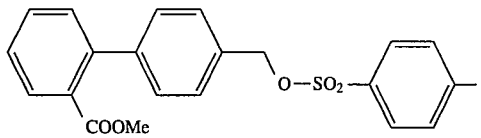

10.0 g (41 mmol) of methyl 2-(4'-hydroxymethylphenyl)benzoate was dissolved in tetrahydrofuran (200 ml). 2.0 g (50 mmol) of a 60% sodium hydride was added thereto under cooling with ice, followed by stirring for one hour. A solution of 8.65 g (45.4 mmol) of p-toluenesulfonyl chloride in tetrahydrofuran (50 ml) was dropwise added thereto. Then, the reaction was effected at room temperature for 2 hours and further reflux by heating was effected for 4 hours. The reaction liquid was cooled and added to a saturated aqueous solution of ammonium chloride. The resulting mixture was extracted with chloroform (200 ml). After the organic phase was washed with water and dried, it was subjected to vacuum concentration. The residue was purified by silica gel column chromatography (a n-hexane/ethyl acetate system) to give 13.4 g of the title compound as a wax (yield 82%).

$^1$H-NMR(90 MHz, CDCl$_3$): δ(ppm) 2.44(3H, s), 3.60(3H, s), 5.07(2H, s), 7.23(4H, s), 7.34(2H, d, J=7.7 Hz), 6.96–7.60(3H, m), 7.77(2H, d, J=7.7 Hz), 7.64–7.90(1H, m)

EXAMPLE 18

Synthesis of methyl 2-(4'-bromomethylphenyl)benzoate

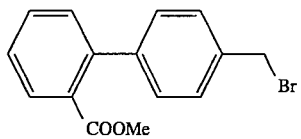

10.0 g (41 mmol) of methyl 2-(4'-hydroxymethylphenyl)benzoate was dissolved in 7.9 g of pyridine and n-hexane (100 ml). 8.3 g (31 mmol) of phosphorus tribromide was dropwise added thereto under cooling with ice, followed by stirring for 2 hours as such. The reaction liquid was added to an aqueous solution of sodium hydrogencarbonate, followed by the extraction with n-hexane. The organic phase was washed with water, dried and subjected to vacuum concentration. The residue was purified by silica gel column chromatography (a n-hexane/ethyl acetate system) to give 9.5 g of the title compound (yield 75%).

m.p.; 50°–51° C.

$^1$H-NMR(90 MHz, CDCl$_3$); δ(ppm) 3.62(3H, s), 5.01(2H, s), 7.12–7.60(7H, m), 7.68–7.85(1H, m)

FAB-MS; 305, 307(MH$^+$)

EXAMPLE 19

Synthesis of methyl 2-(4'-bromomethylphenyl)benzoate 2.0 g (8.8 mmol) of methyl 2-(4'-methylphenyl)benzoate 1.6 g (9.0 mmol) of N-bromosuccinimide and 0.05 g of α,α-azobis(isobutyronitrile) [another name; 2,2'-azobis(isobutyronitrile)] were dissolved in carbon tetrachloride (110 ml), followed by heating under reflux for 2 hours. The resultant mixture was filtered to remove insolubles, and then vacuum concentration was effected. The residue was recrystallized from a n-hexane/isopropyl ether mixed solvent to give 1.6 g of the title compound (yield: 59%).

EXAMPLE 20

Synthesis of methyl 2-(4'-chloromethylphenyl)benzoate

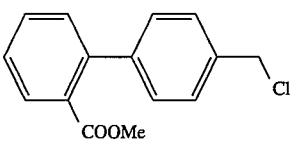

4.8 g (40.8 mmol) of thionyl chloride was dropwise added to a solution of 5.0 g (20.6 mmol) of methyl 2-(4'-hydroxymethylphenyl)benzoate in methylene chloride (50 ml) under cooling with ice. After the completion of the dropwise adding, the obtained mixture was brought to room temperature and stirred for 4.5 hours. After a saturated aqueous solution (150 ml) of sodium hydrogencarbonate was dropwise added to the reaction liquid, the obtained mixture was extracted twice with ethyl acetate (150 ml, 100 ml). The organic phases were combined and washed with water. The resultant organic phase was dried over anhydrous magnesium sulfate and subjected to vacuum concentration to give 5.8 g of an oily residue. This crude product was purified by silica gel column chromatography (a n-hexane/ethyl acetate system) to give 4.9 g of the title compound (yield; 91%).

$^1$H-NMR(400 MHz, CDCl$_3$): δ(ppm) 3.65(3H, s), 4.64(2H, s), 7.30(2H, d, J=7.5 Hz), 7.36(1H, dd, J=7.8, 1.5 Hz), 7.40–7.44(3H, m). 7.53(1H, td, J=7.8, 1.4 Hz), 7.85(1H, d, J=8.3 Hz)

FAB-MS: 261(MH$^+$)

EXAMPLE 21

Synthesis of methyl 2-(4'-chloromethylphenyl)benzoate 2.0 g (8.25 mmol) of methyl 2-(4'-hydroxymethylphenyl)benzoate was dissolved in 1.31 g of pyridine and methylene chloride (20 ml). 1.47 g (12.4 mmol) of thionyl chloride was dropwise added thereto at room temperature, followed by stirring as such for 16 hours and under reflux by heating for 5 hours. After the reaction liquid was cooled and concentrated, a saturated aqueous solution of sodium hydrogencarbonate was added thereto, followed by the extraction with methylene chloride. The organic phase was washed with water, dried and subjected to vacuum concentration. The residue was purified by silica gel column chromatography (a n-hexane/ethyl acetate system) to give 1.89 g of the title compound as an oil (yield 88%).

EXAMPLE 101

Synthesis of 2-cyclopropanecarboxamido-5-bromo-4-methyl-3-nitropyridine

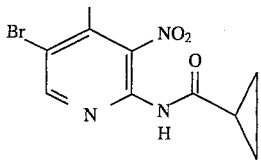

A mixture comprising 10 g (43.1 mmol) of 2-amino-5-bromo-4-methyl-3-nitropyridine, 6.3 g of 4-dimethylaminopyridine and xylene (50 ml) was heated at 110° C. in a nitrogen atmosphere. 5 g (47.4 mmol) of cyclopropanecarbonyl chloride was dropwise added thereto, followed by further stirring at 110° C. for 2 hours. The reaction mixture was brought to room temperature, followed by the addition of dichloromethane (200 ml) and water (50 ml). The organic phase was separated and the aqueous phase was further extracted with dichloromethane (50 ml). The organic phases were combined and washed with water (50 ml). The resulting organic phase was dried over anhydrous magnesium sulfate and concentrated to give a crude crystal. It was recrystallized from chloroform/ethyl acetate to give 11.4 g of the title compound (yield 88%).

m.p.; 204.7° C.

$^1$H-NMR (400 MHz, CDCl$_3$); δ(ppm) 0.91~0.96 (2H, m), 1.12~1.16 (2H, m), 1.59~1.71 (1H, m), 2.52 (3H, s), 8.21 (1H, br-s), 8.58 (1H, S)

FAB-MS; 300, 302 (MH$^+$)

EXAMPLE 102

Synthesis of 2-cyclopropanecarboxamido-4-methyl-3-nitropyridine

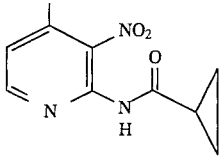

A mixture comprising 5.0 g (32.6 mmol) of 2-amino-4-methyl-3-nitropyridine and 5.2 g of pyridine was heated at 110° C. in a nitrogen atmosphere. 3.8 g (36 mmol) of cyclopropanecarbonyl chloride was dropwise added thereto, followed by further stirring at 110° C. for 5 hours. The reaction mixture was brought to room temperature, followed by the addition of chloroform (50 ml) and water (50 ml). The organic phase was separated and the aqueous phase was further extracted with chloroform (50 ml) twice. The organic phases were combined and washed with water (20 ml) and a saturated aqueous solution (20 ml) of common salt, successively. The resultant organic phase was dried over anhydrous magnesium sulfate and concentrated. The residue was purified by silica gel column chromatography (a n-hexane/ethyl acetate system) to give 5.4 g of the title compound (yield 75%).

m.p.; 179° C.

$^1$H-NMR (400 MHz, CDCl$_3$); δ(ppm) 0.89~0.94 (2H, m), 1.11~1.15 (2H, m), 1.67~1.73 (1H, m), 2.49 (3H, d, J=0.6 Hz), 7.08 (1H, dd, J=5.0, 0.6 Hz), 8.36 (1H, d, J=5.0 Hz). 8.61 (1H, br-s)

FAB-MS; 222 (MH$^+$)

EXAMPLE 103

Synthesis of 2-cyclopropanecarboxamido-4-methyl-3-nitropyridine

Toluene (60 ml) was added to 3.0 g (10.0 mmol) of 5-bromo-2-cyclopropanecarboxamido-4-methyl-3-nitropyridine, 10% Pd-C (100 mg) and 2.9 g (28.6 mmol) of triethylamine, followed by stirring and heating under reflux. 1.9 g (41.8 mmol) of formic acid was dropwise added to this solution, followed by stirring for 5 hours. The reaction liquid was brought to room temperature and filtered to remove the catalyst. The filtrate was subjected to vacuum concentration. Chloroform (100 ml) and water (100 ml) were added to the residue and the obtained mixture was caused liquid-liquid separation. The aqueous phase was further extracted with chloroform (50 ml) once. The organic phases were combined, dried over anhydrous magnesium sulfate and subjected to vacuum concentration. The residue was purified by silica gel column chromatography (a n-hexane/ethyl acetate system) to give 1.6 g of the title compound (yield 72%).

EXAMPLE 104

Synthesis of 2-[N-(2'-methoxycarbonylbiphenyl-4-yl)methyl]cyclopropanecarboxamido-5-bromo-4-methyl-3-nitropyridine

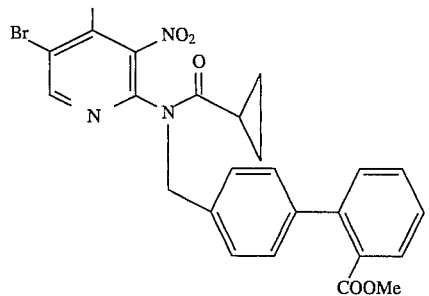

0.95 g (3.17 mmol) of 2-cyclopropanecarboxamido-5-bromo-4-methyl-3-nitropyridine was added to a solution of 0.40 g (3.56 mmol) of potassium t-butoxide in tetrahydrofuran (15 ml), followed by stirring at room temperature for 30 minutes. Then, this solution was heated, and a solution of 0.91 g (3.49 g) of methyl 2-(4'-chloromethylphenyl)benzoate in tetrahydrofuran (10 ml) was dropwise added thereto under reflux. After the completion of the dropwise addition, the obtained mixture was stirred under reflux for 23 hours. The reaction liquid was brought To room temperature, and a saturated aqueous solution (30 ml) of ammonium chloride and ethyl acetate (20 ml) were added thereto to conduct extraction. The aqueous phase was further extracted twice with ethyl acetate (20 ml×2). The organic phases were combined, washed with water and dried over anhydrous magnesium sulfate, and then subjected to vacuum concentration to give 1.25 g of an oily residue. This crude product was purified by silica gel column chromatography (a n-hexane/ethyl acetate system) to give 1.01 g of the title compound (yield; 61%).

¹H-NMR(300 MHz, CDCl₃); δ(ppm) 0.70~0.85(2H, br), 1.00~1.20(2H, br), 1.56(1H, br), 2.43(3H, s), 3.60(3H, s), 5.00~5.40(2H, br), 7.00~7.45(4H, br), 7.33(1H, dd, J=7.7, 1.1 Hz), 7.37(1H, ddd, J=7.7, 7.7, 1.1 Hz), 7.49(1H, ddd, J=7.7, 7.7, 1.1 Hz), 7.78(1H, dd, J=7.7, 1.1 Hz), 8.67(1H, s)

FAB-MS; 524, 526(MH⁺)

EXAMPLE 105

Synthesis of 2-[N-(2'-methoxycarbonylbiphenyl-4-yl)methyl]cyclopropanecarboxamido-5-bromo-4-methyl-3-nitropyridine 7.0 g (23 mmol) of 2-cyclopropanecarboxamido-5-bromo- 4-methyl-3-nitropyridine was added to a solution of 3.14 g (28 mmol) of potassium t-butoxide in tetrahydrofuran (80 ml), followed by stirring at room temperature for one hour. Then, this solution was heated. A solution of 8.5 g (28 mmol) of methyl 2-(4'-bromomethylphenyl)benzoate in tetrahydrofuran (50 ml) was dropwise added thereto under reflux by heating, followed by stirring for 1.5 hours after the completion of the dropwise addition. The reaction mixture was brought to room temperature. Ethyl acetate (200 ml) and a saturated aqueous solution (100 ml) of ammonium chloride were added thereto to conduct extraction. The aqueous phase was further extracted with ethyl acetate (100 ml) twice. The organic phases were combined and washed with a saturated aqueous solution of common salt. The resultant organic phase was dried over anhydrous magnesium sulfate and subjected to vacuum concentration to give 13.3 g of an oily substance. This crude substance was purified by silica gel column chromatography (a n-hexane/ethyl acetate system) to give 9.2 g of the title compound (yield 75%).

EXAMPLE 106

Synthesis of 2-[N-(2'-methoxycarbonyl]-biphenyl-4-yl)methyl]cyclopropanecarboxamido-5-bromo-4-methyl-3-nitropyridine 6.0 g (20 mmol) of 2-cyclopropanecarboxamido-5-bromo-4-methyl-8-nitropyridine was added to a solution of 2.47 g (22 mmol) of potassium t-butoxide in tetrahydrofuran (100 ml), followed by stirring at room temperature for one hour. A solution of 7.0 g (22 mmol) of methyl 2-(4'-methanesulfonyloxymethylphenyl)benzoate in tetrahydrofuran (60 ml) was dropwise added thereto under reflux by heating, followed by the reaction as such for 3 hours. The reaction liquid was cooled and added to a saturated aqueous solution of ammonium chloride, followed by the extraction with chloroform. After the organic phase was washed with water and dried, it was subjected to vacuum concentration. The residue was purified by silica gel column chromatography (a n-hexane/ethyl acetate system) to give 8.4 g of the title compound (yield 80%).

EXAMPLE 107

Synthesis of 2-[N-(2'-methoxycarbonylbiphenyl-4-yl)methyl]cyclopropanecarboxamido-5-bromo-4-methyl-3-nitropyridine 7.5 g (25 mmol) of 2-cyclopropanecarboxamido-5-bromo- 4-methyl-3-nitropyridine was added to a solution of 3.14 g (28 mmol) of potassium t-butoxide in tetrahydrofuran (100 ml), followed by stirring at room temperature for 45 minutes. A solution of 11.1 g (28 mmol) of methyl 2-(4'-p-toluenesulfonyloxymethylphenyl)benzoate in tetrahydrofuran (50 ml) was dropwise added thereto under reflux by heating, followed by the reaction as such for 4 hours. After the reaction liquid was cooled, it was added to a saturated aqueous solution of ammonium chloride, followed by the extraction with chloroform. After the organic phase was washed with water and dried, it was subjected to vacuum concentration. The residue was purified by silica gel column chromatography (a n-hexane/ethyl acetate system) to give 11.3 g of the title compound (yield 86%).

EXAMPLE 108

Synthesis of 2-[N-cyclopropanecarbonyl-N-{2'-(4",4"-dimethyl-oxazolin-2"-yl)biphenyl-4-yl}-methyl]amino-5-bromo-4-methyl-3-nitropyridine

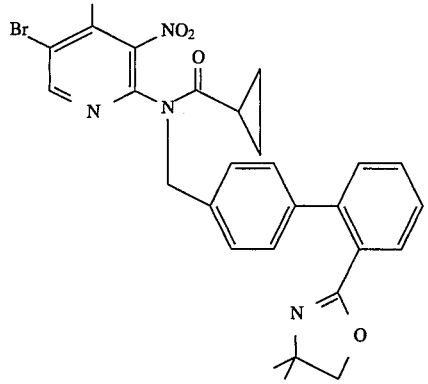

1.80 g (6.0 mmol) of 2-cyclopropanecarboxamido-5-bromo- 4-methyl-3-nitropyridine was added to a solution of 0.80 g (7.1 mmol) of potassium t-butoxide in tetrahydrofuran (15 ml). After stirring at room temperature for one hour, 0.45 (3.0 mmol) of sodium iodide and N,N-dimethylformamide (10 ml) were added thereto. Then, a solution of 2.50 g (8.3 mmol) of 4,4-dimethyl-2-(4'-chloromethyl-biphenyl-2-yl)oxazoline in tetrahydrofuran (20 ml) was dropwise added thereto under reflux by heating, followed by stirring as such for 13 hours. The reaction liquid was cooled and added to a saturated aqueous solution of ammonium chloride, followed by the extraction with chloroform. After washing with water and drying, vacuum concentration was conducted. The residue was purified by silica gel column chromatography (a n-hexane/ethyl acetate system) to give 2.73 g of the title compound (yield 81%).

1H-NMR (400 MHz, CDCl₃); δ(ppm) 0.74~0.79 (2H, m), 1.07~1.12 (2H, m), 1.23 (6H, s), 1.55~1.65 (1H, m), 2.43 (3H, s), 3.77 (2H, s), 4.50~5.40 (2H, br), 7.25~7.40 (6H, m), 7.46 (1H, td, J=8.0, 1.0 Hz), 7.72 (1H, d, J=8.0 Hz), 8.66 (1H, s)

FAB-MS; 563, 565 (MH⁺)

EXAMPLE 109

Synthesis of 2-[N-cyclopropanecarbonyl-N'-{{2'-(4",4"-dimethyl-oxazolin-2"-yl)biphenyl-4-yl}-methyl]amino-5-bromo-4-methyl-3-nitropyridine 1.52 g (5.1 mmol) of 2-cyclopropanecarboxamido-5-bromo-4-methyl-3-nitropyridine was added to a solution of 0.74 g (6.6 mmol) of potassium t-butoxide in tetrahydrofuran (10 ml), followed by stirring at room temperature for 1 hour. Then, a solution of 2.4 g (6.7 mmol) of 4,4-dimethyl-2-(4'-methanesulfonyloxymethylbiphenyl- 2-yl)oxazoline in dimethylsulfoxide (10 ml) was dropwise added thereto under reflux by heating, followed by stirring as such for 3 hours. The reaction mixture was cooled and added to a saturated aqueous solution of ammonium chloride, followed by the extraction with chloroform. After washing with water and drying, vacuum concentration was conducted. The residue was purified by silica gel column chromatography (a n-hexane/ethyl acetate system) to give 1.26 g of the title compound (yield 44%).

EXAMPLE 110

Synthesis of 2-[N-cyclopropanecarbonyl-N-{2'-(4",4"-dimethyloxazolin-2"-yl)biphenyl-4-yl}-methyl]amino-5-bromo-4-methyl-3-nitropyridine 1.50 g (5.0 mmol) of 2-cyclopropanecarboxamido-5-bromo- 4-methyl-3-nitropyridine was added to a solution of 0.67 g (6.0 mmol) of potassium t-butoxide in tetrahydrofuran (10 ml), followed by stirring at room temperature for 45 minutes. Then, a solution of 2.60 g (6.0 mmol) of 4,4-dimethyl-2-(4'-p-toluenesulfonyloxymethylbiphenyl-2-yl)oxazoline in tetrahydrofuran (20 ml) was dropwise added thereto under reflux by heating, followed by stirring as such for 4 hours. The reaction liquid was cooled and poured into a saturated aqueous solution of ammonium chloride, followed by the extraction with chloroform. The aqueous phase was further extracted with chloroform (100 ml) twice After washing with water and drying, vacuum concentration was conducted. The residue was purified by silica gel column chromatography (an ethyl acetate/n-hexane system) to give 1.40 g of the title compound (yield 50%).

EXAMPLE 111

Synthesis of 2-[N-cyclopropanecarbonyl-N-{2'-(4",4"-dimethyloxazolin-2"-yl)biphenyl-4-yl}-methyl]amino-5-bromo-4-methyl-3-nitropyridine 1.5 g (5.0 mmol) of 2-cyclopropanecarboxamido-5-bromo- 4-methyl-3-nitropyridine, 1.4 g (5.0 mmol) of 4,4-dimethyl-2-(4'-hydroxymethylbiphenyl-2-yl)oxazoline and 0.89 g (5.0 mmol) of diethyl azodicarboxylate were dissolved in tetrahydrofuran (30 ml). After cooling to −70° C. and stirring for 2 hours, a solution of 1.3 g (5.0 mmol) of triphenylphosphine in tetrahydrofuran (20 ml) was dropwise added thereto. After stirring as such at −70° C. for 2 hours, it was stirred at room temperature for 12 hours and further at 50° C. for 5 hours. The solvent was distilled off under a reduced pressure, ether (10 ml) was added to the residue, and the crystal thus precipitated was filtered out. The filtrate was subjected to vacuum concentration. The residue was purified by silica gel column chromatography (a n-hexane/ethyl acetate system) to give 2.0 g of the title compound (yield 71%).

EXAMPLE 112

Synthesis of 2-[N-(2'-methoxycarbonylbiphenyl-4-yl)methyl]cyclopropanecarboxamido-4-methyl-3-nitropyridine

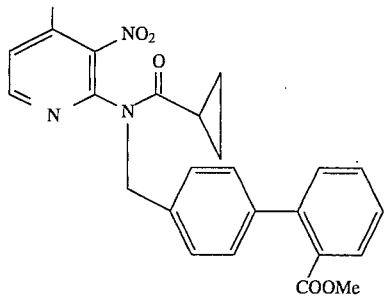

2.0 g (9 mmol) of 2-cyclopropanecarboxamido-4-methyl-3-nitropyridine was added Go a solution of 1.23 g (11 mmol) of potassium t-butoxide in tetrahydrofuran (30 ml), followed by stirring at room temperature for one hour. Then, this solution was heated, and a solution of 8.5 g (28 mmol) of methyl 2-(4'-bromomethylphenyl)benzoate in tetrahydrofuran (20 ml) was dropwise added thereto under reflux, followed by stirring for 2 hours after the completion of the dropwise addition. The reaction mixture was brought to room temperature, and chloroform (200 ml) and a saturated aqueous solution of ammonium chloride (200 ml) were added thereto to conduct extraction. The aqueous phase was further extracted with chloroform (50 ml) twice. The organic phases were combined, dried over anhydrous magnesium sulfate and subjected to vacuum concentration. The residue was purified by silica gel column chromatography (a n-hexane/ethyl acetate system) to give 3.4 g of the title compound (yield 84%).

$^1$H-NMR (600 MHz, CDCl$_3$); δ(ppm) 0.62–0.75 (2H, br), 0.98–1.11 (2H, br), 1.51 (1H, br-s), 2.36 (3H, s), 3.55 (3H, s), 5.10 (2H, br-s), 7.00–7.34 (5H, m), 7.28 (1H, d, J=7.5 Hz), 7.32 (1H, dd, J=7.5, 7.5 Hz), 7.43 (1H, dd, J=7.5, 7.5 Hz), 7.72 (1H, d, J=7.5 Hz), 8.42 (1H, br-s)

FAB-MS; 446 (MH$^+$)

EXAMPLE 113

Synthesis of 2-[N-(2'-methoxycarbonylbiphenyl-4-yl)methyl]cyclopropanecarboxamido-4-methyl-3-nitropyridine Toluene (100 ml) was added to 5.0 g (9.53 mmol) of 2-[N-(2'-methoxycarbonylbiphenyl-4-yl)methyl] -cyclopropanecarboxamido-5-bromo-4-methyl-3-nitropyridine, 10% Pd-C (100 mg) and 2.9 g (28.6 mmol) of triethylamine, followed by heating under reflux with stirring. 0.7 g (15.2 mmol) of formic acid was dropwise added thereto, followed by stirring for 5 hours. The reaction liquid was brought to room temperature and filtered to remove the catalyst. Then, the filtrate was subjected to vacuum concentration. Chloroform (200 ml) and water (200 ml) were added to the residue and the obtained mixture was caused liquid-liquid separation. The aqueous phase was further extracted with chloroform (100 ml) once. The organic phases were combined, dried over anhydrous magnesium sulfate and subjected to vacuum concentration. The residue was purified by silica gel column chromatography (a n-hexane/ethyl acetate system) to give 3.6 g of the title compound (yield 85%).

EXAMPLE 114

Synthesis of 2-cyclopropyl-3-(2'-methoxycarbonylbiphenyl-4-yl)methyl-6-bromo-7-methyl-3H-imidazo[4,5-b]-pyridine

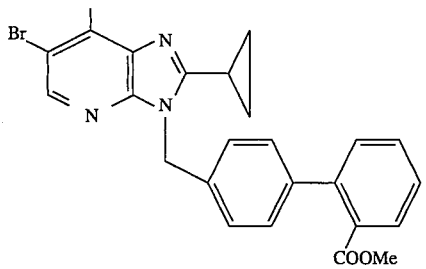

Ethanol (25 ml) was added to 1.0 g (1.9 mmol) of 2-[N-(2'-methoxycarbonylbiphenyl-4-yl)methyl]-cyclopropanecarboxamido- 5-bromo-4-methyl-3-nitropyridine, iron (1.0 g) and acetic acid (2.5 ml), followed by stirring under heating at 80° C. for one hour. The reaction liquid was brought to room temperature and filtered to remove insolubles. The filtrate was subjected to vacuum concentration. Chloroform (50 ml) and water (25 ml) were added to the residue and the obtained mixture was caused liquid-liquid separation. The aqueous phase was further extracted with chloroform (50 ml) once. After the organic phases were combined and washed with an aqueous solution (25 ml) of sodium hydrogencarbonate, the resultant organic phase was dried over anhydrous magnesium sulfate and subjected to vacuum concentration. The residue was purified by silica gel column chromatography (a n-hexane/chloroform system) to give 0.54 g of the title compound (yield 59%).

$^1$H-NMR (600 MHz, CDCl$_3$); δ(ppm) 0.98~1.01 (2H, m), 1.14~1.16 (2H, m), 1.86~1.91 (1H, m), 2.59 (3H, s), 3.54 (3H, s), 5.51 (2H, s), 7.14 (2H, d, J=8.4 Hz), 7.17 (2H, d, J=8.4 Hz), 7.22 (1H, dd, J=7.5, 1.1 Hz), 7.32 (1H, ddd, J=7.5, 7.5, 1.1 Hz), 7.44 (1H, ddd, J=7.5, 7.5, 1.1 Hz), 7.74 (1H, dd, J=7.5, 1.1 Hz), 8.28 (1H, s)

FAB-MS; 446, 448 (MH$^+$)

EXAMPLE 115

Synthesis of 3-cyclopropanecarboxamido-2-[N-(2'-methoxycarbonylbiphenyl-4-yl)methyl]amino-5-bromo-4-methylpyridine

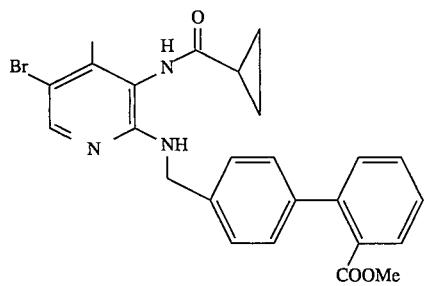

Methanol (50 ml) was added to 1.0 g (1.9 mmol) of 2-[N-(2'-methoxycarbonylbiphenyl-4-yl)methyl]-cyclopropanecarboxamido- 5-bromo-4-methyl-3-nitropyridine, activated carbon (200 mg), 400 mg (7.99 mmol) of hydrazine monohydrate and 2.16 g (7.99 mmol) of ferric chloride hexahydrate, followed by heating under reflux with stirring for 16 hours. The reaction solution was brought to room temperature and filtered through Celite to remove insolubles. After the filtrate was subjected to vacuum concentration, chloroform (200 ml) and water (100 ml) were added to the residue and the obtained mixture was caused liquid-liquid separation. The aqueous phase was further extracted with chloroform (100 ml) twice. The organic phases were combined, dried over anhydrous magnesium sulfate and subjected to vacuum concentration. The residue was purified by silica gel column chromatography (a n-hexane/chloroform system) to give 0.65 g of the title compound (yield 69%).

$^1$H-NMR (600 MHz, CDCl$_3$): δ(ppm) 0.78~0.80 (4H, m), 1.83~1.88 (1H, m), 2.07 (3H, s), 3.58 (3H, s), 4.57 (2H, d, J=6.1 Hz), 6.73 (1H, t, J=6.1 Hz), 7.19 (2H, d, J=8.3 Hz), 7.31 (2H, d, J=8.3 Hz), 7.39 (1H, dd, 5=7.6, 1.2 Hz), 7.45 (1H, ddd, J=7.6, 7.6, 1.2 Hz), 7.58 (1H, ddd, J=7.8, 7.6, 1.2 Hz), 7.69 (1H, dd, J=7.6, 1.2 Hz), 7.98 (1H, s), 9.47 (1H, s)

FAB-MS; 494, 496 (MH$^+$)

EXAMPLE 116

Synthesis of 2-cyclopropyl-3-(2'-methoxycarbonylbiphenyl-4-yl)methyl-6-bromo-7-methyl-3H-imidazo[4,5-b]-pyridine Toluene (20 ml) was added to 600 mg (1.21 mmol) of 3-cyclopropanecarboxamido-2-[N-(2'-methoxycarbonyl-biphenyl- 4-yl)methyl]amino-5-bromo-4-methylpyridine, 100 mg of p-toluenesulfonic acid monohydrate and molecular sieves 4A (500 mg), followed by heating under reflux with stirring for 2 hours. The reaction solution was brought to room temperature and filtered through Celite to remove insolubles. Chloroform (20 ml) and an aqueous solution (50 ml) of sodium hydrogencarbonate were added to the filtrate and the obtained mixture was caused liquid-liquid separation. The aqueous phase was further extracted with chloroform (20 ml) twice. The organic phases were combined, dried over anhydrous magnesium sulfate and subjected to vacuum concentration. The residue was purified by silica gel column chromatography (a n-hexane/ethyl acetate system) title compound (yield 69%).

EXAMPLE 117

Synthesis of 2-cyclopropyl-3-(2'-methoxycarbonylbiphenyl- 4-yl) methyl-7-methyl-3H-imidazo-[4,5-b]pyridine

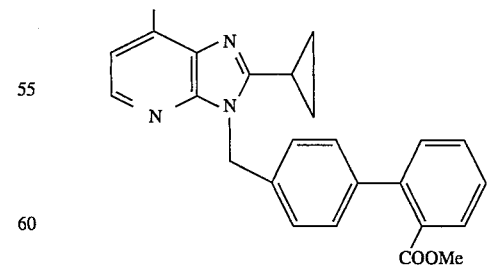

Toluene (20 ml) was added to 1.0 g (1.9 mmol) of 2-[N-(2'-methoxycarbonylbiphenyl-4-yl)methyl]-cyclopropanecarboxamido- 5-bromo-4-methyl-3-nitropyridine, 10% Pd-C (40 mg) and 2.9 g (29 mmol) of triethylamine, followed by heating under reflux with stirring. 1.0 g (22 mmol) of formic acid was dropwise added thereto, followed by stirring for 7 hours. The reaction liquid was brought to room temperature and filtered to remove the catalyst, and then the filtrate was subjected to vacuum concentration. Chloroform (50 ml) and water (20 ml) were added to the residue and the obtained mixture was caused liquid-liquid separation. The aqueous phase was further extracted with chloroform (20 ml) twice. The organic phases were combined, dried over anhydrous magnesium-sulfate and subjected to vacuum concentration. The residue was purified by silica gel column chromatography (a n-hexane/chloroform system) to give 0.65 g of the title compound (yield (86%).

$^1$H-NMR (90 MHz, CDCl$_3$); δ(ppm) 0.82~1.30 (4H, m), 1.80~2.10 (1H, m), 2.64 (3H, s), 3.60 (3H, s), 5.62 (2H, s), 6.98 (1H, d, J=5.0 Hz), 7.22 (4H, s), 7.10~7.56 (3H, m), 7.63~7.85 (1H, m), 8.16 (1H, d, J=5.0 Hz)

FAB-MS; 398 (MH$^+$)

EXAMPLE 118

Synthesis of
2-cyclopropyl-3-(2'-methoxycarbonylbiphenyl-
4-yl)methyl-7-methyl-3H-imidazo-[4,5-b]pyridine Ethanol (50 ml) was added to 1.0 g (1.9 mmol) of 2-[N-(2'-methoxycarbonylbiphenyl-4-yl)methyl]-cyclopropanecarboxamido- 5-bromo-4-methyl-3-nitropyridine, 10% Pd-C (100 mg), 0.4 g (3.9 mmol) of triethylamine and acetic acid (5ml), followed by conducting hydrogenation under normal pressure for 22 hours. After the removal of the catalyst by filtration, the filtrate was subjected to vacuum concentration. Chloroform (100 ml) and an aqueous solution (100 ml) of sodium hydrogencarbonate were added to the residue and the obtained mixture was caused liquid-liquid separation. The aqueous phase was further extracted with chloroform (100 ml) twice. The organic phases were combined, dried over anhydrous magnesium sulfate and subjected to vacuum concentration. The residue was purified by silica gel column chromatography (a n-hexane/ethyl acetate system) to give 0.61 g of the title compound (yield: 80%).

EXAMPLE 119

Synthesis of
2-cyclopropyl-3-(2'-methoxycarbonylbiphenyl-
4-yl)methyl-7-methyl-3H-imidazo[4,5-b]pyridine i-Propanol (100 ml) was added to 1.0 g (1.9 mmol) of 2-[N-(2'-methoxycarbonylbiphenyl-4-yl)methyl]-cyclopropanecarboxamido- 5-bromo-4-methyl-3-nitropyridine, 1.5 g (39 mmol) of sodium borohydride and 2.2 g (12.9 mmol) of cuptic chloride dihydrate, followed by stirring under heating at 60° C. for 6 hours. The reaction liquid was brought to room temperature and filtered to remove insolubles, and then the filtrate was subjected to vacuum concentration. Chloroform (200 ml) and water (100 ml) were added to the residue and the obtained mixture was caused liquid-liquid separation. The aqueous phase was extracted with chloroform (50 ml) twice. The organic phases were combined, dried over anhydrous magnesium sulfate and subjected to vacuum concentration. The residue was purified by silica gel column chromatography (a n-hexane/chloroform system) to give 0.43 g of the title compound (yield 57%).

EXAMPLE 120

Synthesis of
2-cyclopropyl-3-(2'-methoxycarbonylbiphenyl-
4-yl)methyl-7-methyl-3H-imidazo-[4.5-b]pyridine Tetrahydrofuran (100 ml) was added to 1.0 g (1.9 mmol) of 2-[N-(2'-methoxycarbonylbiphenyl-4-yl)methyl]cyclopropanecarboxamido-5 bromo-4-methyl-3-nitropyridine and 10% Pd-C (400 mg), followed by stirring. A 30% aqueous solution (20 ml) of sodium hypophosphite was dropwise added to this solution at room temperature in one hour, followed by further stirring at 60° C. for 2 hours. The reaction liquid was brought to room temperature and filtered to remove the catalyst, and then the filtrate was subjected to vacuum concentration. Chloroform (50 ml) and water (20 ml) were added to the residue and the obtained mixture was caused liquid-liquid separation. The aqueous phase was further extracted with chloroform (20 ml) twice. The organic phases were combined, dried over anhydrous magnesium sulfate and subjected to vacuum concentration. The residue was purified by silica gel column chromatography (a n-hexane/chloroform system) to give 0.35 g of the title compound (yield 46%).

EXAMPLE 121

Synthesis of
2-cyclopropyl-3-(2'-methoxycarbonylbiphenyl-
4-yl)methyl-7-methyl-3H-imidazo-[4,5-b]pyridine Ethanol (100 ml) was added to 1.0 g (1.9 mmol) of 2-[N-(2'-methoxycarbonylbiphenyl-4-yl)methyl]-cycloproanecarboxamido-5-bromo-4-methyl-3-nitropyridine, 10% Pd-C (50mg), 2.0 g (35.8 mmol) of powdered iron and 10 ml )175 mmol) of acetic acid, followed by heating under reflux for 11 hours. The reaction liquid was brought to room temperature and filtered to remove insolubles, and then the filtrate was subjected to vacuum concentration. Chloroform (200 ml) and water (100 ml) were added to the residue and the obtained mixture was caused liquid-liquid separation. The aqueous phase was extracted with chloroform (50 ml) twice. The organic phases were combined, dried over anhydrous magnesium sulfate and subjected to vacuum concentration. The residue was purified by silica gel column chromatography (a n-hexane/chloroform system) to give 0.46 g of the title compound (yield 61%).

EXAMPLE 122

Synthesis of 2-cyclopropyl-3-[2'-(4'',41-dimethyloxazolin-2''-yl)biphenyl-4-yl]methyl-7-methyl-3H-imidazo[4,5-b]pyridine

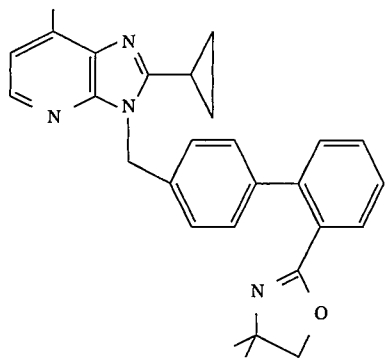

1.71 g (3.0 mmol) of 2-[N-cyclopropanecarbonyl-N-{2'-(4'',4''-dimethyloxazolin-2''-yl)biphenyl-4-yl}-methyl]amino-5-bromo-4-methyl-3-nitropyridine was dissolved in toluene (100 ml), followed by the addition of 10% Pd-carbon catalyst (100 mg), 5.8 g (57.3 mmol) of triethylamine and 1.40 g (30.4 mmol) of formic acid. The obtained mixture was heated under reflux for 10 hours. The reaction liquid was cooled and filtered to remove the catalyst, and then the filtrate was subjected to vacuum concentration. Chloroform and water were added to the residue to conduct extraction After washing with water and drying, vacuum concentration was conducted. The residue was purified by silica gel column chromatography (a n-hexane/ethyl acetate system) to give 1.02 g of the title compound (yield 77%).

$^1$H-NMR (400 MHz, CDCl$_3$); δ(ppm) 1.02–1.12 (4H, m), 1.24 (6H, s), 1.93–2.01 (1H, m), 2.66 (3H, s), 3.47 (2H, s), 5.62 (2H, s), 7.03 (1H, d, J:7.2 Hz), 7.23 (2H, d, J=8.0 Hz), 7.30–7.35 (1H, m), 7.32 (2H, d, J=8.0 Hz), 7.36 (1H, td, J=8.0, 1.0 Hz), 7.47 (1H, td, J=8.0, 1.0 Hz), 7.73 (1H, d, J=8.0 Hz), 8.22 (1H, d, J=7.2 Hz)

FAB-MS; 437 (MH$^+$)

EXAMPLE 123

Synthesis of 2-cyclopropyl-3-(2'-methoxycarbonylbiphenyl-4-yl)methyl-7-methyl-3H-imidazo-[4.5-b]pyridine Ethanol (100 ml) was added to 2.06 g (4.6 mmol) of 2-[N-(2'-methoxycarbonylbiphenyl-4-yl)methyl]-cyclopropanecarboxamido- 4-methyl-3-nitropyridine, 2.56 g (46.0 mmol) of powdered iron and 5 ml (87 mmol) of acetic acid, followed by stirring under heating at 80° C. for 4 hours. The reaction liquid was brought to room temperature and filtered to remove insolubles, and then the filtrate was subjected to vacuum concentration. Chloroform (200 ml) and water (100 ml) were added to the residue and the obtained mixture was caused liquid-liquid separation. The aqueous phase was further extracted with chloroform (50 ml) twice. The organic phases were combined, dried over anhydrous magnesium sulfate and subjected to vacuum concentration. The residue was purified by silica gel column chromatography (a n-hexane/chloroform system) to give 1.27 g of the title compound (yield 69%).

EXAMPLE 124

Synthesis of 2-cyclopropyl-3-(2'-methoxycarbonylbiphenyl-4-yl)methyl-7-methyl-3H-imidazo-[4.5-b]pyridine Toluene (30 ml) was mixed with 3.0 g (6.3 mmol) of 2-cyclopropyl-3-(2'-methoxycarbonylbiphenyl-4-yl)methyl- 6-bromo-7-methyl-3H-imidazo[4,5-b]pyridine, 10% Pd-C (100 mg) and 9.6 g (95 mmol) of triethylamine, followed by the dropwise addition of 2.9 g (63 mmol) of formic acid under stirring. The obtained mixture was heated under reflux for 10 hours. The reaction liquid was brought to room temperature, and filtered to remove the catalyst, and then the filtrate was subjected to vacuum concentration. Chloroform (100 ml) and water (100 ml) were added to the residue and the obtained mixture was caused liquid-liquid separation. The aqueous phase was further extracted with chloroform (50 ml) twice. The organic phases were combined, dried over anhydrous magnesium sulfate and subjected to vacuum concentration. The residue was purified by silica gel column chromatography (a n-hexane/ethyl acetate system) to give 2.3 g of the title compound (yield 92%).

EXAMPLE 125

Synthesis of 2-cyclopropyl-3-(2'-methoxycarbonylbiphenyl-4-yl)-methyl-7-methyl-3H-imidazo-[4,5-b]pyridine Toluene (50 ml) was mixed with 2.0 g (4.0 mmol) of 3-cyclopropanecarboxamido-2-[N-(2'-methoxycarbonylbiphenyl- 4-yl)methyl]amino-5-bromo-4-methylpyridine, 10% Pd-C (100 mg) and 6.1 g (60 mmol) of triethylamine, followed by heating under reflux with stirring. 2.0 g (43 mmol) of formic acid was dropwise added thereto, followed by heating under reflux for 7 hours. The reaction liquid was brought to room temperature and filtered to remove the catalyst, and then the filtrate was subjected to vacuum concentration. Chloroform (100 ml) and water (100 ml) were added to the residue and the obtained mixture was caused liquid-liquid separation. The aqueous phase was further extracted with chloroform (50 ml) twice. The organic phases were combined, dried over anhydrous magnesium sulfate and subjected to vacuum concentration. The residue was purified by silica gel column chromatography (a n-hexane/chloroform system) to give 1.45 g of the title compound (yield 90%).

EXAMPLE 201

Synthesis of 2-valerylamino-5-bromo-4-methyl-3-nitropyridine

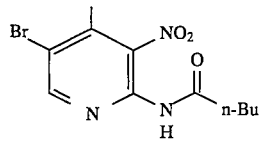

A mixture comprising 10 g (43.1 mmol) of 2-amino-5-bromo-4-methyl-3-nitropyridine and 6.8 g of pyridine was heated to 110° C. in a nitrogen atmosphere. 5.7 g (47.4 mmol) of valeroyl chloride was dropwise added thereto and the mixture was stirred at 110° C. for 5 hours. The reaction mixture was brought to room temperature, followed by the addition of methylene chloride (50 ml) and water (50 ml).

The organic phase was separated. The aqueous phase was further extracted with methylene chloride (50 ml). The organic phases were combined, dried over anhydrous magnesium sulfate and subjected to vacuum concentration to give a crude crystal. It was recrystallized from ethyl acetate to give 11 g of 2-valerylamino-5-bromo-4-methyl-3-nitropyridine (yield 81%).

m.p.; 134°–135° C.

¹NMR (400 MHz, CDCl₃); δ(ppm) 0.94 (3H, t, J=7.4 Hz), 1.35~1.44 (2H, m), 1.65~1.73 (2H, m), 2.45 (2H, t, J=7.5 Hz), 2.52 (3H, s), 7.97 (1H, br-s), 8.58 (1H, s)

FAB-MS; 316, 318 (MH⁺)

EXAMPLE 202

Synthesis of 2-[N-(2'-cyanobiphenyl-4-yl)methyl]valerylamino-5-bromo-4-methyl-3-nitropyridine

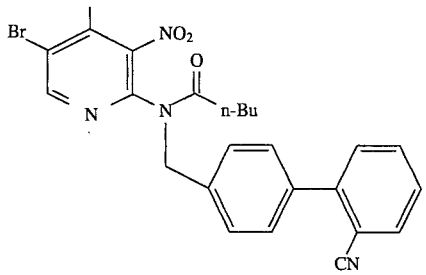

4.0 g (13 mmol) of 5-bromo-4-methyl-3-nitro-2-valerylaminopyridine was added to a solution of 1.7 g (15 mmol) of potassium-t-butoxide in tetrahydrofuran (30 ml), followed by stirring at room temperature for 45 minutes. Then, this solution was heated, followed by the dropwise addition of a solution of 4.1 g (15 mmol) of 2-(4'-bromomethylphenyl)benzonitrile in tetrahydrofuran (30 ml) under reflux. After the completion of the dropwise addition, the obtained mixture was stirred for 3 hours. The reaction mixture was brought to room temperature, followed by the addition of ethyl acetate (50 ml) and a saturated aqueous solution of ammonium chloride (100 ml) to conduct extraction. The aqueous phase was further extracted with ethyl acetate (50 ml) twice. The organic phases were combined, dried over anhydrous magnesium sulfate and concentrated. The residue of the concentration was purified by silica gel column chromatography (ethyl acetate/n-hexane) to give 3.5 of 2-[N-(2'-cyanobiphenyl-4-yl)methyl]valerylamino-5-bromo- 4-methyl-3-nitropyridine (yield 55%).

¹NMR (600 MHz, CDCl₃); δ (ppm) 0.86 (3H, t, J=7.4 Hz), 1.23~1.32 (2H, m), 1.58~1.67 (2H, m), 2.11 (2H, br), 2.46 (3H, s), 5.18 (2H, br), 7.26~7.76 (8H, m), 8.68 (1H, br-s)

FAB-MS; 507, 509 (MH⁺)

EXAMPLE 203

Synthesis of 2-[N-(2'-cyanobiphenyl-4-yl)methyl]cyclopropanecarboxamido-5-bromo-4-methyl-3-nitropyridine

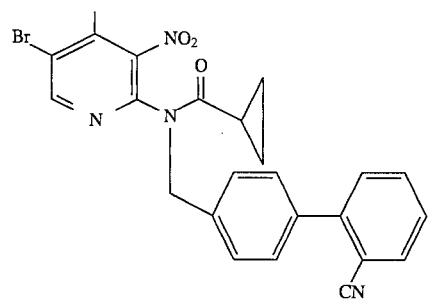

2.0 g (6.7 mmol) of 2-cyclopropanecarboxamido-5-bromo- 4-methyl-3-nitropyridine was added to a solution of 0.9 g (8.0 mmol) of potassium-t-butoxide in tetrahydrofuran (35 ml), followed by stirring at room temperature for one hour. Then, this solution was heated, followed by the dropwise addition of a solution of 2.2 g (8.0 mmol) of 2-(4'-bromomethylphenyl)benzonitrile in tetrahydrofuran (10 ml) under reflux. After the completion of the dropwise addition, the obtained mixture was stirred for 3 hours. The reaction mixture was brought to room temperature, followed by the addition of ethyl acetate (50 ml) and a saturated aqueous solution of ammonium chloride (50 ml) to conduct extraction. The aqueous phase was further extracted with ethyl acetate (50 ml) once and with chloroform (50 ml) once. The organic phases were combined, dried over anhydrous magnesium sulfate and subjected to vacuum concentration. The residue was purified by silica gel column chromatography (ethyl acetate/n-hexane) to give 2.1 g of 2-[N-(2'-cyanobiphenyl-4-yl)methyl]cyclopropanecarboxamido- 5-bromo-4-methyl-3-nitropyridine (yield 64%).

¹NMR (600 MHz, CDCl₃); δ (ppm) 0.7~0.9 (2H, br), 1.0~1.1 (2H, br), 1.52~1.54 (1H, br), 2.44 (3H, s), 4.8~5.6 (2H, br), 7.8~7.6 (4H, br), 7.41 (1H, t, J=7.7 Hz ), 7.48 (1H, d, J=7.7 Hz ) , 7.61 (1H, t, J=7.7 Hz), 7.73 (1H, d, J=7.7 Hz), 8.68 (1H, s)

FAB-MS; 491, 493 (MH⁺)

EXAMPLE 204

Synthesis of 2-butyl-3-(2-cyanobiphenyl-4-yl)methyl-7-methyl-3H-imidazo[4,5-b]-pyridine

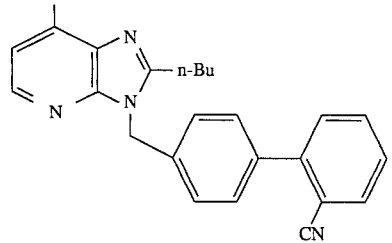

Toluene (150 ml) was added to 5.0 g (9.9 mmol) of 2-[N-(2'-cyanobiphenyl-4-yl)methyl]valerylamino-5-bromo- 4-methyl-3-nitropyridine, 10% Pd-C (500 mg), 9.0 g (89 mmol) of triethylamine and 2.1 g (46 mmol) of formic acid. The obtained mixture was stirred and heated under reflux for 11 hours. After the reaction liquid was brought to room temperature and filtered to remove the catalyst, vacuum concentration was effected. Chloroform (200 ml) and water (200 ml) were added to the residue and the obtained mixture was caused liquid-liquid separation. The aqueous phase was further extracted with chloroform (200 ml) once. The organic phases were combined, dried over anhydrous magnesium sulfate and subjected to vacuum concentration. The residue was purified by silica gel column chromatography (n-hexane/chloroform) to give 2.7 g of 2-butyl-3-(2'-cyanobiphenyl-4-yl)methyl-7-methyl-3H-imidazo[4,5-b]pyridine (yield 72%).

$^1$H NMR (600 MHz, CDCl$_3$); δ (ppm) 0.91 (3H, t, J=7.3 Hz), 1.37~1.46 (2H, m), 1.71~1.78 (2H, m), 2.70 (3H, d, J=0.6 Hz), 2.86 (2H, t, J=7.8 Hz), 5.56 (2H, s), 7.04 (1H, dd, J=4.9, 0.6 Hz), 7.24 (2H, d, J=8.4 Hz), 7.41~7.48 (2H, m), 7.49 (2H, d, J=8.4 Hz), 7.64~7.70 (1H, m), 7.74~7.76 (1H, m), 8.21 (1H, d, J=4.9 Hz)

FAB-MS: 381 (MH$^+$)

EXAMPLE 205

Synthesis of 2-Cyclopropyl-3-(2'-cyanobiphenyl-4-yl)methyl-7-methyl-3H-imidazo[4,5-b]-pyridine

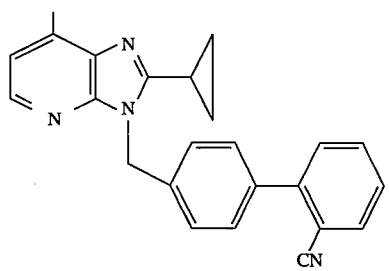

Toluene (200 ml) was added to 5.0 g (10 mmol) of 2-[N-(2'-cyanobiphenyl-4-yl)methyl]cyclopropane carboxamido-5-bromo-4-methyl-3-nitropyridine. 10% Pd-C (500 mg), 26 g (257 mmol) of triethylamine and 10 g (217 mmol) of formic acid. The obtained mixture was stirred and heated under reflux for 7 hours. After the reaction liquid was brought to room temperature and filtered to remove the catalyst, vacuum concentration was effected. Chloroform (200 ml) and water (200 ml) were added to the residue and the obtained mixture was caused liquid-liquid separation. The aqueous phase was further extracted with chloroform (200 ml) once. The organic phases were combined, dried over anhydrous magnesium sulfate and subjected to vacuum concentration. The residue was purified by silica gel column chromatography (n-hexane/chloroform) to give 2.8 g of 2-cyclopropyl- 3-(2'-cyanobiphenyl-4-yl)methyl-7-methyl-3H-imidazo-[4,5-b]pyridine (yield 75%).

$^1$NMR (600 MHz, CDCl$_3$); δ (ppm) 1.03~1.08 (2H, m), 1.20~1.25 (2H, m), 1.93~1.99 (1H, m), 2.65 (3H, s), 5.66 (2H, s), 7.00 (1H, d, J=5.0 Hz), 7.31 (2H, d, J=8.5 Hz), 7.41~7.48 (2H, m), 7.50 (2H, d, J=8.5 Hz), 7.60~7.64 (1H, m), 7.74~7.76 (1H, m), 8.19 (1H, d, J=5.0 Hz)

FAB-MS; 365 (MH$^+$)

EXAMPLE 206

Synthesis of 2-[N-(2'-cyanobiphenyl-4-yl)methyl]valerylamino-4-methyl -3-nitropyridine,

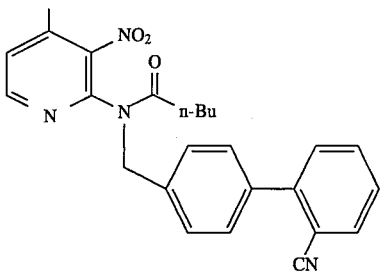

Toluene (150 ml) was added to 5.0 g (9.9 mmol) of 2-[N-(2'-cyanobiphenyl-4-yl)methyl]valerylamino-5-bromo- 4-methyl-8-nitropyridine, 10% Pd-C (500 mg) and 3.0 g (80 mmol) of triethylamine, followed by heating under reflux. 700 mg (15 mmol) of formic acid was dropwise added thereto, followed by stirring for 6 hours. After the reaction liquid was brought to room temperature and filtered to remove the catalyst, vacuum concentration was effected. Chloroform (200 ml) and water (200 ml) were added to the residue and the obtained mixture was caused liquid-liquid separation. The aqueous phase was further extracted with chloroform (200 ml) once. The organic phases were combined, dried over anhydrous magnesium sulfate and subjected to vacuum concentration. The residue was purified by silica gel column chromatography (n-hexane/chloroform) to give 3.5 g of 2-[N-(2'-cyanobiphenyl- 4-yl)methyl]valerylamino-4-methyl-3-nitropyridine (yield 83%).

$^1$NMR (600 MHz, CDCl$_3$); δ (ppm) 0.82 (3H, t, J=7.4 Hz), 1.23~1.27 (2H, m) , 1.58~1.68 (2H, m), 2.09 (2H, br), 2.39 (3H, s), 5.20 (2H, br), 7.21~7.74 (9H, m), 8.45 (1H, br-s)

FAB-MS; 429 (MH$^+$)

EXAMPLE 207

Synthesis of 2-(2'-cyanobiphenyl-4-yl)methylamino-3-cyclopropanecarboxamido-5-bromo-4-methylpyridine Methanol (50 ml) was added to 3.0 g (6.1 mmol) of 2-[N-(2'-cyanobiphenyl-4-yl)methyl]cyclopropanecarboxamido- 5-bromo-4-methyl-3-nitropyridine, 8.6 g (172 mmol) of hydrazine monohydrate, activated carbon (300 mg) and 9.6 g (35.5 mmol) of ferric chloride hexahydrate, followed by heating under reflux for 25 hours. After the reaction liquid was brought to room temperature and filtered to remove insolubles, vacuum concentration was effected.

Chloroform (50 ml) and water (50 ml) were added to the residue and the obtained mixture was caused liquid-liquid separation. The aqueous phase was further extracted with chloroform (20 ml) twice. The organic phases were combined, dried over anhydrous sodium sulfate and subjected to vacuum concentration. The residue was purified by silica gel column chromatography (n-hexane/ethyl acetate) to give 1.3 g of 2-(2'-cyanobiphenyl-4-yl)methylamino- 3-cyclopropanecarboxamido-5-bromo- 4-methylpyridine (yield 46%).

$^1$NMR (600 MHz, CDCl$_3$); δ (ppm) 0.85~0.92 (2H, m), 1.00~1.08 (2H, m), 1.77~1.86 (1H, m), 2.27 (3H, s), 4.70 (2H, s), 6.00 (1H, br-s), 7.41 (1H, ddd, J=7.7, 7.7, 1.5 Hz), 7.43 (2H, d, J=8.3 Hz), 7.47 (1H, dd, J=7.7, 1.5 Hz), 7.48 (2H, d, J=8.3 Hz), 7.62 (1H, ddd, J=7.7, 7.7, 1.5 Hz), 7.72 (1H, dd, J=7.7, 1.5 Hz), 8.05 (1H, br-s), 8.19 (1H, s)

FAB-MS; 461, 463 (MH$^+$)

EXAMPLE 208

Synthesis of 2-cyclopropyl-3-(2'-cyanobiphenyl-4-yl)methyl-7-methyl-3H-imidazo[4,5-b]-pyridine Toluene (30 ml) was added to 2.0 g (4.3 mmol) of 2-(2'-cyanobiphenyl-4-yl)methylamino-3-cyclopropanecarboxamido- 5-bromo-4-methyl-pyridine, 1.0 g (21.7 mmol) of formic acid, 8.5 g (84.6 mmol) of triethylamine and 10% Pd-C (300 mg), followed by heating under reflux for 6 hours. After the reaction liquid was brought to room temperature and filtered to remove the catalyst, vacuum concentration was effected. Chloroform (100 ml) and water (50 ml) were added to the residue and the obtained mixture was caused liquid-liquid separation. The aqueous phase was further extracted with chloroform (50 ml) twice. The organic phases were combined, dried over anhydrous magnesium sulfate and subjected to vacuum concentration. The residue was purified by silica gel column chromatography (n-hexane/ethyl acetate) to give 1.3 g of 2-cyclopropyl-3-(2'-cyanobiphenyl-4-yl)methyl- 7-methyl-3H-imidazo[4,5-b]pyridine (yield 82%).

EXAMPLE 209

Synthesis of 2-cyclopropyl-3-(2cyanobiphenyl-4-yl)methyl-6-bromo-7-methyl-3H-imidazo-[4,5-b]-pyridine

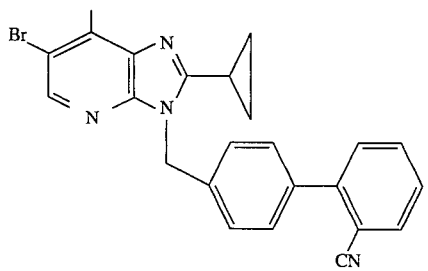

Ethanol (50 ml) was added to 8.0 g (6.1 mmol) of 2-[N-(2'-cyanobiphenyl-4-yl)methyl]cyclopropanecarboxamido- 5-bromo-4-methyl-3-nitropyridine, 3.0 g of powdered iron and acetic acid (10 ml), followed by stirring under heating at 80° C. for one hour. After the reaction liquid was brought to room temperature and filtered to remove the catalyst, vacuum concentration was effected. Chloroform (100 ml) and water (50 ml) were added to the residue and the obtained mixture was caused liquid-liquid separation. The aqueous phase was further extracted with chloroform (50 ml). After the organic phases were combined and washed with an aqueous solution (100 ml) of sodium hydrogencarbonate, the resultant organic phase was dried over anhydrous magnesium sulfate and subjected to vacuum concentration. The residue was purified by silica gel column chromatography (n-hexane/chloroform) to give 1.8 g of 2-cyclopropyl-3-(2'-cyanobiphenyl-4-yl)-methyl-6-bromo-7-methyl-3H-imidazo[4,5-b]pyridine (yield 67%).

$^1$NMR (600 MHz, CDCl$_3$); δ (ppm) 1.02~1.13 (2H, m), 1.21~1.28 (2H, m), 1.92~2.00 (1H, m), 2.66 (3H, s), 5.61 (2H, s), 7.30 (2H, d, J=S.0 Hz), 7.42 (1H, ddd, J=7.5, 7.5, 1.2 Hz), 7.45 (1H, dd, J=7.5, 1.2 Hz), 7.49 (2H, d, J=8.0 Hz), 7.62 (1H, ddd, J=7.5, 7.5, 1.2 Hz), 7.74 (1H, dd, J=7.5, 1.2 Hz), 8.35 (1H, s)

FAB-MS; 443, 445 (MH$^+$)

EXAMPLE 210

Synthesis of 2-cyclopropyl-3-(2'-cyanobiphenyl-4-yl)methyl-6-bromo-7-methyl-3H-imidazo-[4,5-b]-pyridine Toluene (20 ml) was added to 2.0 g (4.3 mmol) of 2-(2'-cyanobiphenyl-4-yl)methylamino-3-cyclopropanecarboxamido- 5-bromo-4-methylpyridine, p-toluenesulfonic acid monohydrate (200 mg) and Molecular Sieves 4A (500 mg), followed by heating under reflux with stirring for 3 hours. The reaction solution was brought to room temperature and filtered through Celite to remove insolubles. Chloroform (100 ml) and an aqueous solution (100 ml) of sodium hydrogencarbonate were added to the filtrate and the obtained mixture was caused liquid-liquid separation. The aqueous phase was further extracted with chloroform (50 ml) twice. The organic phases were combined, dried over anhydrous magnesium sulfate and subjected to vacuum concentration. The residue was purified by silica gel column chromatography (n-hexane/ethyl acetate) to give 1.7 g of 2-cyclopropyl-3-(2'-cyanobiphenyl- 4-yl)methyl-6-bromo-7-methyl-3H-imidazo-[4,5-b]pyridine (yield 88%).

EXAMPLE 211

Synthesis of 2-cyclopropyl-3-(2'-cyanobiphenyl-4-yl)methyl-7-methyl-3H-imidazo[4,5-b]-pyridine Toluene (30 ml) was added to 2.0 g (4.5 mmol) of 2-cyclopropyl-3-(2'-cyanobiphenyl-4-yl)methyl-6-bromo-7-methyl-3H-imidazo[4,5-b]pyridine, 1.24 g (27.0 mmol) of formic acid, 4.55 g (45.0 mmol) of triethylamine and 10% Pd-C (100 mg), followed by heating under reflux for 6 hours. After the reaction liquid was brought to room temperature and filtered to remove the catalyst, vacuum concentration was effected. Chloroform (50 ml) and water (50 ml) were added to the residue and the obtained mixture was caused liquid-liquid separation. The aqueous phase was further extracted with chloroform (30 ml) twice. The organic phases were combined, dried over anhydrous magnesium sulfate and subjected to vacuum concentration. The residue was purified by silica gel column chromatography (n-hexane/ethyl acetate) to give 1.28 g of 2-cyclopropyl-3-(2'-cyanobiphenyl-4-yl)-methyl- 7-methyl-3H-imidazo[4,5-b]pyridine (yield 78%).

EXAMPLE 212

Synthesis of 2-cyclopropyl-3-(2'-cyanobiphenyl-4-yl)methyl-7-methyl-3H-imidazo[4,5-b]-pyridine Toluene (50 ml) was added to 4.0 g (9.7 mmol) of 2-[N-(2'-cyanobiphenyl-4-yl)methyl]cyclopropanecarboxamido- 4-methyl-3-nitropyridine, 4.5 g (97.8 mmol) of formic acid, 14.7 g (145.5 mmol) of triethylamine and 10% Pd-C (200 mg), followed by heating under reflux for 15 hours. After the reaction liquid was brought to room temperature and filtered to remove the catalyst, vacuum concentration was effected. Chloroform (100 ml) and water (100 ml) were added to the residue and the obtained mixture was caused liquid-liquid separation. The aqueous phase was further extracted with chloroform (50 ml) twice. The organic phases were combined, dried over anhydrous magnesium sulfate and subjected to vacuum concentration. The residue was purified by silica gel column chromatography (n-hexane/ethyl acetate) to give 2.9 g of 2-cyclopropyl-3-(2'-cyanobiphenyl-4-yl)methyl- 7-methyl-3H-imidazo[4,5-b]pyridine (yield 83%).

Next, Referential Examples, wherein an objective compound is prepared from the 2-alkyl-3-(biphenyl- 4-yl)methyl-3H-imidazo[4,5-b]pyridine derivatives (II) which has been prepared by the use of an active biphenyl derivative (IV) according to the present invention as a synthesis intermediate, in the production of 2-alkyl-3-(2'-alkoxycarbonylbiphenyl-4-yl)methyl- 3H-imidazo[4,5-b]pyridine derivatives which are antagonists against angiotensin II receptor and are useful as an antihypertensive drug or a remedy for hemal lesions will be given.

REFERENTIAL EXAMPLES

Referential Example 1

Synthesis of 2-cyclopropyl-3-(2-carboxybiphenyl-4-yl)methyl-7-methyl-3H-imidazo-[4,5-b]pyridine

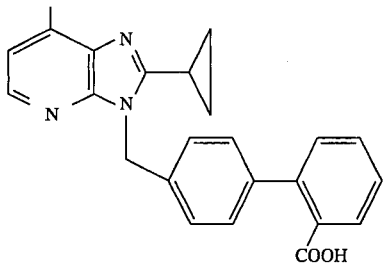

Ethanol (40 ml) and a 10% aqueous solution (20 ml) of sodium hydroxide were added to 1.32 g (3.3 mmol) of 2-cyclopropyl-3-(2'-methoxycarbonylbiphenyl- 4-yl)methyl-7-methyl-3H-imidazo[4,5-b]pyridine, followed by heating under reflux for 2 hours. After the reaction liquid was cooled, it was concentrated to about one-half the initial volume, and neutralized with 2N hydrochloric acid and acetic acid. The crystal thus precipitated was recovered by filtration and recrystallized from aqueous ethanol to give 1.03 of the title compound (yield 81%).

$^1$H-NMR (600 MHz, DMSO-$d_6$); δ(ppm) 1.06 (4H, m), 2.27 (1H, tt, J=8.0, 5.0 Hz), 2.80 (3H, S), 5.63 (2H, s), 7.04 (1H, d, J=5.0 Hz), 7.27 (4H, m), 7.33 (1H, dd, J=8.0, 1.0 Hz) 7.43 (1H, ddd, J=8.0, 8.0, 1.0 Hz), 7.54 (1H, ddd, J=8.0, 8.0, 2.0 Hz), 7.70 (1H, dd, J=8.0, 2.0 Hz), 8.13 (1H, d, J=5.0 Hz), 12.70 (1H, br-s)

Referential Example 2

Synthesis of 2-cyclopropyl-3-(2'-carboxybiphenyl-4-yl)methyl-7-methyl-3H-imidazo-[4,5-b]pyridine 2.7 g (6.2 mmol) of 2-cyclopropyl-3-[2'-(4",4"-dimethyloxazolin- 2"-yl)biphenyl-4-yl]methyl-7-methyl- 3H-imidazo[4,5-b]pyridine was dissolved in ethanol (50 ml), followed by the addition of 4N hydrochloric acid (25 ml). The obtained mixture was heated under reflux for 9 hours. The reaction liquid was cooled and added to a saturated aqueous solution of sodium hydrogencarbonate, followed by the extraction with chloroform After washing with water and drying vacuum concentration was conducted. The residue was dissolved in ethanol (25 ml), followed by the addition of a 2N aqueous solution (25 ml) of sodium hydroxide. The obtained mixture was heated under reflux for 6 hours. The reaction liquid was concentrated to dryness, and then water was added thereto to dissolve the residue. Then, the solution obtained was neutralized with 2N hydrochloric acid and acetic acid. The crystal thus precipitated was recovered by filtration and recrystallized from aqueous ethanol to give 1.92 g of the title compound (yield 81%).

Referential Example 3

Synthesis of 2-Cyclopropyl- 3-(2'-carboxybiphenyl-4-yl)methyl-7-methyl-3H-imidazo[4,5-b]pyridine Water (8.7 ml) and 5.8 g of sulfuric acid were added to 5.0 g (11.5 mmol) of 2-cyclopropyl-3-[2'-( 4",4"-dimethyloxazolin-2"-yl)biphenyl-4-yl]methyl- 7-methyl-3H-imidazo [4,5-b]pyridine, followed by heating under reflux for 36 hours. The pH of the reaction mixture was adjusted to 6 with a 10% aqueous solution of sodium hydroxide and acetic acid. The crystal thus precipitated was recovered by filtration and recrystallized from aqueous ethanol to give 3.74 of the title compound (yield 85%).

We claim:

1. A 2-[N-(biphenyl-4-yl)methyl]amino-3-acylaminopyridine or a 2-[N-(biphenyl-4-yl)methyl]amino-3-alkoxycarbonylaminopyridine derivative (VI) represented by the following formula:

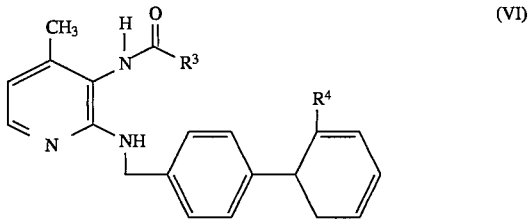

(VI)

wherein $R^1$ represents a hydrogen atom or a bromine atom or a chlorine atom; $R^2$ represents a hydrogen atom or a methyl group; $R^3$ represents a cycloalkyl group, a lower alkyl group or a lower alkoxy group; and $R^4$ represents a group represented by the following formula:

—$COOR^5$ wherein $R^5$ represents a lower alkyl group, a cycloalkyl group, an alkoxyalkyl group, a thioalkoxyalkyl group, a cycloether group, an aryl group, an aralkyl group, an alkenyl group, an alkynyl group or a trialkylsilyl group, or $R^4$ is a group represented by the following general formula:

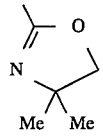

2. The compound according to claim 1 wherein $R^1$ is a bromine or a chlorine atom; and $R^2$ is a methyl group.

3. The compound according to claim 1 wherein $R^3$ is a cycloalkyl.

4. The compound according to claim 1 wherein $R^1$ is a hydrogen atom; and $R^3$ is a cycloalkyl.

5. The compound according to claim 15 wherein $R^1$ is a bromine or chlorine atom; and $R^2$ is a hydrogen atom.

6. A 2-[N-(2'-cyanobiphenyl- 4-yl)methyl]-amino-5-halogeno-3-alkylamidopyridine or a 2-[N-(2'-cyanobiphenyl-4-yl)methyl]-amino-5-halogeno-3-alkoxycarbonylaminopyridine derivative (VII) represented by the following formula

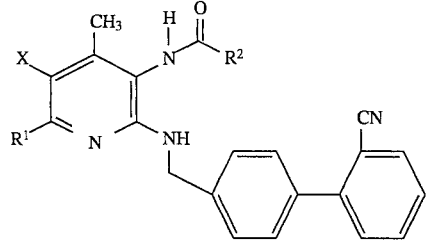

(VII)

wherein $R^1$ represents a hydrogen atom or a methyl group; $R^2$ represents a cycloalkyl group, a lower alkyl group or a lower alkoxyl group and X represents a halogen atom.

7. The compound according to claim 6 wherein X is a bromine atom.

* * * * *

UNITED STATES PATENT AND TRADEMARK OFFICE
CERTIFICATE OF CORRECTION

PATENT NO. : 5,559,236
DATED : September 24, 1996
INVENTOR(S) : Yoshio Urawa et al.

It is certified that error appears in the above-indentified patent and that said Letters Patent is hereby corrected as shown below:  On the title page:

Section 62, after "Ser. No. 256,869" insert

--filed on August 5, 1994--

Signed and Sealed this

Fourth Day of March, 1997

Attest:

BRUCE LEHMAN

Attesting Officer

Commissioner of Patents and Trademarks